United States Patent
Boyd et al.

(10) Patent No.: US 8,703,116 B2
(45) Date of Patent: *Apr. 22, 2014

(54) MODIFIED MACROMOLECULE

(71) Applicant: Starpharma Pty Ltd, Melbourne (AU)

(72) Inventors: Benjamin James Boyd, Warrandyte (AU); Lisa Michelle Kaminskas, Brunswick West (AU); Christopher John Hamilton Porter, Port Melbourne (AU); Peter Karellas, Reservoir (AU); Guy Yeoman Krippner, Mt Waverley (AU); Pasquale Razzino, South Yarra (AU); Brian Devlin Kelly, Ringwood East (AU); Zemin Wu, Vermont South (AU); Sue Pallich, Caroline Springs (AU)

(73) Assignee: Starpharma Pty Limited, Melbourne, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/725,844

(22) Filed: Dec. 21, 2012

(65) Prior Publication Data

US 2013/0116432 A1 May 9, 2013

Related U.S. Application Data

(62) Division of application No. 12/161,688, filed as application No. PCT/AU2006/000637 on May 15, 2006, now Pat. No. 8,337,823.

(30) Foreign Application Priority Data

Jan. 20, 2006 (AU) ................................ 2006900310

(51) Int. Cl.
*A61K 31/74* (2006.01)
*C07D 487/00* (2006.01)

(52) U.S. Cl.
USPC ........................................ 424/78.18; 544/256

(58) Field of Classification Search
USPC .......................................... 544/256; 549/510
See application file for complete search history.

(56) References Cited

U.S. PATENT DOCUMENTS 5,229,490 A 7/1993 Tam
6,190,650 B1 2/2001 Matthews et al.
(Continued)

FOREIGN PATENT DOCUMENTS

JP 9512264 A 12/1997
JP 2004515457 A 5/2004
(Continued)

OTHER PUBLICATIONS

Jevprasesphant et al. ("The influence of surface modification on the cytotoxicity of PAMAM dendrimers," in International Journal of Pharmaceutics, 252, (2003), 263-266).*

(Continued)

*Primary Examiner* — Blessing M Fubara
(74) *Attorney, Agent, or Firm* — Knobbe, Martens, Olson & Bear, LLP

(57) ABSTRACT

The present invention relates to a macromolecule having a controlled terminal group stoichiometry, the macromolecule including a surface layer, at least one subsurface layer and at least two terminal groups including: a first terminal group which is a residue of a pharmaceutically active agent, a derivative thereof or precursor therefor; and a second terminal group selected to modify the pharmacokinetics of the pharmaceutically active agent and/or macromolecule, wherein terminal group stoichiometry refers to the number and type of terminal groups.

12 Claims, 28 Drawing Sheets

Structure A - BHALys [Lys]₈ [NH₂]₁₆

Structure B - BHALys [Lys]₁₆ [NH₂]₃₂

(56) References Cited

U.S. PATENT DOCUMENTS

Figure 1A:
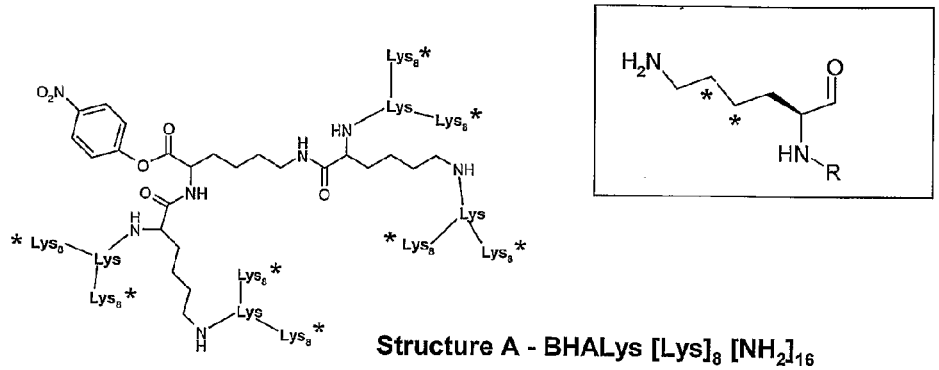

| | | | |
|---|---|---|---|
| 6,426,067 B1 | 7/2002 | Matthews et al. | |
| 8,337,823 B2 * | 12/2012 | Boyd et al. | 424/78.1 |
| 8,420,067 B2 * | 4/2013 | Krippner et al. | 424/78.08 |

FOREIGN PATENT DOCUMENTS

| | | |
|---|---|---|
| JP | 2005532276 A | 10/2005 |
| WO | WO 95/28966 A1 | 11/1995 |
| WO | 98/18494 A1 | 5/1998 |
| WO | WO 00/15239 A1 | 3/2000 |
| WO | WO 00/15240 A1 | 3/2000 |
| WO | WO 01/87348 A2 | 11/2001 |
| WO | WO 02/079298 A1 | 10/2002 |
| WO | WO 02/079299 A1 | 10/2002 |
| WO | 03/055935 A1 | 7/2003 |
| WO | WO 03/076455 A2 | 9/2003 |
| WO | 2007/048190 A1 | 5/2007 |

OTHER PUBLICATIONS

Majaros et al. ("PAMAM Dendrimer-Bases Multifunctional Conjugate for Cancer Therapy: Synthesis, Characterization, and Functionality," in Biomacromolecules, 2006, 7, 572-579).*

Okuda et al. ("Pegylated lysine dendrimers for tumor-selective targeting after intravenous injection in tumor bearing mice," in Journal of Controlled Release 116 (2006) 330-336).*

Tansey, et al., "Synthesis and characterization of branched poly(I-gultamic acid) as a biodegradable drug carrier", Journal of Controlled Release, Elseveier, Amsterdam, NL, vol. 94, No. 1, Jan. 8, 2004, pp. 39-51, XP004480736.

Majaros, et al., "Poly(amidoamine) Dendrimer-Based Multifunctional Engineered Nanodevice for Cancer Therapy", Journal of Medicinal Chemistry, vol. 48, No. 19, Sep. 1, 2005, pp. 5892-5899, XP055054434.

Supplementary European Search Report dated Mar. 7, 2013 for European Application No. 06 72 1507.

Geezer, A.E. et al. 2003 "Dendrimers as potential drug carriers; encapsulation of acidic hydrophobes within water soluble PAMAM derivatives" *Tetrahedron* 59:3873-3880.

Boas et al., "Dendrimers in drug research." in Critical Review of the Chemical Society Reviews, Dec. 2003.

El-Sayed, M. et al. 2002 "Transepithelial transport of poly(amidoamine) dendrimers across Caco-2 cell monolayers" *Journal of Controlled Release* 81:355-365.

Florence, A.T. et al. 2000 "Oral uptake and translocation of a polylysine dendrimer with a lipid surface" *Journal of Controlled Release* 65:253-259.

Fréchet, J. M. 2003 "Dendrimers and Other Dendritic Macromolecules: From Building Blocks to Functional Assemblies in Nanoscience and Nanotechnology" *Journal of Polymer Science: Part A: Polymer Chemistry* 41:3713-3725.

Gillies, E. R. et al. 2002 "Designing Macromolecules for Therapeutic Applications: Polyester Dendrimer-Poly(ethylene oxide) "Bow-Tie" Hybrids with Tunable Molecular Weight and Architecture" *J. Am. Chem. Soc.* 124:14137-14146.

Gillies, E. R. et al. 2005 "Biological Evaluation of Polyester Dendrimers: Poly(ethylene oxide) "Bow-Tie" Hybrids with Tunable Molecular Weight and Architecture" *Molecular Pharmaceutics* (2):129-138.

Gillies, E. R. et al. 2005 "Dendrimers and dendritic polymers in drug delievery" *Discovery Drug Today* 10(1):35-43.

Gillies, E.R. et al., Dendrimers and dendritic polymers in drug delivery, Drug Discovery Today, Jan. 2005, vol. 10, No. 1, pp. 35-43.

Jevprasesphant, R. et al. 2003 "The influence of surface modification on the cytotoxicity of PAMAM dendrimers" *International Journal of Pharmaceutics* 252:263-266.

Jevprasesphant, R. et al. 2004 "Transport of dendrimer nanocarriers through epithelial cells via the transcellular route" *Journal of Controlled Release* 97:259-267.

Kim et al., "Systematic Investigation of Polyamidoamine Dendrimers Surface-Modified with Polyethylene glycol for Drug Delivery Applications: Synthesis, Characterization, and Evaluation of Cytotoxicity," in Bioconjugate Chem. 2008, 19, 1660-1672.

Kobayashi, H. et al. 1999 "Evaluation of the in vivo Biodistribution of Indium-111 and Yttrium-88 Labeled Dendrimer-1B4M-DTPA and Its Conjugation with Anti-Tac Monoclonal Antibody" *Bioconjugate Chem.* 10 (1):103-111.

Kobayashi, H. et al. 2001 "Dynamic Micro-Magnetic Resonance Imaging of Liver Micrometastasis in Mice with a Novel Liver Macromolecular Magnetic Resonance Contrast Agent DAB-Am64 (1B4M-Gd)$_{64}$" *Cancer Research* 61:4966-4970.

Kobayashi, H. et al. 2001 "Micro-MR Angiography of Normal and Intratumoral Vessels in Mice Using Dedicated Intravascular MR Contrast Agents with High Generation of Polyamidoamine Dendrimer Core: Reference to Pharmacokinetic Properties of Dendrimer-Based MR Contrast Agents" *Journal of Magnetic Resonance Imaging* 14:705-713.

Kobayashi, H. et al. 2001 "Positive Effects of Polyethylene Glycol Conjugation to Generation-4 Polyamidoamine Dendrimers as Macromolecular MR Contrast Agents" *Magnetic Resonance in Medicine* 46:781-788.

Kojima, C. et al. 2000 "Synthesis of Polyamidoamine Dendrimers having Poly(ethyleneglycol) Grafts and their Ability to Encapsulate Anticancer Drugs" *Bioconjugate Chem.* 11(6):910-917.

Kono et al., "Design of Dendritic Macromolecules Containing Folate or Methotrexate Residues," in Bioconjugate Chem., 1999, 10, 1115-1121.

Lee, C. et al. 2006 "A single dose od doxorubicin-functionalized bow-tie dendrimer cures mice bearing C-26 colon carcinomas" *Proc Natl Aced Sci USA* 103(45):16649-16654.

Liu, et al., Water Soluble Dendrimer-Poly(ethylene glycol) Starlike Conjugates as Potential Drug Carriers, Journal of Polymer Science Part A: Polymer Chemistry, vol. 37, Mar. 25, 1999, pp. 3492-3503.

Majaros et al., "PAMAM Dendrimer-Bases Multifunctional Conugate for Cancer Therapy: Synthesis, Characterization, and Funtionality," in Biomacromolecules, 2006, 7, 572-579.

Malik, N. et al. 2000 "Dendrimers: Relationship between structure and biocompatibility in vitro, and preliminary studies on the biodistribution of $^{125}$I-labelled polyamidoamine dendrimers in vivio" *Journal of Controlled Release* 65:133-148.

Margerum, L. et al. 1997 "Gadolinium (III) DO3A macrocycles and polyethylene glycol coupled to dendrimers: Effect of molecular weight on physical and biological properties of macromolecular magnetic resonance imaging contrasts agents" *Journal of Alloys and Compounds* 249:185-190.

McCarthy T.D. et al. 2005 "Dendrimers as Drugs: Discovery and Preclinical and Clinical Development of Dendrimer-Based Microbicides for HIV and STI Prevention" *Molecular Pharmaceutics* 2(4):312-318.

Mullen, et al., "A Quantitative Assessment of Nanoparticle_Ligand Distributions: Implications for Targeted Drug and Imaging Delivery in Dendrimer Conjugates", American Chemical Society, 2010, vol. 4, No. 2, pp. 657-670.

Okuda, T. et al. 2006 "PEGylated lysine dendrimers for tumor-selective targeting after intravenous injection in tumor-bearing mice" *Journal of Controlled Release* 116:330-336.

Sakthivel, T. et al. 1999 "Distribution of a lipidic 2.5 nm diameter dendrimer carrier after oral administration" *International Journal of Pharmaceutics* 183:51-55.

Tajarobi, F. et al. 2001 "Transport of poly amidoamine dendrimers across Madin-Darby canine kidney cells" *International Journal of Pharmaceutics* 215:263-267.

Wiwattanapatapee, R. et al. 2000 "Anionic PAMAM Dendrimers Rapidly Cross Adult Rat Intestine In Vitro: A Potential Oral Delivery System?" *Pharmaceutical Research* 17(8):991-998.

* cited by examiner

Structure A - BHALys [Lys]$_8$ [NH$_2$]$_{16}$

Structure B - BHALys [Lys]$_{16}$ [NH$_2$]$_{32}$ 1  ((((AA)(AA))⁴((AA)(AA))⁴)⁸(((AA)(AA))⁴((AA)(AA))⁴)⁸)¹⁶
   ((((BB)(BB))⁴((BB)(BB))⁴)⁸(((BB)(BB))⁴((BB)(BB))⁴)⁸)¹⁶

2  ((((AA)(AA))⁴((AA)(AA))⁴)⁸(((BB)(BB))⁴((BB)(BB))⁴)⁸)¹⁶
   ((((AA)(AA))⁴((AA)(AA))⁴)⁸(((BB)(BB))⁴((BB)(BB))⁴)⁸)¹⁶

3  ((((AA)(AA))⁴((BB)(BB))⁴)⁸(((AA)(AA))⁴((BB)(BB))⁴)⁸)¹⁶
   ((((AA)(AA))⁴((BB)(BB))⁴)⁸(((AA)(AA))⁴((BB)(BB))⁴)⁸)¹⁶

4  ((((AA)(BB))⁴((AA)(BB))⁴)⁸(((AA)(BB))⁴((AA)(BB))⁴)⁸)¹⁶
   ((((AA)(BB))⁴((AA)(BB))⁴)⁸(((AA)(BB))⁴((AA)(BB))⁴)⁸)¹⁶

5  ((((AB)(AB))⁴((AB)(AB))⁴)⁸(((AB)(AB))⁴((AB)(AB))⁴)⁸)¹⁶
   ((((AB)(AB))⁴((AB)(AB))⁴)⁸(((AB)(AB))⁴((AB)(AB))⁴)⁸)¹⁶

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial
<220> FEATURE:
<221> NAME/KEY: SOURCE
<222> LOCATION: 1..4
<223> OTHER INFORMATION: /mol_type="protein"
      /note="peptide linker"
      /organism="Artificial"

<400> SEQUENCE: 1

Gly Gly Gly Phe
1
```

MODIFIED MACROMOLECULE

FIELD OF THE INVENTION

The present invention relates to macromolecules, production thereof and their use, particularly dendrimers, whose surface architecture may be controlled to produce an enriched proportion of a topological isomer. In particular, the macromolecules may have two or more surface groups, wherein at least one of the surface groups is pharmaceutically active.

BACKGROUND OF THE INVENTION

Identification of new compounds for use in pharmaceutical preparations is an important part of the search for more reliable and effective therapies. However just as important is the development and modification of known compounds, reducing the risks associated with a new drug candidate and significantly reducing the development and cost to bring the drug to clinical development.

Many drugs fail in clinical trials either because their physical properties (particularly solubility) make them difficult to formulate, or because of a poor therapeutic index that leads to toxic effects during the high drug concentrations that occur just after dosing. Other short comings include poor absorption, poor bioavailability, instability, systemic side effects due to an inability to target the drugs, and the inability to control their biodistribution, metabolism and renal or hepatic clearance once administered. Similarly some current products on the market can be improved with regards to such issues.

A number of approaches have been tried to improve a pharmaceutical compound's profile including the formulation of the pharmaceutical agent in a liposome, micellar or polymeric micelle formulation, as well as covalent attachment of the pharmaceutical agent to a hydrophilic polymer backbone.

The characteristics of an ideal profile modifying agent include being a well defined structure, allowing precise control of the absorption, distribution, metabolism and excretion (ADME) characteristics (also referred to as pharmacokinetics) of the compound in question and advantageously being able to carry multiple compounds per agent or construct. The toxicity of a compound in question can be ameliorated through its controlled release from the said agent or construct, the body only being exposed to therapeutic plasma concentrations of the compound.

In recent years, dendritic macromolecules have been found to have increasing applications in biotechnology and pharmaceutical applications. Dendritic macromolecules are a special class of polymers with densely branched structures that are characterized by higher concentrations of functional groups per unit of molecular volume than ordinary polymers. There are four subclasses of macromolecules: random hyperbranched polymers; dendrigraft polymers; dendritic motifs; and dendrimers, classified on the basis of the relative degree of structural control present in each of the dendritic architectures. The unique properties of dendrimers in particular, such as their high degree of branching, multivalency, globular architecture and well-defined molecular weight, make them promising new scaffolds for drug delivery. In the past decade, research has increased on the design and synthesis of biocompatible dendrimers and their application to many areas of bioscience including drug delivery.

The potential utility of dendritic polymers both as drug delivery vectors and pharmaceutical actives has received increasing interest in recent years[1,18]. However, whilst the literature is replete with reports of, for example, synthetic schemes for dendrimer assembly, descriptions of dendrimer-drug interactions and drug loading efficiencies and, increasingly, in vitro evaluations of dendrimer interactions with cell lines[2,3], there is very little information describing the fundamental pharmacokinetic and metabolic fate of dendrimers.

The interaction of dendrimers with intestinal tissues has also been the subject of several studies[4-11] and whilst trends in permeability and cytotoxicity with surface charge and surface functionality have been established, relatively few studies have described the fate of dendrimers once absorbed into the systemic circulation. Of these few studies, Gillies et al. have examined the pharmacokinetics of PEGylated, 'bow-tie' polyester dendrimers and shown that dendrimer clearance mechanisms are highly dependent on the molecular weight and flexibility of the complex,[12] Kobayashi et al. have examined the effect of structural changes on the biodistribution of dendrimers designed to facilitate heavy metal or antibody complexation (and therefore application in bio-imaging)[13-17]. To this point, however, the intrinsic systemic pharmacokinetics of polylysine dendrimers have not been described in any detail.

Further, it is still a challenge to prepare dendrimers that circulate in the blood long enough to accumulate at target sites, but that can also be eliminated from the body at a reasonable rate to avoid long-term build up. In addition, the tissue localisation of dendrimers is still difficult to predict in advance and more studies are required to determine the effect of peripheral dendritic groups on these properties. An additional area that needs to be investigated is the release of drugs from dendrimers. Steric hindrance associated with the dense globular dendritic architecture makes the engineering of the enzymatically cleavable linkages difficult.

It is, accordingly, an object of the present invention to overcome or at least alleviate one or more of the difficulties and/or deficiencies related to the prior art.

SUMMARY OF THE INVENTION

In a first aspect, the present invention provides a macromolecule having a controlled terminal group stoichiometry, the macromolecule including a surface layer, at least one subsurface layer and at least two terminal groups including:
  a first terminal group which is a residue of a pharmaceutically active agent, a derivative thereof or precursor therefor; and
  a second terminal group selected to modify the pharmacokinetics of the pharmaceutically active agent and/or macromolecule,
wherein terminal group stoichiometry refers to the number and type of terminal groups.

In a further embodiment, the macromolecule further exhibits controlled topology, wherein topology describes the relationship between one terminal group and another in terms of its connection to the surface or subsurface layers of the macromolecule.

In a preferred embodiment the second terminal group may include polyethylene glycol (PEG) or polyethyloxazoline (e.g. PEOX).

In a further embodiment, the second terminal group is selected from one or more of the following: a moiety that modifies the plasma half life of the pharmaceutically active agent and/or macromolecule; a moiety that facilitates the targeting of the pharmaceutically active agent and/or macromolecule to one or more cell or tissue types; and a moiety that facilitates the uptake of the pharmaceutically active agent and/or macromolecule into one or more cell or tissue types.

In a preferred embodiment, the second terminal group is selected to prolong the half-life of the pharmaceutically active agent and/or macromolecule.

The macromolecule is a preferably a dendrimer, more preferably a lysine dendrimer.

The macromolecules according to this aspect of the invention may be utilised in various applications, as discussed below, where the ability to control the terminal group stoichiometry and/or topology is advantageous in providing a consistent pharmacokinetic profile for the pharmaceutically active agent.

DETAILED DESCRIPTION OF THE INVENTION

As used herein in this specification and claims, the singular forms "a", "an" and "the" include plural referents unless the context clearly dictates otherwise. Thus, for example, reference to a "a macromolecule" includes one or more such macromolecules.

By the term "comprises" (or its grammatical variants) as used herein in this specification and claims is equivalent to the term "includes" and should not be taken as excluding the presence of other elements or features.

By the term "topology" as used herein in the specification and claims, we mean the relationship between one terminal group and another in terms of their connection to the surface and subsurface layers.

By the term "topological isomer" as used herein in the specification and claims we mean a macromolecule having a particular topology.

By the term "surface" as used herein in the specification and claims we mean the layer of generation-building units bearing surface amines reactable with a "terminal group" or "capping" group.

By the term "subsurface" as used herein in the specification and claims we mean the layer/layers below the surface layer.

By the term "surface amine" as used herein in the specification and claims we mean any surface reactable amine group of the dendrimer.

By the term "terminal group stoichiometry" as used herein in the specification and claims we mean the composition (number and type) of the terminal groups on the surface of the macromolecule.

By the term "generation-building unit" as used herein in the specification and claims we mean the repeating unit that forms the framework of the dendrimer, for example a lysine or lysine analogue in the case of a lysine dendrimer.

By the term "dendritic motif" as used herein in the specification and claims we mean a discrete segment of the macromolecule. When one of the macromolecule branches is cleaved at the bond which connects one of the reactable amines of the generation-building unit or core to the carboxyl of the attached generation-building unit, the dendritic motif will be released. The carboxyl of the dendritic motif represents the unique point, or apex, at which the dendritic motif would be attached to a growing macromolecule core during the process of synthesising a macromolecule of the invention.

Any macromolecule may be suitable for use in the present invention. The macromolecule may be selected from one or more dendritic polymers including arborols, dendrigrafts, PAMAM dendrimers, lysine dendrimers and the like.

The preparation of dendrimer polymers is well known, and is described by way of example in U.S. Pat. Nos. 4,289,872 and 4,410,688 (describing dendrimer polymers based on layers of lysine units), as well as U.S. Pat. Nos. 4,507,466, 4,558,120, 4,568,737 and 4,587,329 (describing dendrimer polymers based on other units including polyamidoamine or PAMAM dendrimer polymers). The dendrimer polymers disclosed in these US patents are described as being suitable for uses such as surface modifying agents, metal chelating agents, demulsifiers or oil/water emulsions, wet strength agents in the manufacture of paper, and agents for modifying viscosity in aqueous formulations such as paints. It is also suggested in U.S. Pat. Nos. 4,289,872 and 4,410,688 that the dendrimer polymers based on lysine units may be used as substrates for the preparation of pharmaceutical dosages.

The present invention will now be described in more detail with reference to dendrimers. In particular, those based on polylysine.

One key determinant of a dendrimer's efficacy in any given application is the nature of the macromolecule surface. The applicants have surprisingly discovered techniques to modify the absorption, distribution, metabolism and excretion (ADME) profile of certain pharmaceutical compounds by conjugating them to dendrimers in a well defined and controlled process. More particularly dendrimer size and/or surface functionality may be modified to adjust excretion (clearance), distribution and metabolism (absorption and resorption) profiles of the drug. The process of the present invention may allow the production of precise structures which may be varied to meet the specific needs of the drug. Furthermore there is the ability to attach multiple molecules to a dendrimer in a controlled fashion, allowing a higher drug load and more versatile therapy. The drug loading may further be modified by varying the generation number of the dendrimer.

Previous studies have suggested that after intravenous administration, uncapped $^3$H labelled poly-L-lysine dendrimers are rapidly metabolised to free lysine. However, it has surprisingly been established that PEGylation of the dendrimer reduces the recognition of the dendrimer by proteolytic enzymes as well as serum proteins and suppresses the phagocytic clearance, thereby prolonging plasma circulation times. Furthermore, PEGylation may increase the hydrodynamic volume of the dendrimer, thereby reducing the renal clearance rate.

For example, the present inventors have found that the plasma half-life and extent of urinary elimination of $^3$H labelled PEGylated lysine dendrimers is dependent on molecular weight. Larger PEGylated dendrimers (i.e. >30 kD) were relatively slowly cleared from the plasma into the urine compared with smaller dendrimers (i.e. <20 kD). This is despite the fact that the smaller dendrimer complexes showed signs of interaction with plasma components, leading to the creation of a higher molecular weight species. Elimination of these complexes was rapid and only intact dendrimer was recovered in the urine. Furthermore the present inventors have observed that where pharmaceutically active components and PEG groups are attached to the surface of a dendrimer, the size of the PEG group attached to the dendrimer surface may determine whether the dendrimer is able to avoid uptake by the reticuloendothelial system. It is therefore apparent that adding size by any means does not necessarily result in prolonged plasma life of the dendrimers. The larger dendrimers were found to accumulate in the liver and spleen. However this occurred over extended time periods and the amount that accumulated was less than 10% of the dose.

In a further preferred embodiment, the PEG or polyethyloxazoline terminal groups may constitute approximately 25% to 75% of the terminal groups on the dendrimer, more preferably approximately 25% to 50%. The relative size of the individual PEG or polyethyloxazoline groups may be increased to maintain the required plasma life time and avoid liver uptake. The percentage of PEG or polyethyloxazoline groups and/or the size of the PEG or polyethyloxazoline group may be modified and tailored to suit different pharmaceutically active agents.

In a preferred embodiment, the PEG groups are relatively monodisperse and chosen from a molecular weight range between 200 and 10,000 Daltons, more preferably the PEG groups are chosen from a molecular weight range between 500 and 5,000 Daltons.

PEGylation may also improve the solubility of compounds and therefore may assist the solubility of an otherwise insoluble drug conjugated to the surface of the dendrimer.

The present invention thus provides a means by which drugs with high toxicity, or poor solubility, or both, may be engineered to provide a vehicle that will provide a controlled release of the drug to maintain a long term drug concentration at therapeutic, but not toxic, plasma levels.

Dendrimers carrying two different terminal groups may be prepared as different topological isomers, where topology describes the relationship between one terminal group and another in terms of its connection to the surface and subsurface layers. Dendrimers carrying two or more different terminal groups are described in AU 2005905908 the entire disclosure of which is incorporated by reference. The way in which each topological isomer interacts with a complex system may be different. Therefore it may be advantageous to be able to control the surface distribution of different terminal groups for different applications.

The capacity to enrich a dendritic macromolecule sample in molecules of the same topology may be desirable in the same way it has been shown to be desirable to enrich organic materials in particular stereoisomers, particularly for biological applications. Thus one topological isomer in the macromolecule may be more effective in a given application than another topological isomer.

Prior art methods for producing a dendrimer having two or more different terminal groups involve synthesis using random surface functionalisation methods.

In a first prior art approach, a substoichiometric amount of the first active terminal group is used in an attempt to cap only half the reactive terminal amine moieties on the surface of the macromolecule (surface amines). The remaining surface amines may then be reacted, and in this second reaction, an excess of the second active terminal group may be used to force the reaction to completion. In this approach, there is a statistical distribution of products with varying terminal group stoichiometries arising from the first stage of the reaction, and furthermore there is little or no control over the topology of the two different terminal groups.

Similarly, in a second prior art approach, both terminal groups may be simultaneously reacted with the reactive surface amine moieties. In such an approach, it may be possible to adjust the stoichiometries of each terminal group to account for their differing reactivities, but molecule to molecule variability will still arise because more than one type of generation-building unit or more than one terminal group is available to react with the deprotected nitrogen groups and so the likely outcome of each reaction may only be described by a statistical distribution, and again, there is be no control over the topological outcome of the reaction.

In comparison to the random surface functionalisation of the prior art, a macromolecule is considered "enriched" if the fractional abundance of dendritic moieties with precisely specified terminal groups is greater than their fractional abundance in a randomly surface functionalised material by a factor of at least 2 (2 fold monodispersity) and preferably 4 (4 fold monodispersity). The concept of enrichment which has been illustrated for terminal groups may also be applied to surface couplets, quartets and octets etc, which are described in detail in AU2005905908, the entire contents of which is incorporated herein by reference. A macromolecule may be enriched for a particular terminal group stoichiometry and/or topology.

At the extreme level of enrichment of terminal group stoichiometry, each macromolecule will have the same composition (number and type) of terminal groups. At a more moderate level of enrichment, eg enrichment at 20%, this is taken to mean that 20% of the macromolecules will have the same composition (number and type) of terminal groups.

Alternatively this enrichment may be specified by comparing a composition with a randomly functionalised macromolecule composition. For example, if the random method provides a particular surface composition in 5% of the macromolecules, enrichment would constitute an increase in the macromolecule with a particular terminal group composition (number and type) over this 5% level. Therefore, a two fold enrichment would mean that 10% of the macromolecules exhibited the particular terminal group composition.

The simplest type of topological enrichment is enrichment at the level of couplets. A dendrimer composition may be fully enriched at the level of terminal groups, but not fully enriched at the level of couplets. This is because the same terminal groups may be grouped into couplets in a number of ways. For example in all FIGS. 9.1 to 9.5 the dendrimer contains 16 terminal A groups and 16 terminal B groups. However in FIGS. 9.1 to 9.4 there are eight (AA) couplets and eight (BB) couplets while in FIG. 9.5 there are sixteen (AB) couplets. A higher order of topological enrichment is enrichment at the level of quartets, octets and 16-tets, and is explained in detail in AU2005905908.

In another aspect there is provided a macromolecule including at least one lysine or lysine analogue dendritic motif having a surface layer and at least one subsurface layer, the macromolecule including at least two terminal groups including:
  a first terminal group which is a residue of a pharmaceutically active agent, a derivative thereof or precursor therefor; and
  a second terminal group selected to modify the pharmacokinetics of the pharmaceutically active agent and/or macromolecule,
wherein terminal group stoichiometry refers to the number and type of terminal groups.

In a further embodiment of this aspect of the invention, the macromolecule further exhibits controlled topology, wherein topology describes the relationship between one terminal group and another in terms of its connection to the surface or subsurface layers of the macromolecule.

In a preferred embodiment the second terminal group may include a polyethylene glycol (PEG) or polyethyloxazoline (e.g. PEOX) motif.

In a further embodiment, the second terminal group is selected to modify the plasma half-life of the pharmaceutically active agent. In a preferred embodiment, the second terminal group is selected to prolong the half-life of the pharmaceutically active agent.

In a further embodiment, the second terminal group is selected to facilitate the targeting and/or uptake of the pharmaceutically active agent to one or more cell or tissue types.

In another aspect of the present invention, there is provided a dendrimer having controlled capping group stoichiometry and having the formula:

$$\text{Core[Repeating Unit]}_m\text{[Surface Building Unit]}_n\text{[Capping Group 1]}_p\text{[Capping Group 2]}_q$$

wherein:
the core is selected from the group consisting of lysine, or a derivative thereof, a diamine compound, a triamine compound or a tetramine compound;
the Repeating Unit is selected from the group consisting of an amidoamine, a lysine or lysine analogue;
the Surface Building Unit may be the same as or different to that of the building unit and is selected from an amidoamine, a lysine or lysine analogue;
Capping Group 1 is a pharmaceutically active agent, derivative thereof, precursor therefore or residue thereof;
Capping Group 2 is selected to modify the pharmacokinetics of the pharmaceutically active agent;
m represents the sum of the Repeating Units of the subsurface layer or layers of the dendrimer and is and integer between 1 and 32;
n represents the number of Surface Building Units of the surface layer or layers of the dendrimer and is an integer between 2 and 32;
p represents the number of Capping Group 1 groups and is an integer between 1 and 64; and
q represents the number of Capping Group 2 groups and is an integer between 1 and 64.
wherein capping group stoichiometry refers to the number and type of capping groups.

The core of the dendrimer polymer may be selected from any suitable compound. Preferably, the core is selected from lysine, or a derivative thereof, a diamine compound, a triamine compound, or a tetraamine compound. Most preferably, the core is benzhydrylamido-lysine (BHALys), or a compound selected from the following:

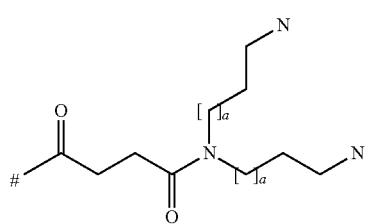

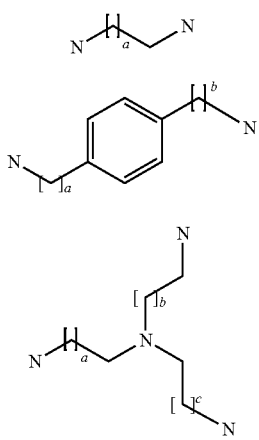

wherein each of a, b, and c is an integer of between 0 and 5, more preferably 1 to 3.

The repeating unit according to this embodiment of the present invention may preferably be selected from one or more of

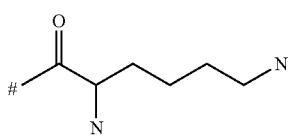

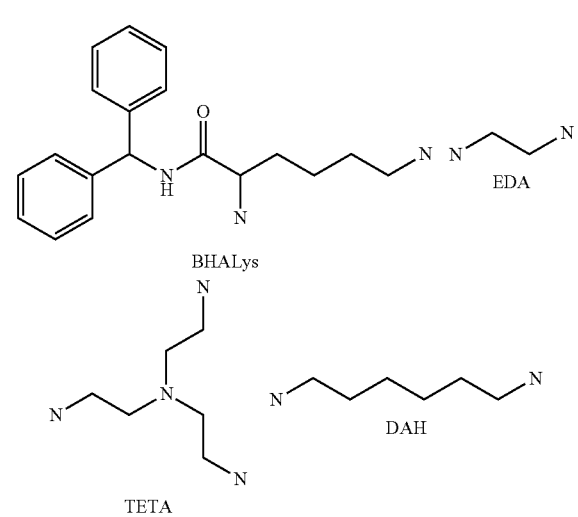

wherein a is either 0 or 1, preferably 1.

In a preferred aspect of the present invention, the dendrimer has a lysine or lysine analogue core. The lysine dendritic core may be selected from the group consisting of BHALys, DAH, EDA and TETA, as represented by the following:

The dendrimer may be a PAMAM polymer, e.g. PAMAM$_{32}$, a lysine or lysine analogue polymer wherein the repeating unit is [Lys]$_Q$ or [Su(NPN)$_2$]$_Q$ wherein Q is an integer of 2, 6, 14, 30 or 62 on a divalent core or 3, 9, 21 or 45 on a trivalent core.

The dendrimer according to the present invention may extend through as many generations as is required. Preferably, the dendrimer extends through 1 to 5, more preferably 1 to 3, generations.

The pharmaceutically active agent of the macromolecule (particularly dendrimer) according to the present invention may include a water-insoluble pharmaceutical, a water-soluble pharmaceutical, a lipophilic pharmaceutical, or mixtures thereof.

The pharmaceutically active agent may be exemplified by, but not limited to one or more selected from the groups in Table 1.

TABLE 1

| | |
|---|---|
| Acetonemia preparations | Anabolic agents |
| Anaesthetics | Analgesics |
| Anti-acid agents | Anti-arthritic agents |
| Antibodies | Anti-convulsants |
| Anti-fungals | Anti-histamines |
| Anti-infectives | Anti-inflammatories |
| Anti-metabolites | Anti-microbials |
| Anti-mitotics | Anti-parasitic agents |

TABLE 1-continued

| | |
|---|---|
| Anti-protozoals | Anti-ulcer agents |
| Antiviral Pharmaceuticals | Behaviour modification drugs |
| Biologicals | Blood and blood substitutes |
| Bronchodilators and expectorants | Cancer therapy and related pharmaceuticals |
| Cardiovascular pharmaceuticals | Central nervous system pharmaceuticals |
| Contrast agents | Contraceptives |
| Diuretics | Diabetes therapies |
| Growth hormones | Fertility pharmaceuticals |
| Hematinics | Growth promoters |
| Hormone replacement therapies | Hemostatics |
| Immune suppressives | Immunostimulants |
| Hormones and analogs | Muscle relaxants |
| Minerals | Natural products |
| Nutraceuticals and nutritionals | Obesity therapeutics |
| Ophthalmic pharmaceuticals | Osteoporosis drugs |
| Pain therapeutics | Peptides and polypeptides |
| Respiratory pharmaceuticals | Sedatives and tranquilizers |
| Transplantation products | Urinary acidifiers |
| Vaccines and adjuvants | Vitamins |

The present invention is particularly appropriate for pharmaceuticals that are very active even in extremely small quantities and whose sustained long-term administration is sought, particularly to overcome toxicity problems with standard doses. Non-limiting examples include methotrexate, an anti-metabolite, taxol, an anti-mitotic, zenical, an obesity therapeutic, cyclosporine, an immunosuppressive and indomethacin, an antiinflammatory therapeutic.

In one embodiment, the macromolecule according to the present invention includes two or more different pharmaceutically active agents, derivatives thereof, precursors therefore, or residues thereof, as terminal groups.

In a further aspect, the present invention provides a dendrimer having a controlled terminal group stoichiometry and including:
   at least two terminal groups which are residues of different pharmaceutically active agents, derivatives thereof or precursors therefor; and
   a further terminal group selected to modify the pharmacokinetics of the pharmaceutically active agent and/or dendrimer,
wherein terminal group stoichiometry refers to the number and type of terminal groups The dendrimers according to this aspect of the present invention may have application in combination therapy.

The pharmaceutically active agents may be a combination of any two or more of the categories exemplified in Table 1. Exemplary combinations include, but are not limited to, combinations of: chemotherapeutic pharmaceuticals; anti-inflammatory pharmaceuticals and anti-arthritic pharmaceuticals; obesity therapeutics and diabetes therapeutics; growth hormones and growth promoters; muscle relaxants and anti-inflammatories; respiratory pharmaceuticals and bronchodilators or anti-microbials; chemotherapeutics and vitamins and the like. More specific combinations are described in the examples.

The macromolecules, in particular dendrimers, according to the present invention may be particularly useful in facilitating the passive targeting of drugs to solid tumours and to sites of inflammation. This targeting is possible because of the increased permeability of vasculature associated with tumours and with inflammation, to macromolecules and because of limited lymphatic drainage.

The macromolecules according to the present invention may also be targeted to a particular cell type or tissues types using targeting moieties present on the dendrimer.

Accordingly, in a further aspect of the present invention there is provided a dendrimer having a controlled terminal group stoichiometry and including:
   a first terminal group which is a residue of a pharmaceutically active agent, a derivative thereof or precursor therefor; and
   a second terminal group which is a targeting moiety for targeting the pharmaceutically active agent and/or macromolecule to one or more specific cell or tissue types,
wherein terminal group stoichiometry refers to the number and type of terminal groups.

Examples of suitable targeting moieties include lectins, antibodies and functional fragments of antibodies. Targeting moieties may also include ligands for cell surface receptors.

A number of different cell surface receptors are useful as targets for the binding and/or uptake of macromolecules. In particular, receptors and their related ligands that are useful in the present invention include, but are not limited to, the folate receptor, adrenergic receptor, growth hormone receptor, luteinizing hormone receptor, estrogen receptor, epidermal growth factor receptor, fibroblast growth factor receptor (eg FGR2), IL-2 receptor, CFTR and vascular epithelial growth factor receptor.

In a further aspect of the invention there is provided a macromolecule having a controlled terminal group stoichiometry, the macromolecule including a surface layer, at least one subsurface layer and at least two terminal groups, including:
   a first terminal group which is a residue of a pharmaceutically active agent, derivative thereof or precursor therefor; and
   a second terminal group which is capable of functioning as a cellular receptor ligand,
wherein terminal group stoichiometry refers to the number and type of terminal groups.

In a further aspect of the present invention there is provided a macromolecule having a controlled terminal group stoichiometry, the macromolecule including a surface layer, at least one subsurface layer and at least two terminal groups including:
   a first terminal group which is a residue of a pharmaceutically active agent, a derivative thereof or precursor therefor; and
   a second terminal group which is which is capable of functioning as a cellular receptor,
wherein terminal group stoichiometry refers to the number and type of terminal groups.

Folate is a vitamin that is essential for the biosynthesis of nucleotide bases and is therefore required in high amounts in proliferating cells. In cancer cells, this increased requirement for folic acid is frequently reflected in an over-expression of the folate receptor which is responsible for the transport of folate across the cell membrane. In contrast, the uptake of folate into normal cells is facilitated by the reduced folate carrier, rather than the folate receptor. The folate receptor is upregulated in many human cancers, including malignancies of the ovary, brain, kidney, breast, myeloid cells and the lung and the density of folate receptors on the cell surface appears to increase as the cancer develops.

The relative specificity of the folate receptor to tumour cells, and in particular to advanced stage tumour cells, mean that the folate receptor ligand, folate, may be a useful candidate for targeting chemotherapeutic drugs to tumours. The specificity is of the folate receptor interaction with a folate receptor ligand-chemotherapeutic drug conjugate is further enhanced by the difference in the cell surface expression pattern of the folate receptor between certain non-transformed and malignantly transformed epithelial cells. In non-transformed cells, the folate receptor is preferentially expressed on the apical membrane surface of the cells, which faces the body cavity and is inaccessible to reagents present in the blood. However, upon transformation, the cell loses its polarity and the receptor can become accessible to drugs in the circulatory system that are targeted to the folate receptor. Accordingly, folate or a folate derivative may be a useful targeting moiety of the macromolecule of the present invention.

In further aspect of the present invention there is provided a macromolecule, having a controlled terminal group stoichiometry, the macromolecule having two or more different terminal groups including
- a first terminal group which is a residue of a pharmaceutically active agent; a derivative thereof or precursor therefor; and
- a second terminal group which is a residue of folate or a folate analogue, wherein terminal group stoichiometry refers to the number and type of terminal groups.

In a preferred embodiment of this aspect of the present invention the pharmaceutically active agent is an anti-tumour pharmaceutical agent. A cytotoxic agent, cytokine, anti-angiogenic agent, anti-mytotic agent, or the like, or any combination thereof may be used.

In a preferred embodiment, the pharmaceutically active agent is selected from one or more of methotrexate, taxol, cisplatin, carboplatin and doxorubicin.

Linker moieties may be incorporated into the synthesis of a dendrimer according to the present invention, for example by substitution for a generation-building unit, or to mediate the attachment of a terminal group to a generation building unit.

Accordingly, in further aspect of the present invention there is provided a macromolecule, preferably a dendrimer, having a controlled terminal group stoichiometry, the macromolecule having two or more different terminal groups including
- one or more linker moieties;
- a first terminal group which is a residue of a pharmaceutically active agent; a derivative thereof or precursor therefor; and
- a second terminal group selected to modify the pharmacokinetics of the pharmaceutically active agent and/or macromolecule;

wherein the first and/or second terminal groups are attached to the macromolecule framework by the linker moieties; and wherein terminal group stoichiometry refers to the number and type of terminal groups.

In a further embodiment, the second terminal group is selected from a moiety that facilitates the targeting of the pharmaceutically active agent and/or macromolecule to one or more cell or tissue types and a moiety that facilitates the uptake of the pharmaceutically active agent and/or macromolecule into one or more cell or tissue types, and one or more linker moieties including PEG.

The linker may be cleavable or non cleavable, depending on the requirements of the group(s) attached to the surface. Cleavable linkers may be designed to be enzymatically cleaved, and may for example, be used in dendrimers targeted to tissues expressing those enzymes. Alternatively, an acid labile linker may be preferred such that the compound attached to it is released under acid conditions, such as in hypoxic tissue.

Summary of Various Linkers

The linker moiety may be selected from one or more of the following:

| Linker type | Summary |
| --- | --- |
| Amide | Generally used as stable linkers. |
| Hydrazone | Acid labile linkers that are mostly stable at physiological pH have been shown to inhibit the growth of some tumour cells after hydrolysis of the bond to release an anti-tumour drug. |
| Oxime | Acid labile linkers that are mostly stable at physiological pH have been shown to inhibit the growth of some tumour cells after hydrolysis of the bond to release an anti-tumour drug |
| Imine | Acid labile linkers that are mostly stable at physiological pH have been shown to inhibit the growth of some tumour cells after hydrolysis of the bond to release an anti-tumour drug |
| Ester | The cleavability of esters are strongly related to their structure and number or cleavable sites, where monoesters are more stable that diesters. In general, esters are less stable than amide bonds and more stable than disulfide bonds. Cleavage of orthoesters are dependent on acidic pH. |
| Peptide | A large number of peptide bonds have been investigated as generally non specific enzyme cleavable linkers. Their stability depends largely on the molecules they are attached to and the sequence. |
| Glutaraldehyde | Used as a cross linking agent only to stabilise bonds between drug and carrier, particularly in gel formulations. |
| PEG-peptide | PEG groups are used to improve the pharmacokinetics and toxicity of an antibody carrier while the peptide group links the surface of the PEG to the drug. |
| disulfide | One of the most unstable linkers available and shows poor stability in circulation. Generally used to facilitate rapid metabolism of toxic species/carriers in target organs. |
| thymidine | While this has not previously been used as a metabolisable linker, thymidine phosphorylase is over expressed in many solid tumours and catalyses the phosphoralytic cleavage of thymidine to thymine and deoxyridose-1-phosphate. |

Amide Linkers (19-21)

The nature of an amide bond is important in determining whether the free drug will be released from a conjugate. For instance, conjugation of a drug (ie doxorubicin) to a carrier via an amide bond produces a conjugate that is hydrolytically stable and which does not exert any anticancer effects in vitro. A drug bound directly to a carrier via an amide bond will also not be readily cleaved as a free drug, but rather as a drug-amino acid if the carrier is itself degradable. The release of free drug from carriers bound via a direct amide linker will only be achievable in rare circumstances where the drug is itself a peptide-like molecule and the bond between drug and carrier is enzymatically cleavable.

Hydrazone, Oxime and Imine Linkers (21-25)

Hydrazone, oxime and imine bonds do not require the presence of enzymes to allow cleavage of the drug from the carrier. They are able to be cleaved hydrolytically at the C=N bond in low pH environments such as in the tumour extravascular space or within lysosomes. Commonly used hydrazone, oxime and imine linkers arise from the reaction of a hydrazine, alkoxyamine or amine moieties, respectively, of a linker with a carbonyl (ketone or aldehyde) of a pharmaceutically active moiety. The link may also be modified to slow the rate of hydrolysis by modifying the number of alkyl groups surrounding the C=N bond moiety, or by substitution with electron withdrawing (to increase acid lability) or electron donating (to decrease acid lability) moieties.

Ester Linkers (19, 26)

Both acid labile and metabolisable ester linkers can be made. Orthoesters have been used to conjugate PEG to lipids which bind anionic membrane carriers. The stability of the conjugate in acidic conditions (pH 4-6) depends on the structure of the ester or orthoester linker. In general, $\alpha$-methoxy-$\omega$-{N-(2-octadecyloxy-[1,3]dioxolan-4-yl)methylamido}-polyethyleneglycol$_{110}$ shows good stability at both pH 4 and 5, $\alpha$-methoxy-$\omega$-{N-(2-cholesteryloxy-[1,3]dioxolan-4-yl)methylamido}-polyethyleneglycol$_{110}$ is very stable at pH 5 but moderately less stable at pH 4, $\alpha$-methoxy-$\omega$-{N-(2-methyl-s-octadecyloxy-[1,3]dioxan-5-yl)-amido}-polyethyleneglycol$_{110}$ and $\alpha$-methoxy-$\omega$-{N2-(3-hydroxypropyl-cholesterylcarbamate)-2-methyl[1,3]dioxan-5-yl-amido}-polyethyleneglycol$_{110}$ are not stable. In terms of simple ester conjugation to small molecules, diester functionalities provide more sites for metabolic cleavage compared with monoesters which are more stable than disulfides but less stable than amide bonds.

Peptide Linkers (27-33)

Peptide linkers are by far the most versatile of all cleavable linkers in that many different combinations of amino acids can be used to control the rate of cleavage and the cleavage enzyme. However, these linkers have two problems associated with their use as conjugates for drug and carrier, 1) they are generally cleavable by non specific peptidases throughout the body and may therefore result in non-specific drug toxicity at non-tumour distribution sites and 2) cleavage may occur at a site within the linker that results in an amino acid remaining bound to the drug molecule. This may hinder the chemotherapeutic effect of the drug molecule. Alternatively, the bound amino acid may not alter the pharmacological effects of the drug but may affect its pharmacokinetics. However, these cleavage effects may be controlled by choosing an appropriate amino acid in the peptide linker that is bound directly to the drug molecule, e.g. proline.

Generally, cathepsin B cleavable linkers have been designed to be cleaved following endocytosis of the drug conjugate via the lysosome system, as cathepsin is located in lysosomes and not free in the cytosol. Endocytosis is generally initiated following binding of the carrier (which is usually an antibody directed against a cancer specific cell surface receptor or ligand for a cancer specific cell surface receptor) to the cell membrane.

Non-specific proteases (ie. proteases that are not specific for a particular peptide sequence) may cleave a drug from a PEGylated dendrimer after it has undergone sufficient extravasation and accumulation in tumour tissue.

The following guidelines about the rate of peptide cleavage apply, where a>b indicates that the rate of cleavage of a is greater than the rate of cleavage for b. For peptide sequences used as linkers between an active pharmaceutical and the dendrimer terminal nitrogens: terminal CG>no terminal CG>terminal G=terminal GFG>terminal GGG and terminal GGGF=terminal GPG.

Note: CG bonds are reduced by GSH. GGG bonds are generally very stable relative to other peptide bonds. The cleavage of dipeptides are generally specific to particular proteases and may be controlled based on the expression of various proteases contained within tumour cells.

Glutaraldehyde (34, 35)

Glutaraldehyde is generally not used as a conventional linker but is used as a stabilising agent especially in gel formulations or to covalently attach a drug to a desired adsorption surface. It is also used as a non-metabolisable spacer, creating a gap between drug molecules and large carriers via cross linking reactions.

PEG-Peptide (2, 36)

PEG-peptides are used in a similar way to conventional peptides, except the PEG moiety provides additional in vivo stability and mass for the carrier. Typically, it is used to conjugate drug to antibody carriers and has the advantage of increasing the distance between Ab and drug while exposing the site of enzymatic cleavage, decrease immunogenicity of the conjugate, increase blood circulation times and increasing the solubility of the complex. Following internalisation of the conjugate and enzymatic release of the active drug (which is not necessarily released as free drug) antiproliferative effects have been observed for Adriamycin and a Duocarmycin derivative.

Disulfide Linkers (1, 37, 38)

Disulfide linkers are the most unstable linkers currently used and undergo rapid reductive cleavage in vitro. Their in vivo stability is generally higher, however, than their in vitro stability. They may be formed via disulfide linkages between sulphur containing amino acids or at non peptide based disulfide bonds. They also show greater reactivity with other nucleophilic thiols in the body and hence show rapid plasma clearance.

General Summary of Linker Cleavability

In circulation, the order of linker cleavabilities is as follows:

Disulfide>long chained peptides≥esters>hydrazones≥tetrapeptides (GGGF)=tripeptides (GFG>GGG=GPG) ≈ or > dipeptides (AV, AP, GP, FL, V-Cit)> glutaraldehyde=amide.

Linker Recommendations

The stability of various linkers is based on the groups to which they are conjugated (ie accessibility of the enzymes to the linker), the behaviour of the conjugate at the site of required activity (ie. cellular uptake or extracellular accumulation) and the nature of the conjugate (ie. ester vs amide). The in vivo behaviour of the disulfide conjugates with the current system is expected to be relatively unpredictable. While long chained peptides are more easily assessed by proteases for rapid cleavage, they may be cleaved too rapidly and at non specific sites, resulting in release of a pharmaceutical active-peptide/amino acid species which may not be biologically active.

Cleavage of a C=N based linker (hydrazone, oxime or imine), ester or peptide conjugates will occur at least over several days which allows the conjugates to accumulate in tumour tissue. Each has its advantages, but ester or hydrazone linkers may be preferred. An ester bond linking a pharmaceutical active to the dendrimer provides a bond that is rapidly cleaved, and though this may not be specific to the target site, cleavage results in the release of free a pharmaceutical active. Hydrazone bonds produce conjugates are more stable in the general circulation than esters and are cleaved with greater specificity at the tumour site via hydrolysis at the C=N bond. However, the pharmaceutical active molecule may need be modified to allow hydrazone formation either by incorporation of a carbonyl or hydrazine moiety.

In a preferred embodiment, the linker moiety may include two reactive functional groups, F and Y, which are connected by one or more carbons or heteroatoms, preferably by a hydrocarbon backbone. The functional group F may be activated to react with reactive amine moieties like those on the surface of the dendrimer. Typically the functional group F is a carboxylate group or residue thereof. The other functional group, Y, is either an amine comprising a protecting group, or it is selected such that it has a specific reactivity that is complementary to a reactive group of a desired organic radical that is to be attached to the surface of a dendritic motif. Typical examples of Y include amine, hydroxyl, thiol, alkenyl or alkynyl, nitrile, halide, carboxylate or azido groups.

Where linker moieties are used to connect terminal groups to the surface amine groups of the dendrimers, the reaction between the linker and the organic radical may be carried out either before, or after, the linker moiety is reacted with the surface amine of the dendritic motif. A reaction which is used to introduce one or more linker moieties to a dendritic motif is conducted to ensure the complete reaction of all deprotected surface amines of a dendrimer with the linker moieties. Typically this is done by using an excess of the chosen linker moiety.

In addition to the linkers described above, photocleavable linkers may be used with the present invention. For example, heterobifunctional, photocleavable linkers may be used. Heterobifunctional, photocleavable linkers may be either water or organic soluble. They contain an activated ester that may react with amines or alcohols and an epoxide that may react with a thiol group. Between the ester and epoxide groups is a 3,4-dimethoxy-6-nitrophenyl photoisomerisation group, which, when exposed to near-ultraviolet light (365 nm), releases the amine or alcohol in intact form. Thus, the pharmaceutically active component, when linked to the dendrimer using such linkers, may be released in biologically active or activatable form through exposure of the target area to near-ultraviolet light.

For example, the alcohol group of taxol may be reacted with the activated ester of an organic-soluble linker. This product in turn is reacted with a partially-thiolated surface of a dendrimer. In the case of cisplatin, the amino groups of the drug may be reacted with a water-soluble form of the linker. If the amino groups do not have the required activity, a primary amino-containing active analogue of cisplatin, such as Pt(II) sulfadiazine dichloride may be used. Thus conjugated, the drug is inactive and will not harm normal cells. When the conjugate is localized within tumour cells, it is exposed to laser light of the appropriate near-UV wavelength, causing the active drug to be released into the cell.

In a further aspect of the present invention, there is provided a pharmaceutical composition including a macromolecule having a controlled terminal group stoichiometry the macromolecule having a surface layer, at least one subsurface layer and two or more different terminal groups and including
    a first terminal group which is a residue of a pharmaceutically active agent; a derivative thereof or precursor therefor;
    a second terminal group selected to modify the pharmacokinetics of the pharmaceutically active agent and/or macromolecule; and
    a pharmaceutically acceptable carrier, diluent or excipient therefor.

The macromolecule component may be a dendrimer, preferably a lysine dendrimer.

The pharmaceutically active agent may be selected from one or more of the categories of pharmaceutically active agents described above. Preferably the pharmaceutically active agent is a cancer therapy or related pharmaceutical including anti-mitotic or anti-metabolite agent; an obesity therapeutic agent; an anti-inflammatory agent; or an immunosuppressive agent.

The second terminal group may be selected to prolong the plasma half-life of the pharmaceutical active. In a further embodiment, the second terminal group is selected to facilitate the targeting and/or uptake of the pharmaceutically active agent to one or more specific cell or tissue types.

The second terminal group may include a polyethylene glycol (PEG) or polyethyloxazoline (e.g. PEOX) motif.

In a further aspect of the present invention there is provided a pharmaceutical composition including a macromolecule having a controlled terminal group stoichiometry the macromolecule having a surface layer, at least one subsurface layer and two or more different terminal groups including:
    a first terminal group which is a residue of a pharmaceutically active agent; a derivative thereof or precursor therefor;
    a second terminal group which is a residue of folate or a folate analogue; and
    a pharmaceutically acceptable carrier, diluent or excipient therefor.
wherein terminal group stoichiometry refers to the number and type of terminal groups.

In a preferred embodiment of this aspect of the present invention the pharmaceutically active agent is an anti-tumour pharmaceutical agent. A cytotoxic agent, cytokine, anti-angiogenic agent, anti-mytotic agent, or the like, or any combination thereof may be used.

The antitumor pharmaceutical agent may be selected from one or more of the following:
    rituximab, oxaliplatin, docetaxel, gemcitabine, trastuzumab, irinotecan, paclitaxel, bevacizumab, carboplatin, cetuximab, doxorubicin, pemetrexed, epirubicin, bortezomib, topotecan, azacitidine, vinorelbine, mitoxantrone, fludarabine, doxorubicin, alemtuzumab, carmustine, ifosfamide, idarubicin, mitomycin, fluorouracil, cisplatin, methotrexate, melphalan, arsenic, denileukin diftitox, cytarabine, calcium levofolinate, cyclophosphamide, etoposide, *viscum album*, mesna, gemtuzumab, ozogamicin, busulfan, pentostatin, cladribine, bleomycin, daunorubicin, bendamustine, dacarbazine, raltitrexed, vincristine, fotemustine, etoposide phosphate, porfimer sodium and vinblastine.

In a preferred embodiment, the pharmaceutically active agent is selected from one or more of methotrexate, taxol, cisplatin, carboplatin and doxorubicin.

The pharmaceutically acceptable carriers or excipients may be selected from any known carriers or excipients depending on the delivery route selected for the active.

The pharmaceutical composition may be formulated for oral, injectable, rectal, parenteral, subcutaneous, intravenous, intramuscular or other delivery. The pharmaceutical composition may be formulated in tablet, capsule, caplet, injectable ampoule vial, or ready-to-use solution, lyophilised material, suppository, bolus or implant form.

The formulation of such compositions is well known to persons skilled in the art. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences,* 18th Edition, Mack Publishing Company, Pennsylvania, USA. Except insofar as any conventional media or agent is incompatible with the terminal groups of the dendrimer polymer described herein, use thereof in the pharmaceutical compositions of the present invention is contemplated. Supplementary active ingredients may also be incorporated into the compositions.

It is especially advantageous to formulate compositions in dosage unit form for ease of administration and uniformity of dosage. "Dosage unit form" as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In yet another aspect of the present invention there is provided use of an effective amount of a macromolecule as described above in the prophylactic or therapeutic treatment of, or in the manufacture of a medicament for treatment of a human or non-human animal patient.

In a still further aspect of the present invention there is provided a method for the treatment of a disease indicator or physiological deficiency in a mammalian, including human, patient, which method includes administering to a patient requiring such treatment, a prophylactically or therapeutically effective amount of a pharmaceutical composition, as described above.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, inhalation, transdermal or parenteral (e.g. subcutaneous, intramuscular and intravenous), intraocular and intravitreal (ie, into the eye's vitreous) routes. Formulations for oral administration include discrete units such as capsules, tablets, lozenges and the like. Other routes include intrathecal administration directly into spinal fluid, direct introduction such as by various catheter and balloon angioplasty devices well known to those of ordinary skill in the art, and intraparenchymal injection into targeted areas.

The compositions may conveniently be presented in unit dosage form and may be prepared by any of the methods well known in the art of pharmacy. Such methods include the step of bringing the active compound into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the macromolecule, in liposomes or as a suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol. Among the acceptable vehicles and solvents that may be employed are water, and isotonic sodium chloride solution. In addition, sterile, fixed oils are conventionally employed as a solvent or suspending medium. For this purpose, any bland fixed oil may be employed including synthetic mono-or diglycerides. In addition, fatty acids such as oleic acid find use in the preparation of injectables The macromolecule of the present invention may also be formulated for delivery in a system designed to administer the dendrimer polymer intranasally or by inhalation, for example as a finely dispersed aerosol spray containing the active component.

Other delivery systems may include sustained release delivery systems. Preferred sustained release delivery systems are those which may provide for release of the macromolecule of the present invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, a pump-based hardware delivery system may be used, some of which are adapted for implantation.

The macromolecule of the present invention is administered in prophylactically or therapeutically effective amounts. A prophylactically or therapeutically effective amount means that amount necessary to at least partly attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and may be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily doses of the macromolecule may be from about 0.01 mg/kg per day to 1000 mg/kg per day. Small doses (0.01-1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

In a further preferred embodiment, pharmaceutically acceptable carriers or excipients may be selected from one or more of sterile aqueous salt solutions, suspensions and emulsions, including saline and buffered media, Ringer's dextrose, dextrose and sodium chloride, and lactated Ringer's solution. Intravenous vehicles include fluid and nutrient replenishers, electrolyte replenishers, such as those based on Ringer's dextrose, and the like. For administration by non-intravenous routes, the carrier can be in the form of clotted plasma, preferably the patient's clotted plasma. Alternatively the carrier can be a plasma-free, physiologically compatible, biodegradable solid or semi-solid, such as a gel, suspension or water soluble jelly. *Acacia*, methylcellulose and other cellulose derivatives, sodium alginate and tragacanth suspensions or gels are suitable for use as carriers in the practice of this invention, for example, sodium carboxymethylcellulose 2.5%, tragacanth 1.25% and guar gum 0.5%.

In a further preferred embodiment, the macromolecule in the pharmaceutical composition may include at least two different terminal groups which are pharmaceutically active.

Such embodiments may be utilised in combination therapies of various types.

In a further preferred embodiment, the pharmaceutical composition includes
- a macromolecule, preferably a dendrimer, having a controlled terminal group stoichiometry, the macromolecule including at least two terminal groups including:
- at least one cleavable or non-cleavable linker moiety;
- a first terminal group which is a residue of a pharmaceutically active agent; a derivative thereof or precursor therefor;
- a second terminal group selected to modify the pharmacokinetics of the pharmaceutically active agent and/or macromolecule; and
- a pharmaceutically acceptable carrier, diluent or excipient therefor, wherein the first and/or second terminal groups are attached to the macromolecule framework by the one or more linker moieties; and
wherein terminal group stoichiometry refers to the number and type of terminal groups.

Cancerous tumours will grow rapidly and uncontrollably to an approximate diameter of 2 mm before the lack of effective nutrient supply to the interior of the tumour limits further cellular replication (1). A tumour may remain this size for many years until angiogenesis is initiated to supply the tumour with its own blood supply. One mechanism by which this may occur is via the activation of hypoxia inducible factor-1α, which is a transcription factor that is upregulated at sites of limited oxygen and glucose supply (such as the interior of tumour masses) and which is responsible for the upregulation of genes involved in angiogenesis (2). However, the rapid vascularisation within a tumour creates defective architecture with large gaps between vascular endothelial cells that allow accumulation of large particles that are normally not permeable through normal vasculature. In addition, lymphatic drainage is not created within a tumour mass to remove accumulated particles, hence the existence of the tumour EPR effect (1).

The irregular metabolism and vascular supply within tumours creates a different pH gradient compared with normal cells. The increased accumulation of lactate and carbonic acid within a tumour results in a slightly acidic extracellular environment (pH~6.5) while the intracellular environment is neutral or slightly alkaline (pH 7.0-7.4) due to defective Na/H exchangers. This differential pH gradient hinders the accumulation of some chemotherapeutics which are weak bases, for example doxorubicin. The acidic extracellular environment has also been linked to cancer metastases due to the degradation of the interstitial matrix and intercellular gap junctions.

It is possible to exploit this extracellular acidity to enable pH mediated release of anticancer drugs from carrier molecules which have been bound via an acid labile linker. Release may occur in the extracellular space (pH~6.5) or the lysosomal compartment (pH~4-5). Anticancer drugs have also been linked to tumour targeting groups such as transferrin the receptor for which is over-expressed by most tumour cells. Other linkers have been used which are cleavable by cathepsins B or D which are over expressed in tumour lysosomes.

Accordingly in a further aspect of the present invention, there is provided a method for the treatment of a tumour, including a malignant tumour, in a mammalian, including human, patient requiring such treatment, which method includes
administering to the patient an effective amount of
- a pharmaceutical composition including a macromolecule having a controlled terminal group stoichiometry, the macromolecule including a surface layer, at least one subsurface layer and at least two terminal groups including:
- a first terminal group which is a residue of an anti-tumour pharmaceutical agent; a derivative thereof or precursor therefor;
- a second terminal group selected to modify the pharmacokinetics of the anti-tumour pharmaceutical agent and/or macromolecule; and
- a pharmaceutically acceptable carrier, diluent or excipient therefor wherein terminal group stoichiometry refers to the number and type of terminal groups.

In one embodiment, the macromolecule further includes one or more linker moieties, wherein the one or more linker moieties attach the first and/or second terminal groups to the macromolecule framework.

The anti-tumour pharmaceutical agent may be of any suitable type. A cytotoxic agent, cytokine, anti-angiogenic agent, anti-mytotic agent, or the like, or any combination thereof may be used.

The antitumor agent may be selected from one or more of the following:
rituximab, oxaliplatin, docetaxel, gemcitabine, trastuzumab, irinotecan, paclitaxel, bevacizumab, carboplatin, cetuximab, doxorubicin, pemetrexed, epirubicin, bortezomib, topotecan, azacitidine, vinorelbine, mitoxantrone, fludarabine, doxorubicin, alemtuzumab, carmustine, ifosfamide, idarubicin, mitomycin, fluorouracil, cisplatin, methotrexate, melphalan, arsenic, denileukin diftitox, cytarabine, calcium levofolinate, cyclophosphamide, etoposide, *viscum album*, mesna, gemtuzumab, ozogamicin, busulfan, pentostatin, cladribine, bleomycin, daunorubicin, bendamustine, dacarbazine, raltitrexed, vincristine, fotemustine, etoposide phosphate, porfimer sodium and vinblastine.

In a preferred embodiment, the anti-tumour pharmaceutical agent is selected from one or more of methotrexate, taxol, cisplatin, carboplatin and doxorubicin.

The second terminal group may be selected to prolong the plasma half-life of the pharmaceutical active. The second terminal group may be selected to facilitate the targeting and/or uptake of the anti-tumour pharmaceutical agent to one or more specific cell or tissue types. In a preferred embodiment, the second terminal group includes a polyethylene glycol (PEG) or polyethyloxazoline.

The pharmaceutically acceptable carriers or excipients may be selected from any known carriers or excipients depending on the delivery route selected for the active.

The macromolecules, in particular dendrimers of the present invention may be used to target pharmaceutically active agents to the lymphatic system.

The lymphatic system consists of an elaborate network of specialised vessels, nodes and areas of aggregated lymphoid tissue, distributed throughout the vascular regions of the body. The lymphatics are primarily responsible for the maintenance of fluid balance, but also play a role in the intestinal absorption and transport of neutral fats and in the maintenance of an effective immune defence mechanism. In most capillary beds, the vascular endothelium is continuous and associated with an uninterrupted basement membrane. As such vascular capillaries are relatively poorly permeable to large molecules and small particulates that are injected into the interstitial space (eg after subcutaneous or intramuscular injection). In contrast, lymphatic capillaries consist of a single layer of overlapping endothelial cells with an incomplete basal lamina. This results in an endothelial layer with more 'open' intercellular junctions than those in blood capillaries. Estimates of intercellular junctional distances range from several microns (3-5) to 15 to 20 nm (6-10). These large intercellular junctions may therefore facilitate the preferential transport or drainage of macromolecules, colloids and potentially dendrimers from the interstitial spaces into the lymphatics.

In terms of directed or targeted delivery to the lymphatics, the lymph also serves as a primary conduit for the dissemination of tumour metastases and has been widely explored as a target for cytotoxic agents designed to combat the spread of metastases from solid tumours. The relatively high concentrations of B and T lymphocytes in the lymph also provide attractive targets for cytokines such as interferon and immunomodulators in general. Furthermore, recent findings in human immunodeficiency virus (HIV) positive patients of increased viral burden and increased viral propagation in lymphoid tissue has heightened interest in the lymph as a therapeutic target in the treatment of HIV and AIDS. To date, several liposomal formulations have been developed that provide targeted delivery of drugs to lymph nodes, particularly for the anti-cancer drug doxorubicin (Doxil/Caelyx)(16-21).

Accordingly, in a further aspect of the invention there is provided a method for the targeted delivery of a pharmaceutically active agent to the lymphatic system of an animal including administering to the animal an effective amount of
a macromolecule having a controlled terminal group stoichiometry, the macromolecule having a surface layer, at least one subsurface layer and at least two terminal groups including:
a first terminal group which is a residue of a pharmaceutically active agent; a derivative thereof or precursor therefor;
a second terminal group selected to facilitate the uptake of the pharmaceutically active agent and/or macromolecule to the lymph; and
a pharmaceutically acceptable carrier, diluent or excipient therefor.

In a preferred embodiment the second terminal group is PEG or polyethyloxazoline. In a preferred embodiment, the PEG groups are relatively monodisperse and chosen from a molecular weight range between 200 and 10,000 Daltons, more preferably the PEG groups are chosen from a molecular weight range between 500 and 5,000 Daltons. In a further preferred embodiment, the second terminal group is PEG having a molecular weight of greater than about 1000 Daltons. In a further preferred embodiment, the second terminal group is a PEG motif having a molecular weight of greater than about 1500 Daltons.

In a preferred embodiment, the dendrimer has a molecular weight of greater than about 20 kDa, preferably greater than about 30 kDa, more preferably greater than about 50 kDa.

In a preferred embodiment, the dendrimer includes a cleavable or non-cleavable linker moiety which attaches the first terminal group to the dendrimer framework.

In a preferred embodiment, the dendrimer is administered to the animal, including a human, by subcutaneous injection.

Synthesis of Macromolecules

In a further aspect the present invention provides a method of manufacturing a macromolecule having a controlled terminal group stoichiometry, the macromolecule including a surface layer, at least one subsurface layer and two or more different terminal groups, wherein at least one terminal group which is a pharmaceutically active agent, a derivative thereof, precursor therefor, or residue thereof and at least one terminal group is selected to modify the pharmacokinetics of the pharmaceutically active agent, where terminal group stoichiometry refers to the number and type of terminal groups.

The process for synthesising dendrimers of the present invention involves the sequential reaction of a growing dendrimeric core moiety and one or more layers of lysines or lysine analogues as generation-building compounds. The apex carboxylate F of the lysine analogues, which represents the unique point at which the dendritic motif is be attached to a growing macromolecule core during the process of synthesis, will necessarily be activated prior to reaction with an unprotected amine moiety. Each of the amine groups A and B of the lysine analogue is protected to prevent self condensation. Amines A and B of the generation-building compounds are always protected when carboxylate F of a generation-building compound is reacted with unprotected nitrogens of a growing dendrimer. Furthermore the reaction between unprotected amines and activated lysine analogues is always carried out in such a way so as to ensure that the unprotected amines are completely reacted with the chosen lysine analogue. This is most simply done by using a stoichiometric excess of the activated lysine analogue.

The process for synthesising dendrimers of this invention may include the reaction of unprotected amines of a growing dendrimer with linker groups or terminal groups such as pharmaceutical actives, cell surface ligands, and PEG. In each case, the carboxylate group of the linker or terminal group is activated for amide bond formation either prior to the reaction or in situ. The amine of the linker group is protected or has been reacted already with a terminal group. Furthermore, the reaction between unprotected amines of the growing dendrimer and the activated linkers or terminal groups is carried out in such a way as to ensure that the unprotected amines are completely reacted with the activated group, typically by using the activated group in excess.

The order of removal of protecting groups may be an important factor in determining the sequence of reactions that may be used to prepare dendrimers comprising different amine protecting groups, particularly in those cases where the cleavage conditions for one amine protecting group may lead to the loss of a spectator amine protecting group. The protecting group table below provides the preferred set of resolvable, and orthogonal, amine protecting groups.

A set of resolvable amine protecting groups are defined as those for which an order of removal exists such that those groups that are not meant for cleavage are inert to the cleavage conditions. When protecting groups are defined as orthogonal, this means that each group is inert to the cleavage conditions required to remove each of the other groups of the orthogonal set. Illustrative amine protecting groups may be sourced in the following references: Protective groups in Organic Synthesis, 3$^{rd}$ Edition, John Wiley and Sons, New York 1999, Greene, T. W. and Wuts, P.G.M., Protecting Groups 3$^{rd}$ Edition, Thieme Stuttgart 2004, Kocienski, P. J. Preferred amine protecting groups may be selected from Table 2.

TABLE 2

Preferred Amine Protecting Groups

| Protecting Group[1] | Boc | CBz/NCBz | Fmoc | 2-halo-Cbz* | Aloc | SES | Troc | Ns | DNP |
|---|---|---|---|---|---|---|---|---|---|
| Boc | | O | O | O | O | O | O | O | O |
| CBz or 4-Nitro-CBz (NCBz) | O | | R (Fmoc) | 3 | O | O | R (Troc) | R (Ns) | R (DNP) |
| Fmoc | O | R (Fmoc) | | R (Fmoc) | O | O | O | 3 | 3 |
| 2-halo-Cbz[2] | O | 3 | R (Fmoc) | | O | O | R (Troc) | R (Ns) | R (DNP) |
| Aloc | O | O | O | O | | O | O | O | O |
| Me$_3$SiEtSO$_2$ (SES) | O | O | O | O | O | | O | O | O |
| Troc | O | R (Troc) | O | R (Troc) | O | O | | O | O |
| o-NO$_2$PhSO$_2$ (Ns) | O | R (Ns) | 3 | R (Ns) | O | O | O | | 3 |
| 2,4-dinitrobenzene-sulfonyl (DNP) | O | R (DNP) | 3 | R (DNP) | O | O | O | 3 | |

Notes:
[1]The combinations of the protecting groups listed in the first column of the table with the protecting groups listed across the top row of the table are defined as being either "resolvable" (R) or "orthogonal" (O). When a combination is deemed "resolvable", the protecting group in parentheses denotes the group which should be removed first.
[2]Refers to 2-chloro-Cbz and 2-bromo-Cbz.
3. Combination neither resolvable nor orthogonal.

In a further aspect, the present invention provides a process for preparing a macromolecule having controlled terminal group stoichiometry including the steps of:
(i) providing
　a growing macromolecule including an outer layer bearing functional groups and two or more different protecting groups;
　a precursor for a first terminal group which is a residue of a pharmaceutically active agent, a derivative thereof or precursor therefor; and
　a precursor for a second terminal group selected to modify the pharmacokinetics of the pharmaceutically active agent and/or macromolecule,
(ii) deprotecting a functional group on the outer layer by removing a first protecting group;
(iii) activating one of the first or second terminal group precursors;
(iv) reacting the deprotected functional group with the activated terminal group precursor;
(v) deprotecting a functional group on the outer layer by removing a second protecting group;
(vi) activating the other of the first or second terminal group precursors; and
(iv) reacting the deprotected functional group with the activated terminal group precursor;
wherein terminal group stoichiometry refers to the number and type of terminal groups.

In a further aspect, the present invention provides a process for preparing a macromolecule having controlled terminal group stoichiometry including the steps of:
(i) providing
　a growing macromolecule including an outer layer bearing functional groups and two or more different protecting groups;
　a first terminal group precursor which is a residue of a pharmaceutically active agent, a derivative thereof or precursor therefor; and
　a second terminal group selected to modify the pharmacokinetics of the pharmaceutically active agent and/or macromolecule,
　and a linker moiety including a carboxylate group and a protected amine group
(ii) deprotecting a functional group on the outer layer by removing a first protecting group;
(iii) activating the carboxylate group on the linker moiety;
(iv) reacting the deprotected functional group with the activated carboxylate group on the linker moiety;
(v) deprotecting the amine group on the linker moiety;
(vi) activating one of the first or second terminal group precursors;
(vii) reacting the deprotected amine group with the activated terminal group precursor;
(viii) deprotecting a functional group on the outer layer by removing a second protecting group;
(ix) activating the other of the first or second terminal group precursors; and
(x) reacting the deprotected functional group with the activated terminal group precursor;
wherein terminal group stoichiometry refers to the number and type of terminal groups.

A preferred process for synthesising the macromolecule of the present invention includes the preliminary step of providing a surface modifier compound to be attached to the growing macromolecule. The surface modifier compound includes:
　a carboxylate group, to facilitate the attachment of the modifier compound to a growing macromolecule;

a first terminal group which is a residue of a pharmaceutically active agent, a derivative thereof or a precursor therefor; and/or a second terminal group selected to modify the pharmacokinetics of the pharmaceutically active agent and/or macromolecule.

The surface group stoichiometry (number and type) of terminal groups can be controlled through the use of a dendritic motif in which the terminal amine protecting group surface group stoichiometry and topology has been established. It has been observed that such an approach can provide dendrimers of the present invention that are of high purity.

The surface modifier compound may be prepared in any suitable manner. In one embodiment, there is provided a process for preparing a surface modifier compound which process includes:

(i) providing:
  a lysine or lysine analogue compound bearing two or more different amine protecting groups and a carboxylate group;
  a precursor for a first terminal group which is a residue of a pharmaceutically active agent, a derivative thereof or precursor therefor; and
  a precursor for a second terminal group selected to modify the pharmacokinetics of the pharmaceutically active agent and/or macromolecule;
(ii) deprotecting a first amine on the protected lysine or lysine analogue compound;
(iii) activating the first or second terminal group precursor;
(iv) reacting the activated terminal group precursor with the deprotected amine group;
(v) deprotecting a second amine on the protected lysine or lysine analogue compound;
(vi) activating the other of the first or second terminal group precursors; and
(vii) reacting the other activated terminal group precursor with the second deprotected amine group to provide a surface modifier compound.

The surface modifier compound preferably includes a lysine or lysine analogue backbone. The surface modifier compound may include a plurality of lysine or lysine analogue motifs in its backbone.

The process for synthesis of the surface modifier compound according to the present invention may include the removal of one or more terminal amine protecting groups to provide one or more reactive amine groups. These reactive amine groups are then reacted with a precursor for the first or second terminal group. The carboxylate moiety of the terminal group precursor will either be activated for amide bond formation either prior to the reaction or in situ. Furthermore, the reaction between unprotected amines of the lysine or lysine analogue backbone and the activated terminal group may be carried out in such a way as to ensure that the unprotected amines are completely reacted with the activated terminal group, typically by using the activated group in stoichiometric excess.

In one embodiment, the process for the preparation of the surface modifier compound may optionally include the protection of a selected carboxylate group prior to removal of protecting groups on terminal amines present on the lysine or lysine analogue backbone. The protecting group used for the protected carboxylate group is preferably stable to the conditions required to remove the protecting groups present on the terminal amines. Carboxylate protecting groups such as methyl or more preferably ethyl esters are suitable. Illustrative carboxylate protecting groups may be sourced in the following references: Protective groups in Organic Synthesis, 3rd Edition, John Wiley and Sons, New York 1999, Greene, T. W. and Wuts, P.G.M., Protecting Groups 3rd Edition, Thieme Stuttgart 2004, Kocienski, P. J.

Where the synthesis of the surface modifier compound requires a further deprotection step subsequent to the addition of a terminal group, it is important to take the stability of this terminal group toward subsequent reactions into consideration. In a preferred sequence of terminal group additions, the second terminal group, which is selected to modify the pharmacokinetics of the pharmaceutically active agent and/or macromolecule, is added first to the lysine or lysine analogue backbone. Furthermore, in those situations where the pharmaceutically active agent is to be attached to the lysine or lysine analogue backbone via a labile linker, it may be necessary to deprotect the selected carboxylate of the dendritic motif core prior to the reaction of the unprotected terminal amine groups of the lysine or lysine analogue backbone, and furthermore where the selected carboxylate of the lysine or lysine analogue backbone is unprotected it will be necessary for the carboxylate group of the pharmaceutically active agent-linker moiety to be activated prior to the presence of the unprotected terminal amine groups.

The process for the synthesis of the surface modifier compound may then include further removal of terminal amine protecting groups and reaction with additional terminal groups to complete the surface modification of the surface modifer compound. Where the selected carboxylate of the surface modifer compound bears a protecting group, the protected carboxylate will be deprotected either once the terminal groups have all been installed, or it will be deprotected prior to the installation of a labile linker. Once the selected carboxylate of the surface modifer compound has been deprotected, all subsequent reactions to form amide bonds between unprotected terminal amine groups and the carboxylates of terminal groups will require that the carboxylates of terminal groups be activated prior to the introduction of the surface modifer compound.

The process for synthesising a macromolecule of the present invention is then continued by the reaction of unprotected amines of a growing macromolecule with the surface modifer compound. The carboxylate moiety of the dendritic motif will either be activated for amide bond formation either prior to the reaction or in situ. In a preferred method, the carboxylate moiety of the surface modifer compound is activated in situ. This method is preferred and it is possible, through the inclusion of water or other hydroxyl donors, to limit the adventitious formation of ester bonds to the macromolecule where unmasked hydroxyl moieties are present on either the growing macromolecule core or the surface modifier compound. In one embodiment, the surface modifier compound is attached to the growing macromolecule via a linker moiety.

Accordingly, in an alternative embodiment of the present invention there is provided a process for preparing a macromolecule having controlled terminal group stoichiometry including the steps of:

(i) providing
  a growing macromolecule including an outer layer bearing functional groups and one or more protecting groups; and
  a surface modifier compound including:
    a carboxylate group
    a first terminal group which is a residue of a pharmaceutically active agent, a derivative thereof or precursor therefor; and a second terminal group selected to modify the pharmacokinetics of the pharmaceutically active agent and/or macromolecule;

(ii) activating the carboxylate group on the surface modifier compound;

(iii) deprotecting a functional group on the outer layer of the growing macromolecule by removing a protecting group; and (vii) reacting the deprotected functional group on the growing macromolecule with the activated carboxylate group on the surface modifier compound, wherein terminal group stoichiometry refers to the number and type of terminal groups.

The macromolecule of the present invention may include a unique point of attachment for either of the first or second terminal group. In this way, a macromolecule may be synthesised with a single first or second terminal group. Preferably the terminal group attached to the unique point of attachment is a second terminal group which is selected to modify the pharmacokinetics of the pharmaceutically active agent and/or macromolecule. More preferably, the second terminal group that is attached to the unique point of attachment is selected to facilitate the targeting and/or uptake of the pharmaceutically active agent to one or more cell or tissue types.

In an alternative embodiment the macromolecule of the present invention may include a selected single point of attachment for either the first or second terminal group.

There are general methods described in the art for the selective mono-protection of polyamine molecules. Such methods are described in Krapcho and Kuell Synthetic Commun. 1990 20 2559. In a preferred method dendrimers with a unique point of attachment are prepared from a di- or trivalent core wherein only one of the reactive amine moieties is protected, and with a protecting group that is inert, or orthogonal, to the conditions that are used to remove other amine protecting groups during the process by which a lysine dendrimer is constructed. It is then possible to conduct the iterative cycles of lysine condensation and amine deprotection, to build a dendrimer of 1 to 6 generations, more preferably 3 to 5 generations, and in which there exists a single terminal amine moiety that is distinguished from the other terminal amine moieties by its unique amine protecting group. This unique terminal amine represents a site at which a single selected molecule, e.g. a protein or peptide, or a targeting molecule may be attached to the dendrimer.

In a preferred form of this embodiment, there is provided a macromolecule having a controlled terminal group stoichiometry, the macromolecule including a surface layer, at least one subsurface layer and at least two terminal groups including a first terminal group which is a residue of a peptide or protein, a derivative thereof or precursor therefor, the first terminal group being attached to a single selected point of attachment on the macromolecule; and a second terminal group selected to modify the pharmacokinetics of the peptide or protein and/or macromolecule;

wherein terminal group stoichiometry refers to the number and type of terminal groups.

In a preferred method, the protecting group of the unique terminal amine moiety is removed, and the terminal amine moiety is reacted with a haloacetic acid derivative, or a maleimide derivative such as 3-maleimidopropionic acid or 4-maleimidobutyric acid under conditions where the amide bond is formed. General methods for the coupling of thiol containing peptides and proteins to such thiol active groups are described in Pierce 1989 Handbook and General Catalog and the references cited therein.

The present invention will now be more fully described with reference to the accompanying examples. It should be understood, however, that the description following is illustrative only and should not be taken in any way as a restriction on the generality of the invention described above.

IN THE FIGURES

FIG. 1A—Chemical structure of $Lys_8(NH_2)_{16}$ dendrimer $BHALys[Lys]_8[NH_2]_{16}$. Each of the 8 L-$Lys_8$ terminal lysine groups contributes 2 positive charges at physiological pH. D-Lys groups attached to the $Lys_8$ core were not radiolabelled, and hence the site of $^3H$ radiolabel was located on the $Lys_8$ layer of the $Lys_{16}$ dendrimer.

Figure 1B:
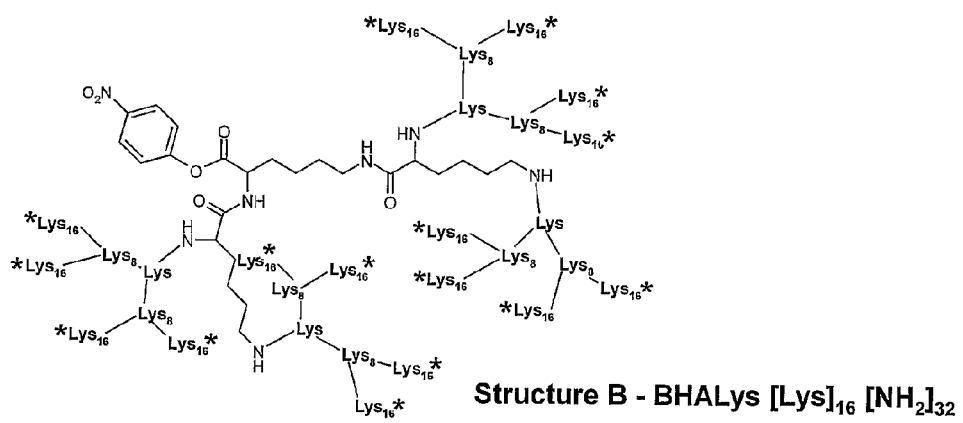

FIG. 1B—Chemical structure of L-$Lys_{16}(NH_2)_{32}$ dendrimer $BHALys[Lys]_{16}[NH_2]_{32}$. Each of the 16 L-$Lys_{16}$ terminal lysine groups contributes 2 positive charges at physiological pH. The asterisks on the terminal lysine and in the inset highlight the position of $^3H$ radiolabel on the surface lysine groups. R denotes attachment of the surface lysine to the dendrimer core.

Figure 2:
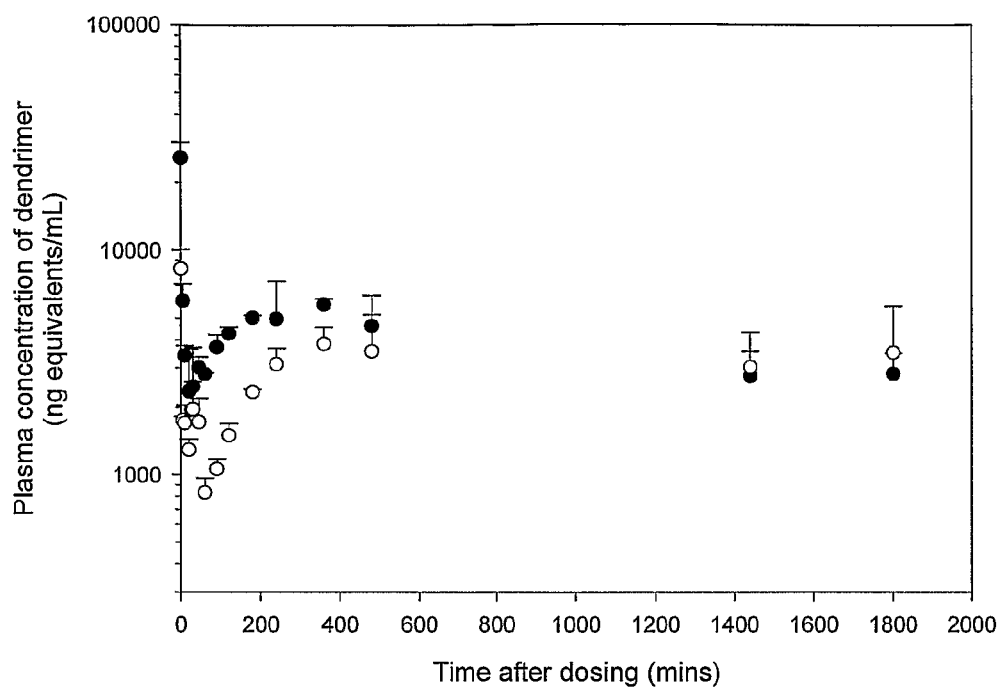

FIG. 2—Plasma concentrations of cationic $^3H$-dendrimers following intravenous administration at a dose of 5 mg/kg to rats (mean±S.D., n=3). Closed symbols represent administration of $BHALys[Lys]_8[NH_2]_{16}$, open symbols $BHALys[Lys]_{16}[NH_2]_{32}$. The data are shown as ng equivalents/ml of administered dendrimer.

Figure 3:
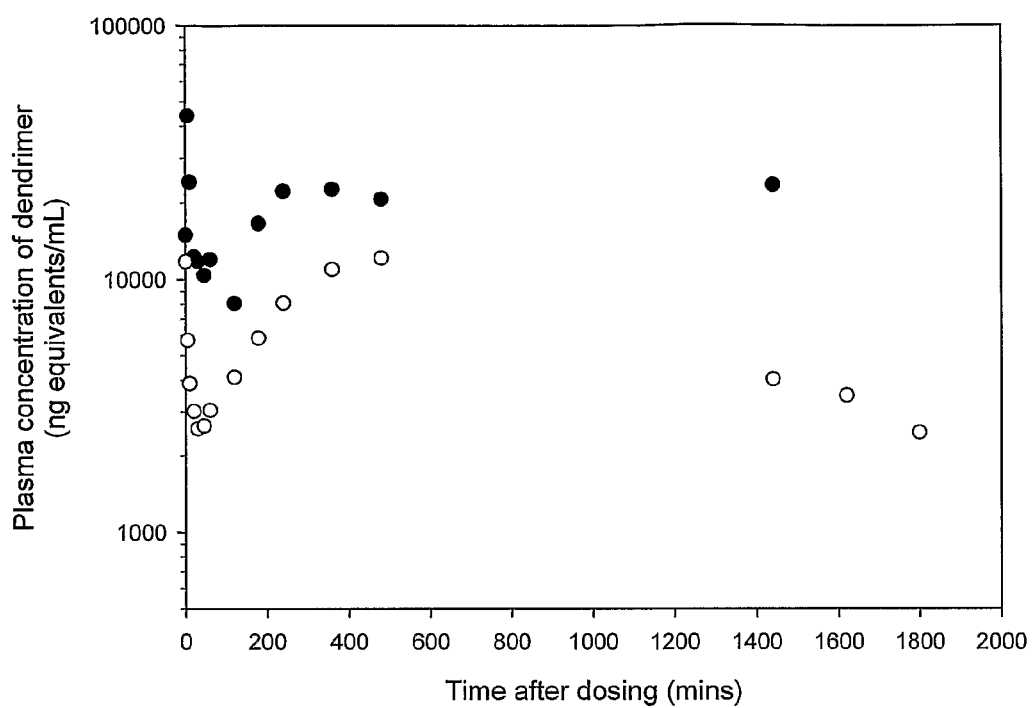

FIG. 3—Plasma concentration of cationic $^3H$-dendrimers following intravenous administration at higher doses in pilot studies to rats (n=1). Closed symbols show data obtained after administration of 24.3 mg/kg $BHALys[Lys]_8[NH_2]_{16}$ and open symbols represent data obtained after administration of 22.3 mg/kg $BHALys[Lys]_{16}[NH_2]_{32}$. The data are shown as ng equivalents/ml of administered dendrimer.

Figure 4:
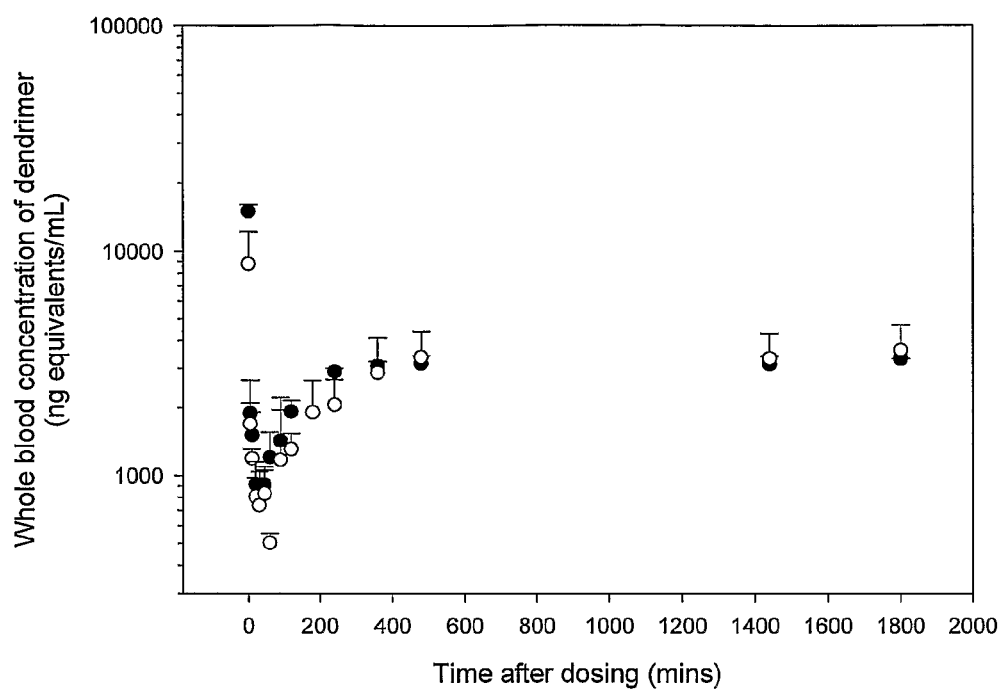

FIG. 4—Whole blood concentrations of cationic $^3H$-dendrimers following intravenous administration at a dose of 5 mg/kg to rats, (mean±S.D., n=3). Closed symbols represent administration of $BHALys[Lys]_8[NH_2]_{16}$, open symbols $BHALys[Lys]_{16}[NH_2]_{32}$. The data are shown as ng equivalents/ml of administered dendrimer.

Figure 5:
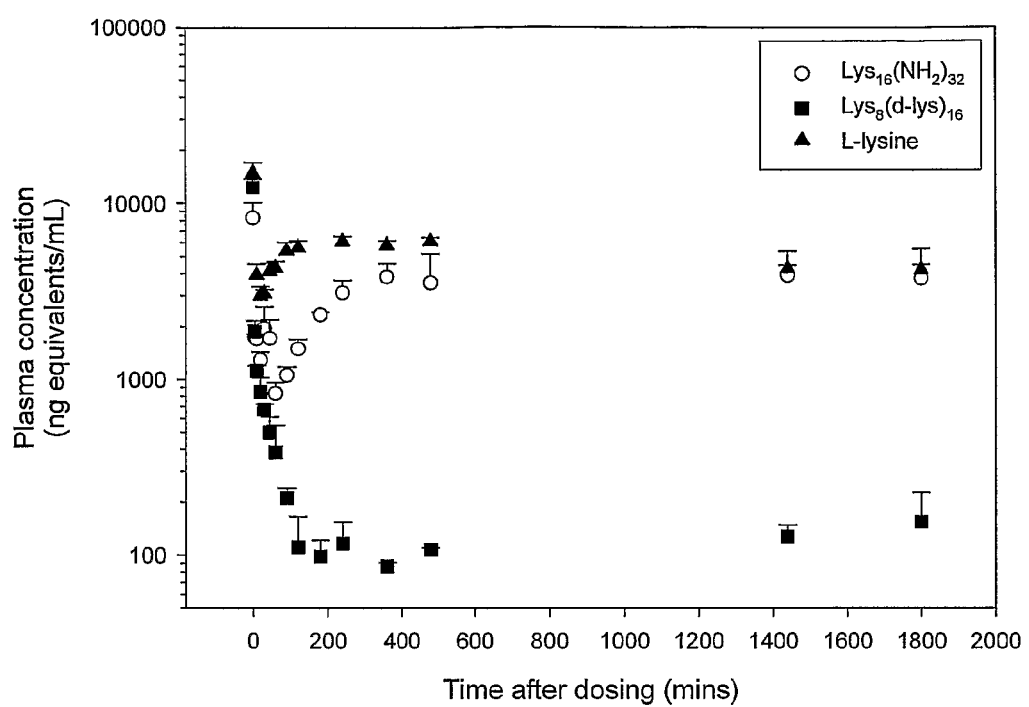

FIG. 5—Plasma concentrations of $BHALys[Lys]_{16}[NH_2]_{32}$, $BHALys[Lys]_8[D-Lys]_{16}[NH_2]_{32}$ and L-lysine following intravenous administration at 5 mg/kg to rats (mean±S.D., n=3). Closed circles represent administration of $BHALys[Lys]_{16}[NH_2]_{32}$, open circles $BHALys[Lys]_8[D-Lys]_{16}[NH_2]_{32}$ and closed triangles L-lysine. The data are shown as ng equivalents/ml of administered dendrimer or lysine.

Figure 6:
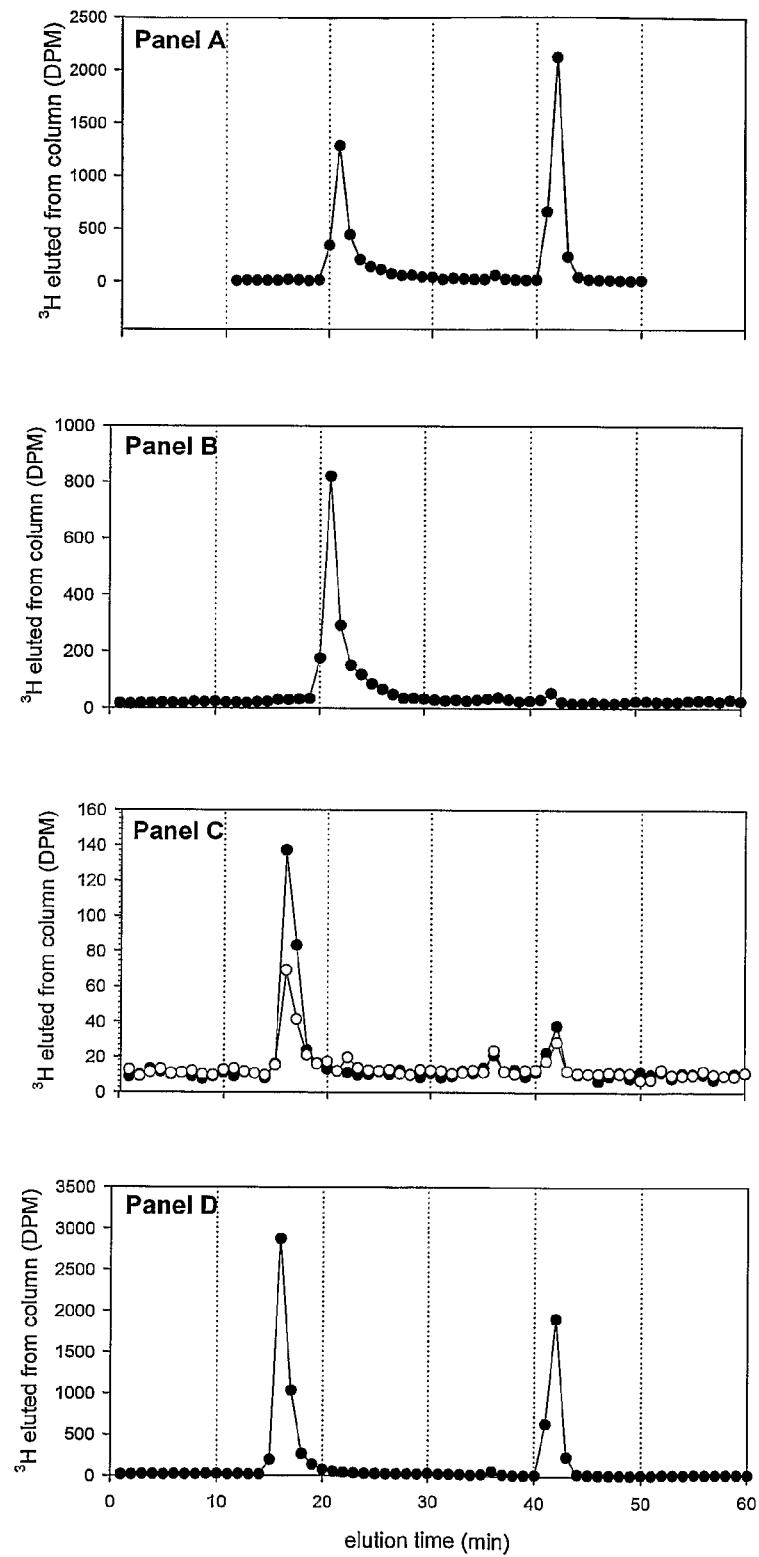

FIG. 6—Size exclusion chromatography (SEC) profiles obtained using a Superdex Peptide 10/300 GL size exclusion column. Panel A—$BHALys[Lys]_{16}[NH_2]_{32}$ and lysine after incubation in heparinised blank plasma for one hour at room temperature. The elution volumes and profiles were identical to those obtained for $BHALys[Lys]_{16}[NH_2]_{32}$ and lysine (profile not shown). Panel B—Plasma sample taken immediately (t=0) after intravenous administration of $BHALys[Lys]_{16}[NH_2]_{32}$. Panel C—Plasma samples taken 3 hr (open symbols) and 6 h (closed symbols) after intravenous administration of $BHALys[Lys]_{16}[NH_2]_{32}$. Panel D—Plasma sample taken 30 hr after intravenous administration of L-lysine.

Figure 7:
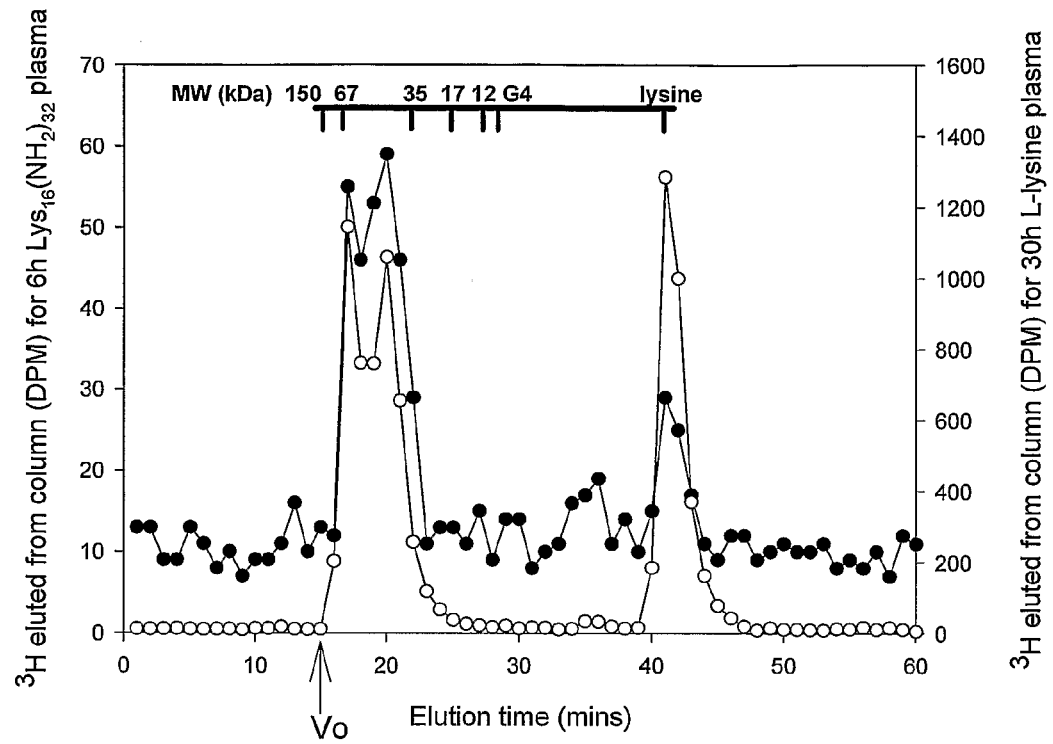

FIG. 7—Elution profiles of plasma radiolabel (as eluted DPM) from a Superdex 75 HR 10/30 size exclusion column. Closed symbols represent the elution profile for a plasma sample taken 6 hr after intravenous administration of $BHALys[Lys]_{16}[NH_2]_{32}$ (scale on left hand Y axis). Open symbols represent the elution profile for a plasma sample taken 30 hr after intravenous infusion of L-lysine (scale on right hand Y axis). The elution times for various MW protein standards, BHALys[Lys]$_{16}$[NH$_2$]$_{32}$ and lysine are shown at the top of the graph. The void volume of the column was determined by injection of blue dextran 2000 (MW 2000 kDa) and is indicated below the figure (Vo).

Figure 8:
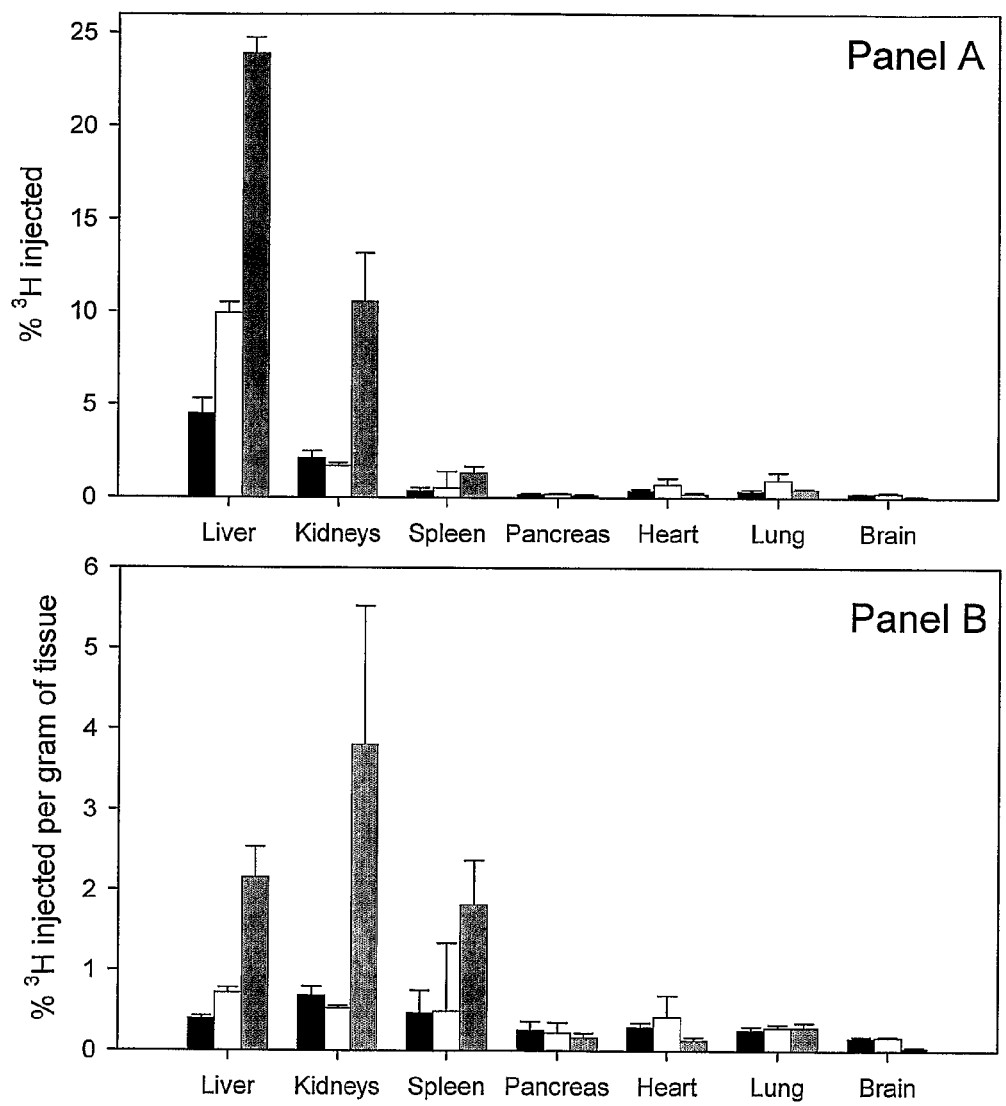

FIG. 8—Distribution of residual $^3$H in major organs at 30 hr after intravenous administration of cationic $^3$H-dendrimers at 5 mg/kg to rats. Panel A is data presented as % of injected radiolabel, while for Panel B the data is presented as % of injected radiolabel per gram of tissue (mean±S.D., n=3). Closed symbols represent the tissue biodistribution for BHALys[Lys]$_8$[NH$_2$]$_{16}$, while open symbols represent the tissue biodistribution for BHALys[Lys]$_{16}$[NH$_2$]$_{32}$. Shaded (grey) symbols represent the tissue biodistribution for BHALys[Lys]$_8$[D-Lys]$_{16}$[NH$_2$]$_{32}$.

Figure 9:
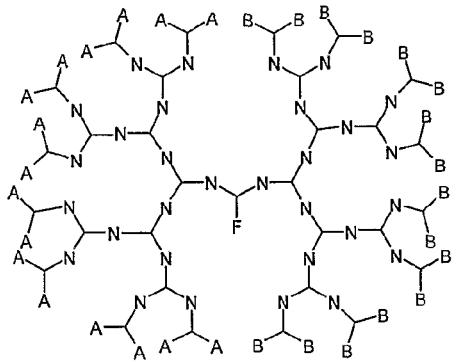
Figure 9:
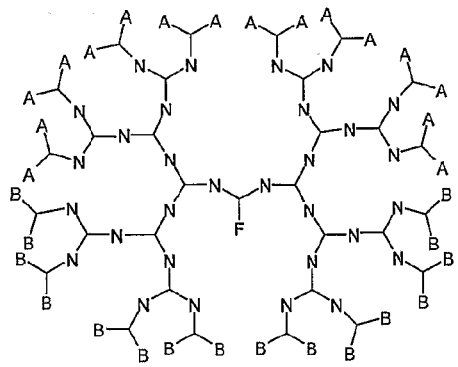
Figure 9:
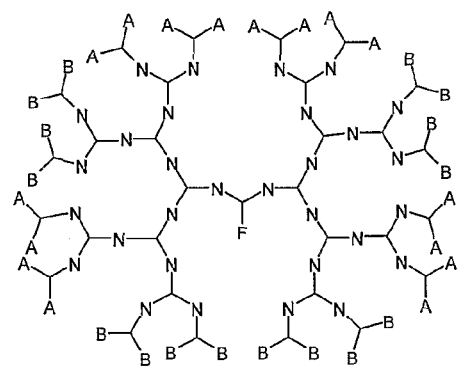
Figure 9:
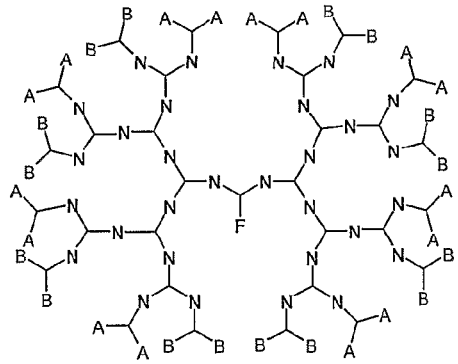
Figure 9:
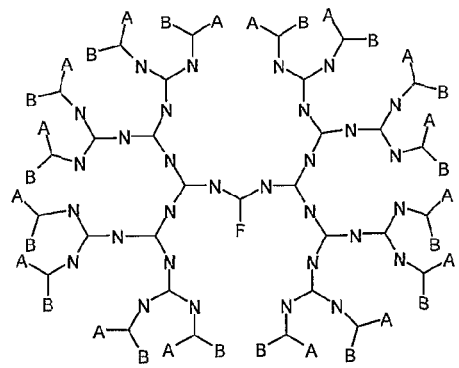

FIGS. 9.1 to 9.5—Schematic representations of selected topological isomers of lysine dendritic motifs according to a preferred embodiment of the invention having five layers of generation-building units from the apex F bearing termini groups A and B in a 1:1 surface ratio. A, B represent two different protecting groups or organic radicals and F represents the incomplete carboxylate at the apex.

Figure 10:
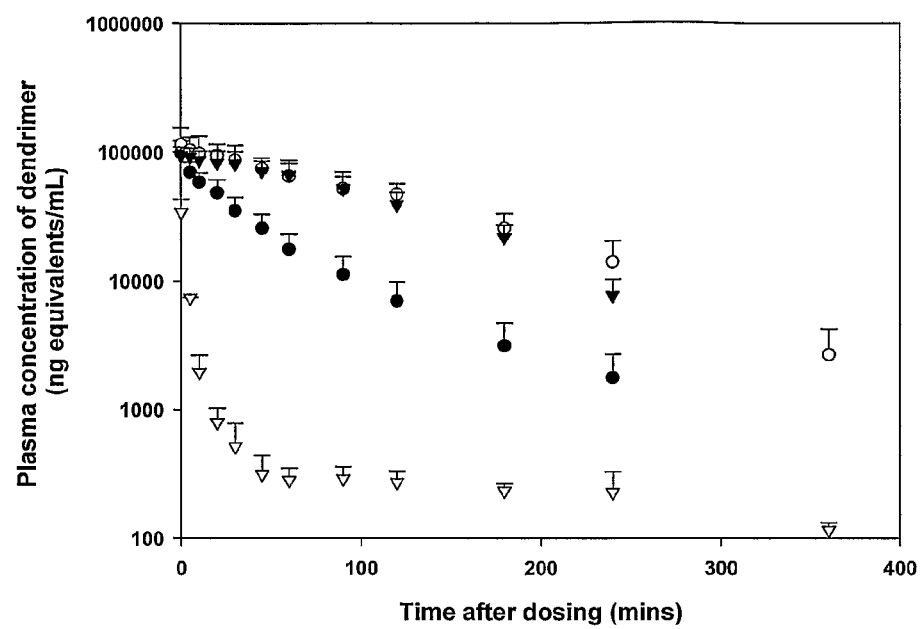

FIG. 10—Plasma concentration-time profile of BHALys[Lys]$_8$[CO-4-Ph(SO$_3$Na)]$_{16}$ (closed circle), BHALys[Lys]$_{16}$[CO-4-Ph(SO$_3$Na)]$_{32}$ (open circle) and BHALys[Lys]$_{16}$[CO-3,5-Ph(SO$_3$Na)$_2$]$_{32}$ (triangle) after 5 mg/kg IV dosing to rats.

Figure 11:
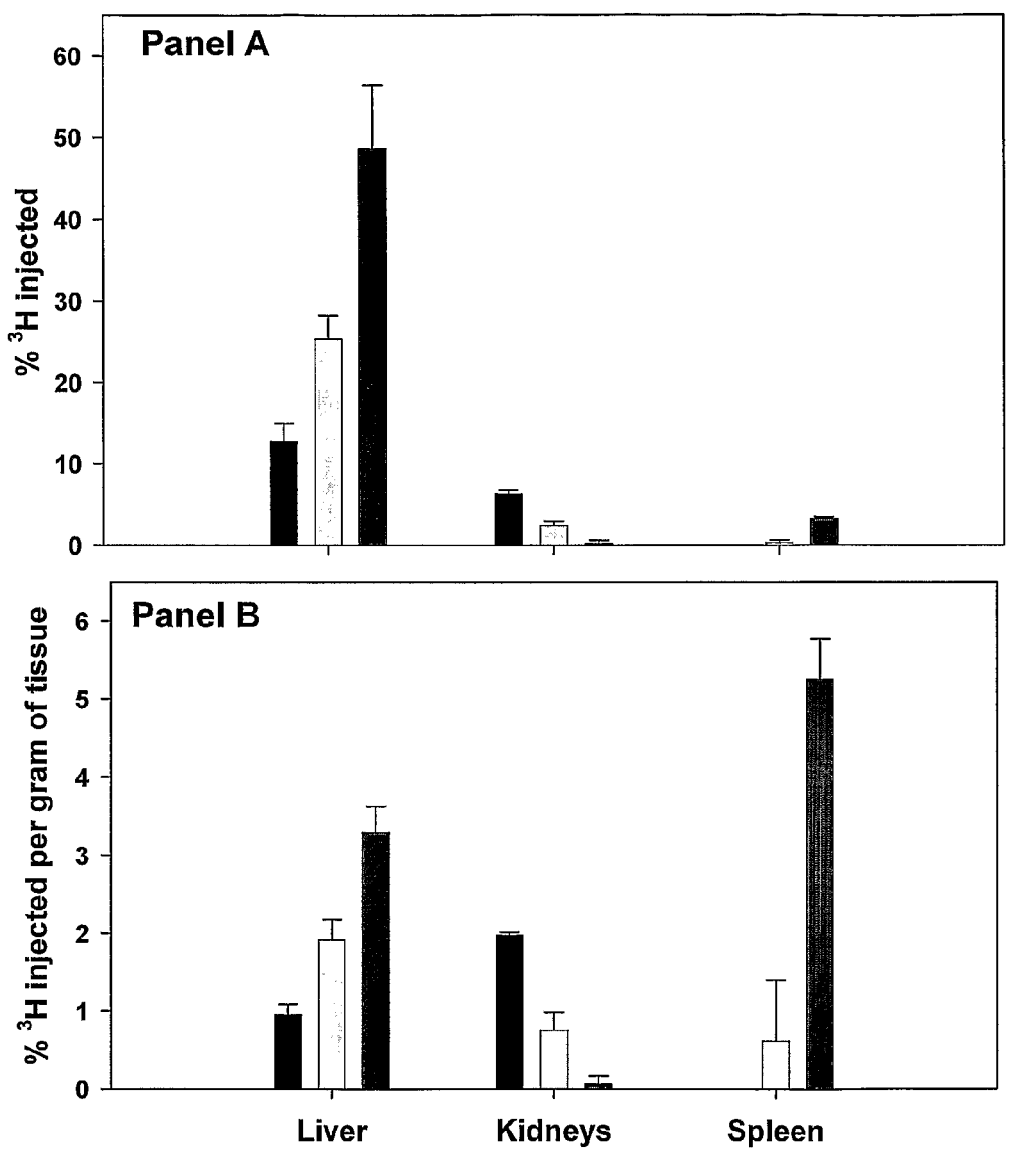

FIG. 11—Biodistribution of injected $^3$H 30 hours after IV dosing of BHALys[Lys]$_8$ [CO-4-Ph(SO$_3$Na)]$_{16}$ (black), BHALys[Lys]$_{16}$[CO-4-Ph(SO$_3$Na)]$_{32}$ (light grey), BHALys[Lys]$_{16}$[CO-3,5-Ph(SO$_3$Na)$_2$]$_{32}$ (dark grey) or BHALys[Lys]$_{16}$[CO—CH$_2$CH$_2$(CO$_2$Na)]$_{32}$ (white) to rats. Panel A —% of injected $^3$H present per organ. Panel B —% of injected $^3$H present per gram of tissue.

Figure 12:
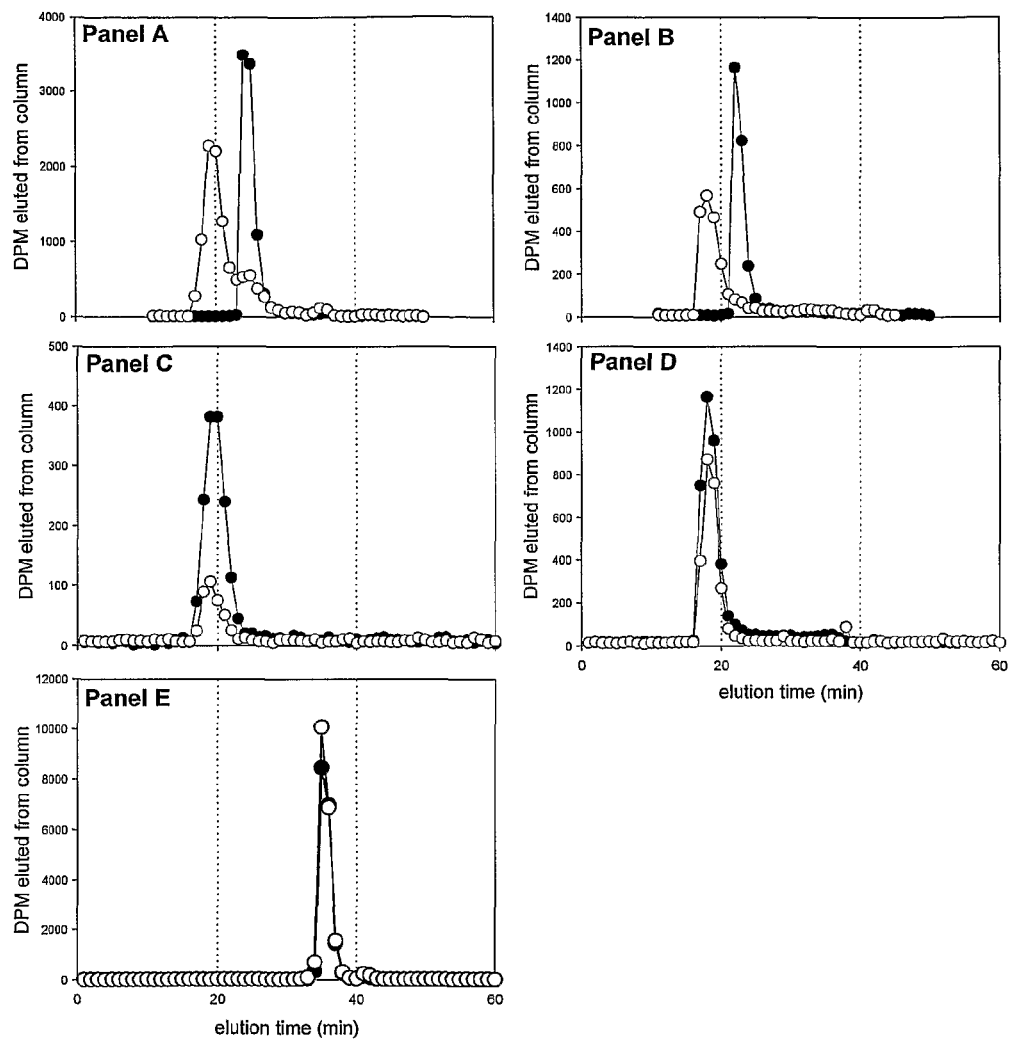

FIG. 12—Size exclusion profiles of BHALys[Lys]$_{16}$[CO-4-Ph(SO$_3$Na)]$_{32}$ and BHALys [Lys]$_{16}$[CO-3,5-Ph(SO$_3$Na)$_2$]$_{32}$ in plasma and urine on a superdex 75 column. Panel A—SEC profile of BHALys[Lys]$_{16}$[CO-4-Ph(SO$_3$Na)]$_{32}$ incubated for 1 hr in PBS (closed circles) or fresh plasma (open circles). Panel B—SEC profile of BHALys[Lys]$_{16}$[CO-3,5-Ph(SO$_3$Na)$_2$]$_{32}$ incubated for 1 hr in PBS (closed circles) or fresh plasma (open circles). Panel C—SEC profile of BHALys[Lys]$_{16}$[CO-4-Ph(SO$_3$Na)]$_{32}$ in plasma at t0 (closed circles) and 2 hr (open circles). Panel D—SEC profile of BHALys[Lys]$_{16}$[CO-3,5-Ph(SO$_3$Na)$_2$]$_{32}$ in plasma at t0 (closed circles) or 2 hr (open circles). Panel E—SEC profile of BHALys[Lys]$_{16}$[CO-4-Ph(SO$_3$Na)]$_{32}$ in 0-8 hr urine (closed circles) and 8-24 hr urine (open circles).

Figure 13:
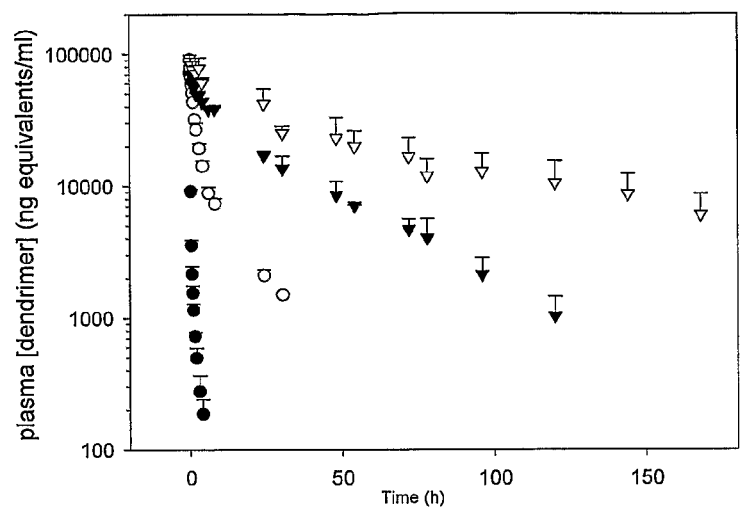

FIG. 13—Plasma concentration-time profiles for BHALys[Lys]$_{16}$[PEG$_{200}$]$_{32}$ (closed circles), BHALys[Lys]$_{16}$[PEG$_{570}$]$_{32}$ (open circles), BHALys[Lys]$_8$[PEG$_{2000}$]$_{16}$ (closed triangles) and BHALys[Lys]$_{16}$[PEG$_{2000}$]$_{32}$ (open triangles). Data for BHALys[Lys]$_8$ [PEG$_{200}$]$_{16}$ not shown as elimination is extremely rapid and obscured by the data for BHALys[Lys]$_{16}$[PEG$_{200}$]$_{32}$.

Figure 14:
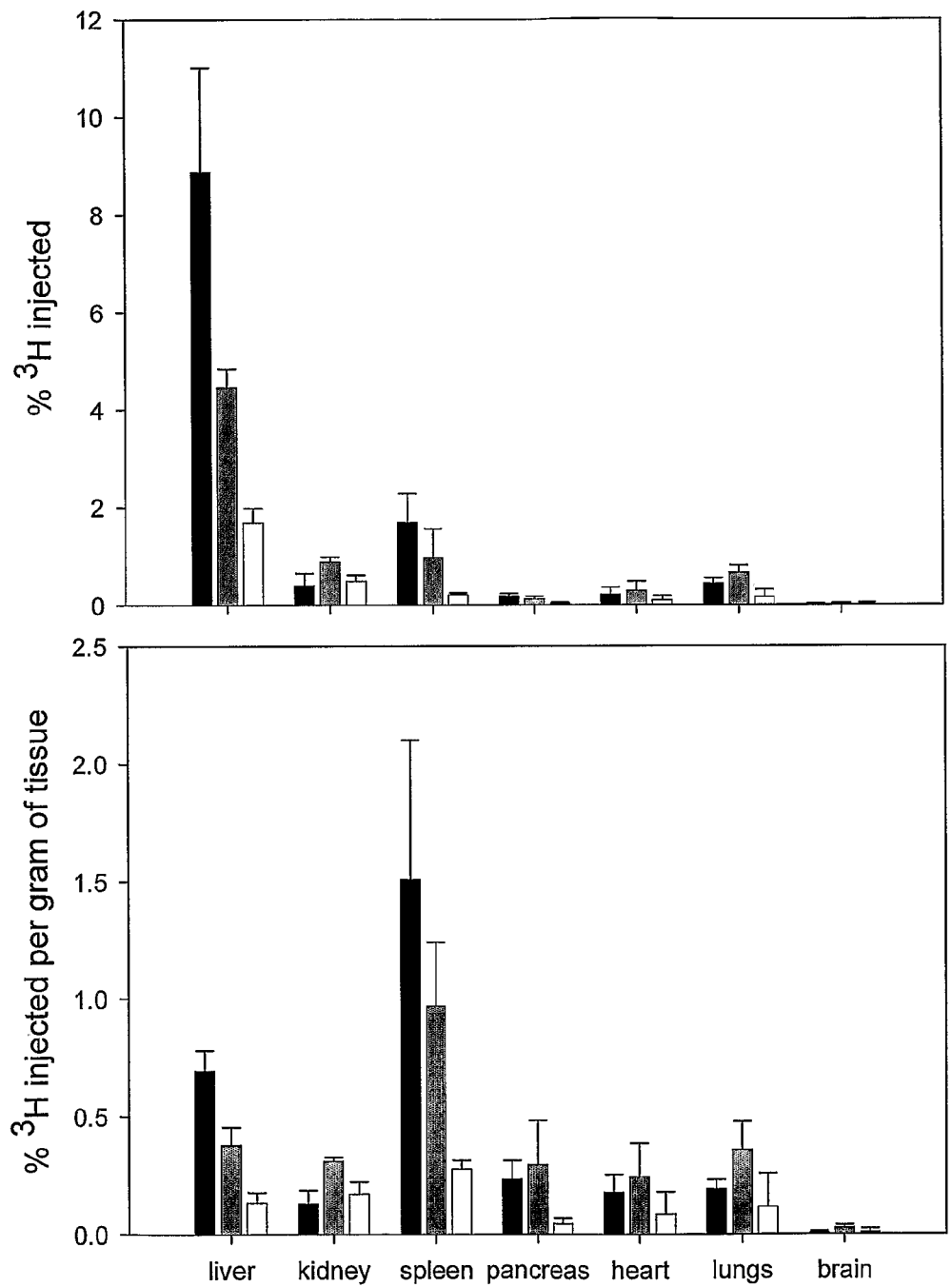
Figure 15:
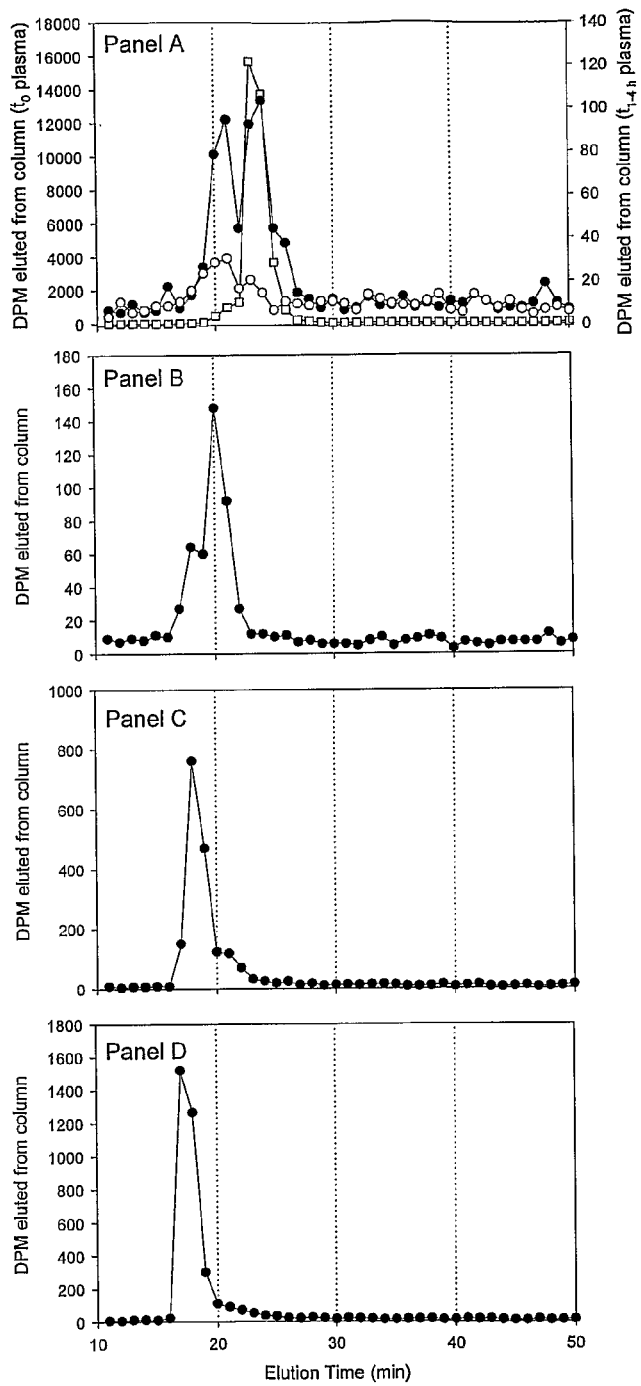

FIG. 14—Biodistribution of BHALys[Lys]$_{16}$[PEG$_{2000}$]$_{32}$ (black bars, 7 days), BHALys [Lys]$_8$[PEG$_{2000}$]$_{16}$ (grey bars, 5 days) and BHALys[Lys]$_{16}$[PEG$_{570}$]$_{32}$ (white bars, 30 hours) after IV dosing. The upper panel shows the % of injected $^3$H recovered in each organ while the lower panel shows the % of injected $^3$H recovered per gram of each tissue. Only 0.1% of the BHALys[Lys]$_{16}$[PEG$_{200}$]$_{32}$ dose was recovered in the kidneys 30 hours after IV dosing, whereas no $^3$H was detected in any organs in rats dosed with BHALys[Lys]$_8$[PEG$_{200}$]$_{16}$ (data not shown).

FIGS. 15A-D—Size exclusion profiles for $^3$H-labelled BHALys[Lys]$_{16}$[PEG$_{200}$]$_{32}$ (Panel A; t0, open square, t=1 h, closed circles, t=4 h, open circles), BHALys[Lys]$_{16}$[PEG$_{570}$]$_{32}$ (Panel B; 24 h), BHALys[Lys]$_8$[PEG$_{2000}$]$_{16}$ (Panel C; 48 h) and BHALys [Lys]$_{16}$[PEG$_{2000}$]$_{32}$ (Panel D; 48 h) in plasma after a 5 mg/kg IV dose on a Superdex 75 column. Arrows indicate the retention time of the intact dendrimer.

Figure 16:
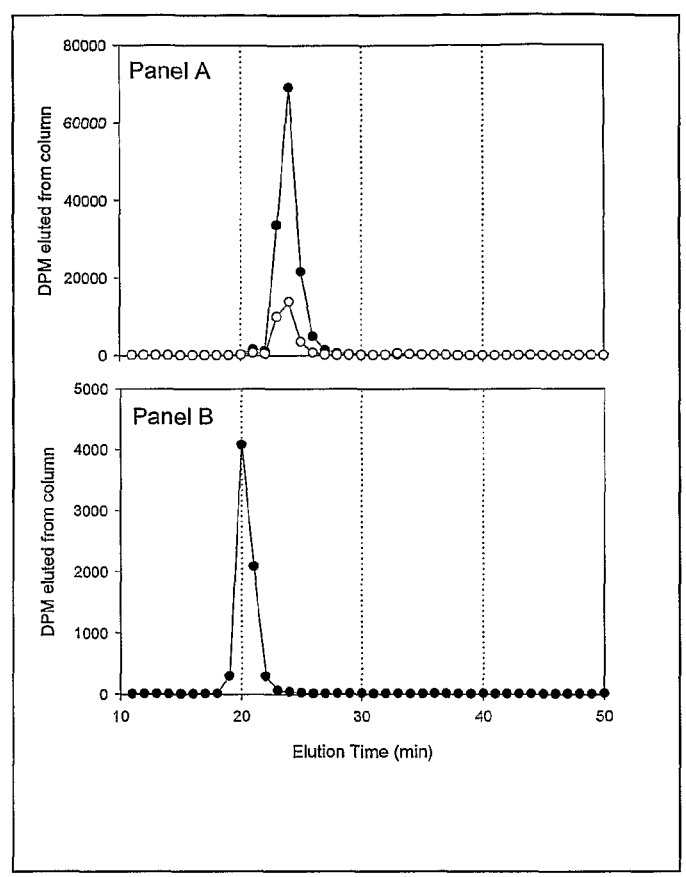

FIGS. 16A and B—Size exclusion profiles of $^3$H excreted in urine after IV dosing of BHALys[Lys]$_{16}$[PEG$_{200}$]$_{32}$ (Panel A; 0-4 h urine, closed circles, 8-24 h urine, open circles) and BHALys[Lys]$_{16}$[PEG$_{570}$]$_{32}$ (Panel B; 8-24 h urine). Arrows indicate the retention time of the intact dendrimer.

Figure 17:
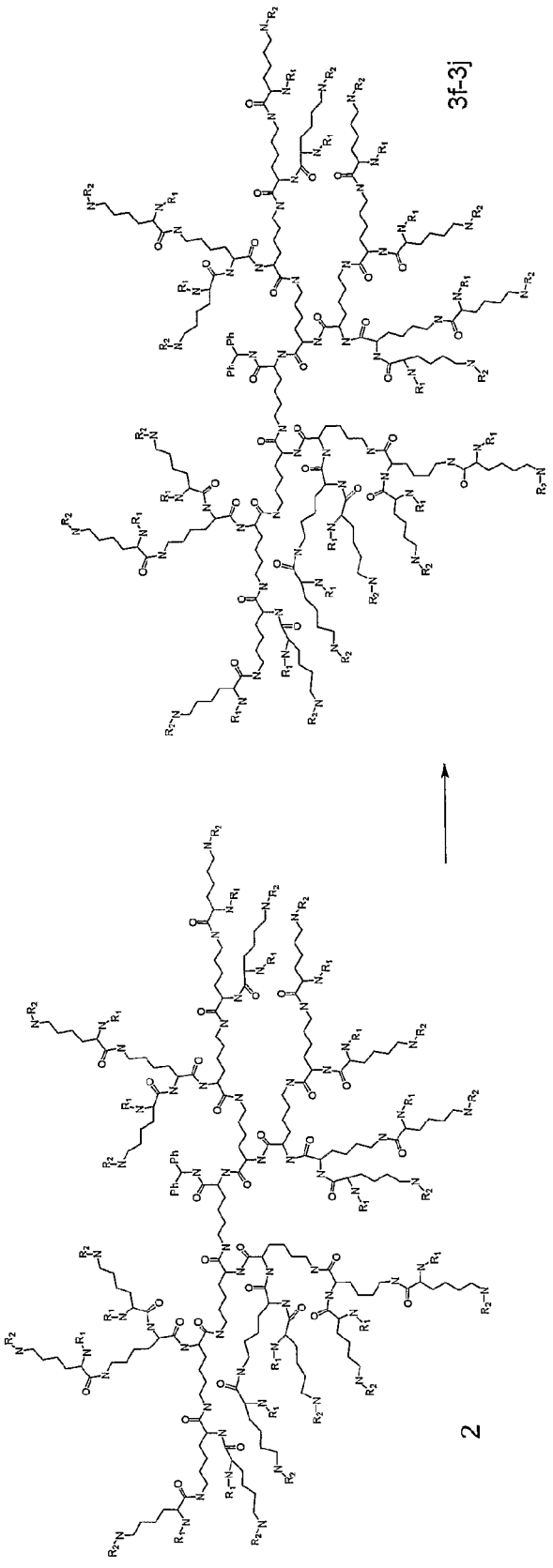

FIG. 17—Reaction Scheme 3 for preparation of BHALys [Lys]$_{16}$[α-PEG$_{570}$]$_{16}$[ε-MTX]$_{16}$.

Figure 18:
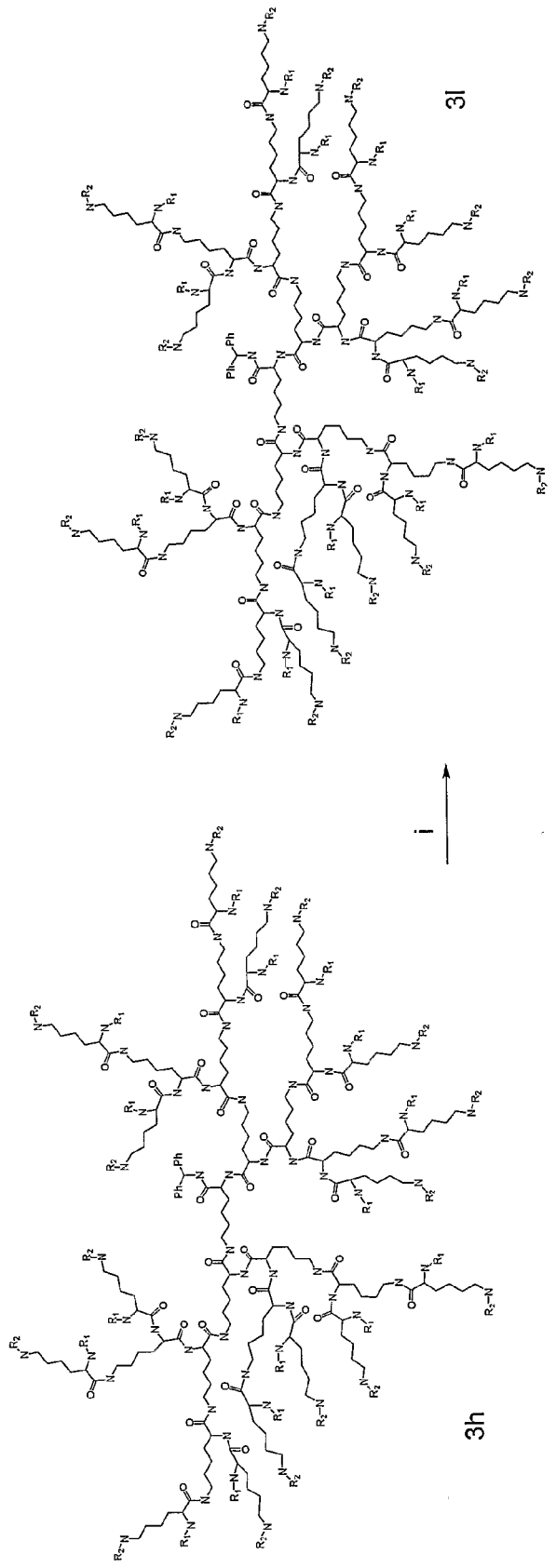

FIG. 18—Reaction Scheme 5 for preparation of BHALys [Lys]$_{16}$[α-PEG$_{570}$]$_{16}$-[ε-COCH$_2$CH$_2$CO-Taxol].

Figure 19A:
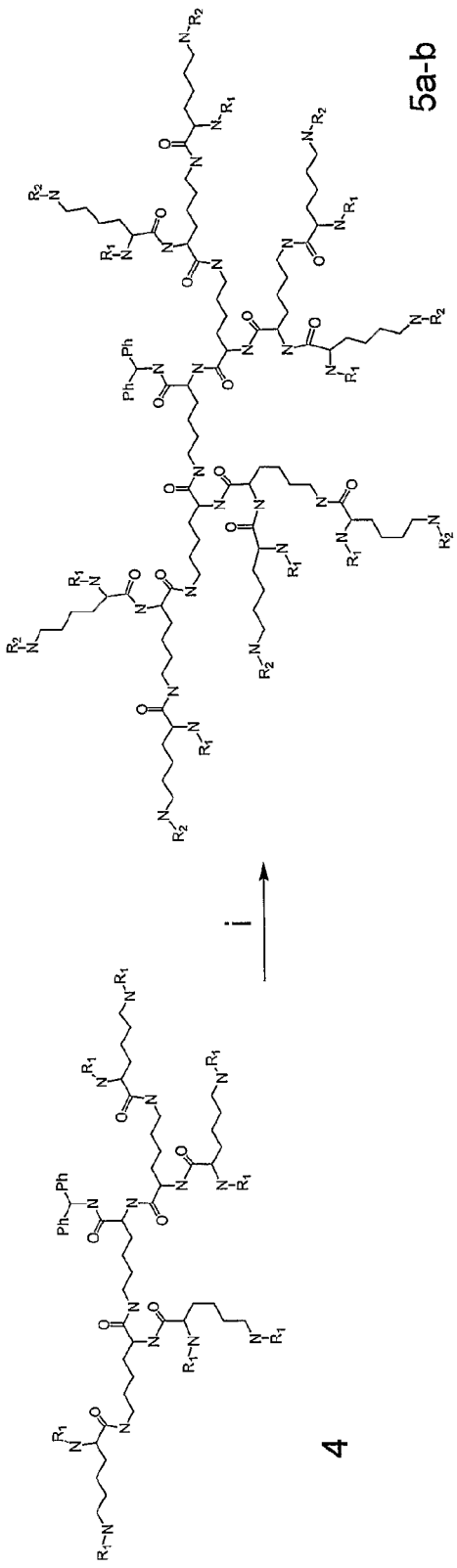

FIG. 19A—Reaction Scheme 6 (part 1) for preparation of BHALys[Lys]$_{16}$[ε,ε-PEG$_{570}$]$_8$[COCH$_2$CH$_2$CO-Taxol]$_{24}$.

Figure 19B:
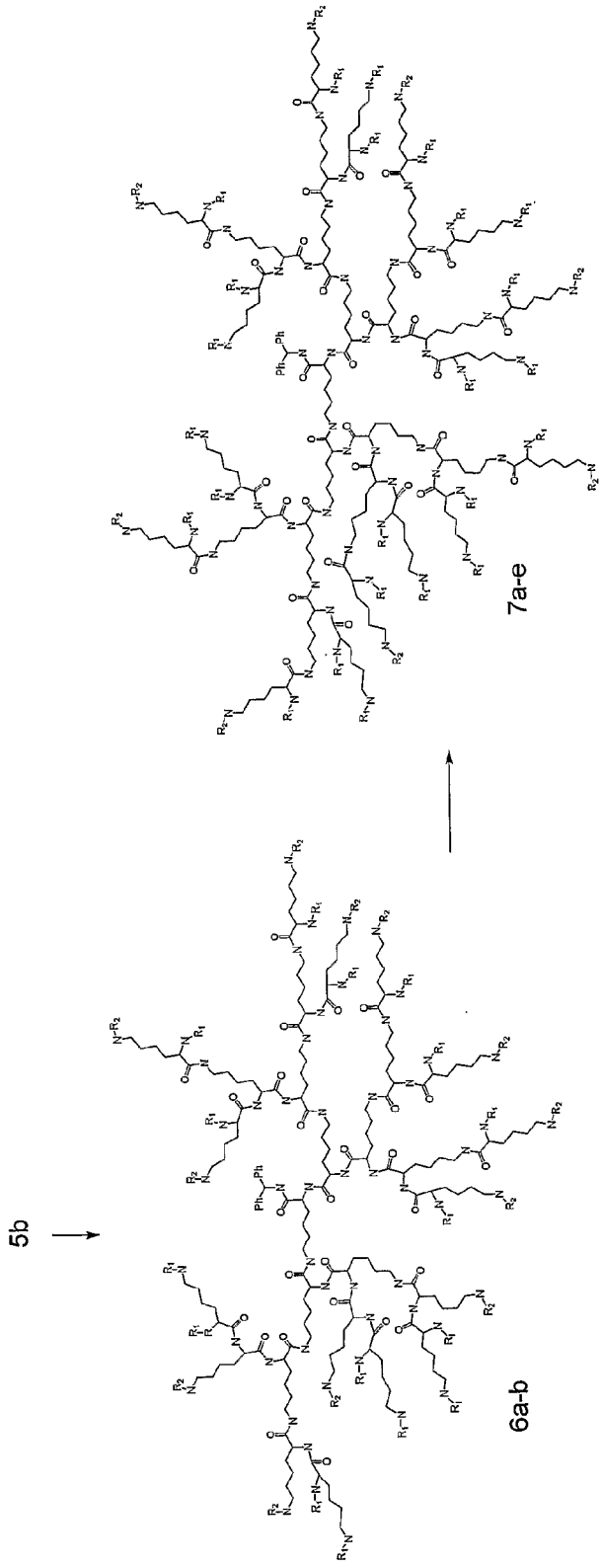

FIG. 19B—Reaction Scheme 6 (part 2) for preparation of BHALys[Lys]$_{16}$[ε,ε-PEG$_{570}$]$_8$[COCH$_2$CH$_2$CO-Taxol]$_{24}$.

Figure 20:
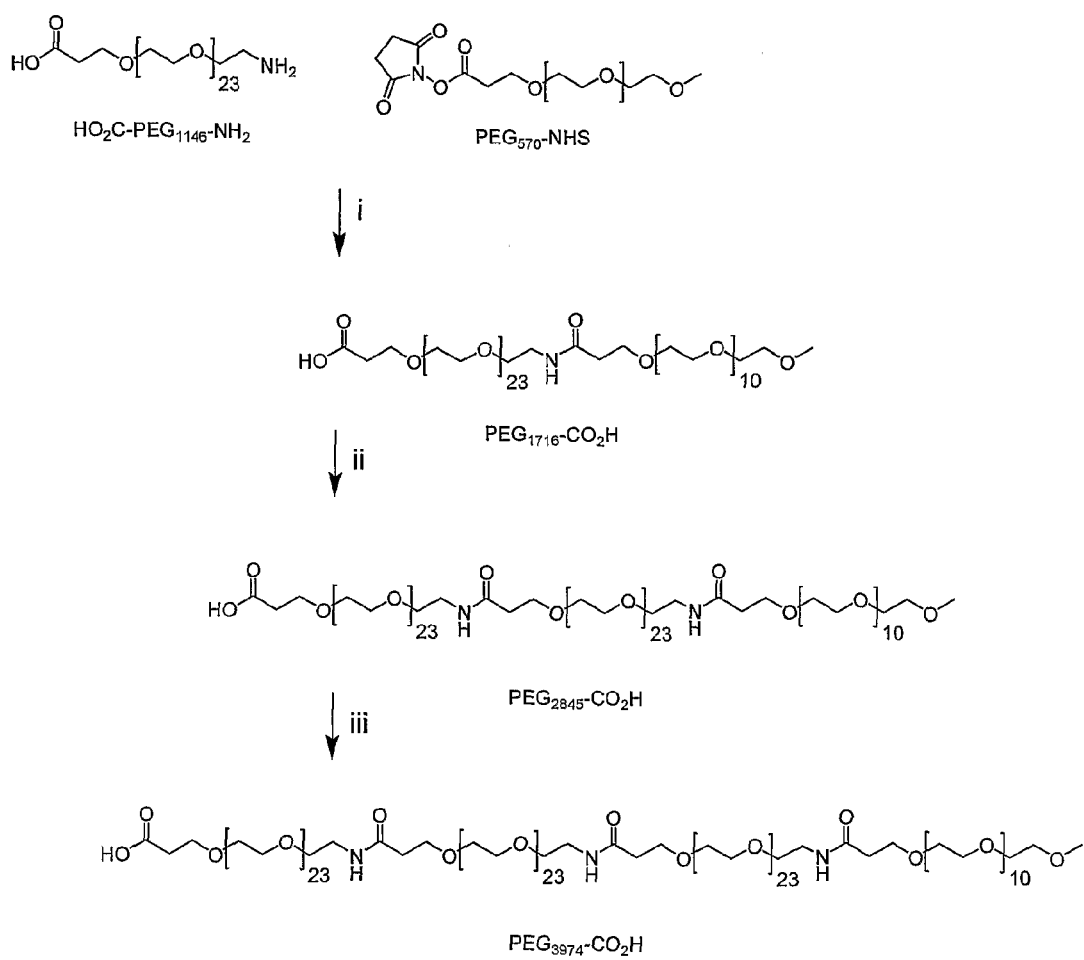

FIG. 20—Reaction Scheme 7 for preparation of PEG$_{1716}$-CO$_2$H, PEG$_{2645}$-CO$_2$H, PEG$_{3974}$-CO$_2$H.

Figure 21:
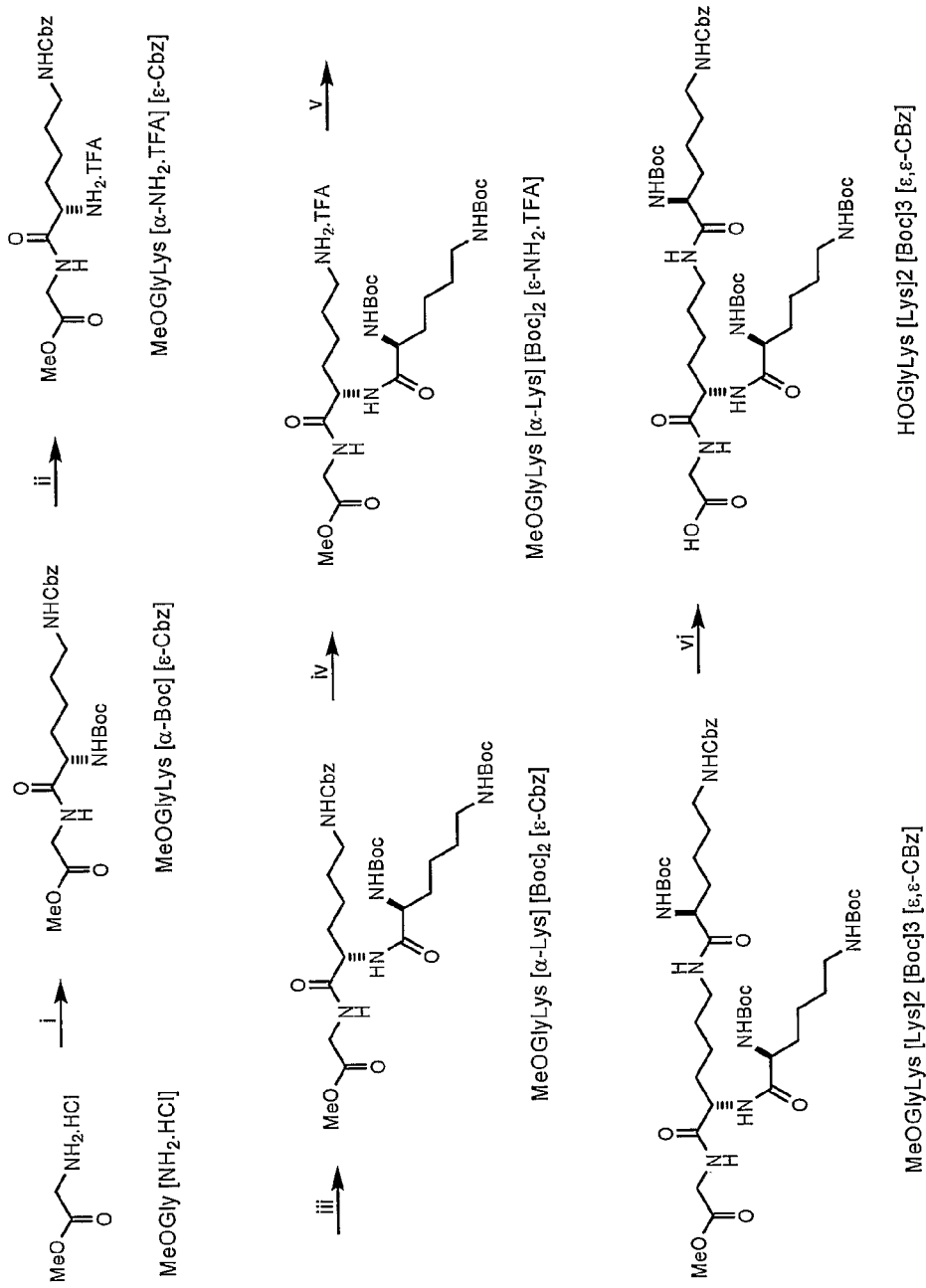

FIG. 21 illustrates the synthesis of Example 36 including the following steps:
i. Reaction of MeOGly[NH$_2$.HCl] with PNPO-Lys-α-Boc-ε-CBz and triethylamine in DMF; ii. Reaction of MeOGlyLys [α-Boc][ε-CBz] with 1:1 TFA/AcOH; iii. Reaction of MeOGlyLys[α-NH$_2$.TFA][ε-CBz] with DBL-OPNP and triethylamine in DMF; iv. Reaction of MeOGlyLys[α-Lys] [Boc]$_2$[ε-CBz] with catalytic palladium on carbon and one equivalent of TFA in methanol; v. Reaction of MeOGlyLys [α-Lys][Boc]$_2$[ε-NH$_2$.TFA] with PNPO-Lys-α-Boc-ε-CBz and triethylamine in DMF; vi. Reaction of MeOGlyLys [Lys]$_2$[Boc]$_3$[ε,ε-CBz] with sodium hydroxide in MeOH/H$_2$O followed by aqueous potassium hydrogen sulfate.

Figure 22:
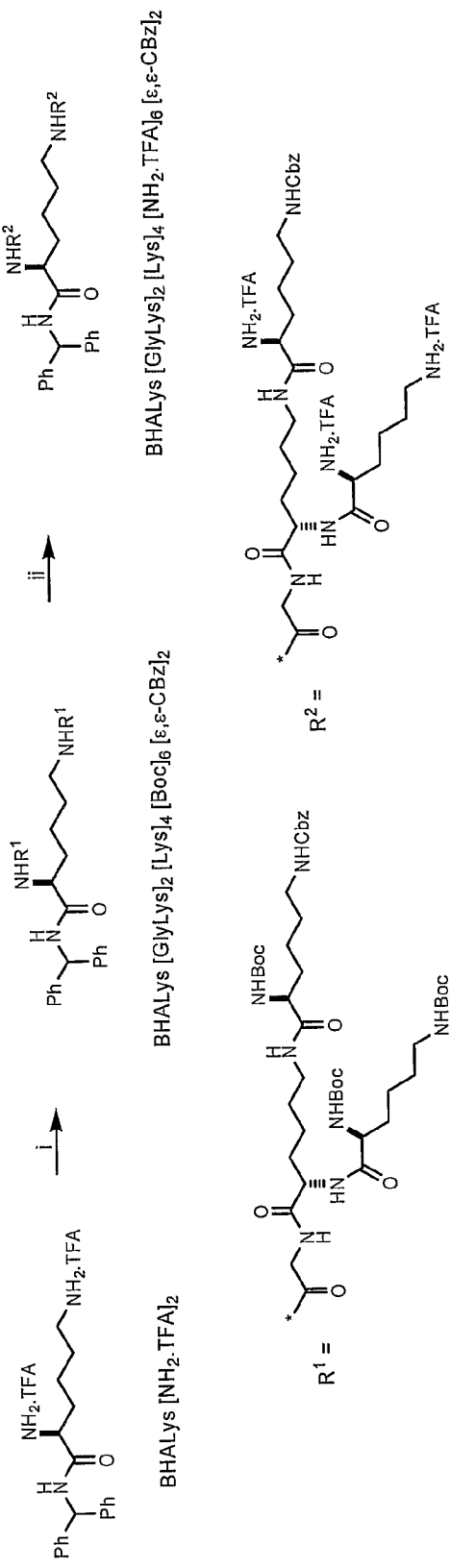

FIG. 22 illustrates the synthesis of Example 37, including the following steps:
i. Reaction of BHALys[NH$_2$.TFA]$_2$ with HOGlyLys [Lys]$_2$[Boc]$_3$[ε,ε-CBz], excess EDCI and HOBt in DMF; ii. Reaction of BHALys BHALys[GlyLys]$_2$[Lys]$_4$[Boc]$_6$[ε,ε-CBz]$_2$ with 1:1 TFA/AcOH.

Figure 23:
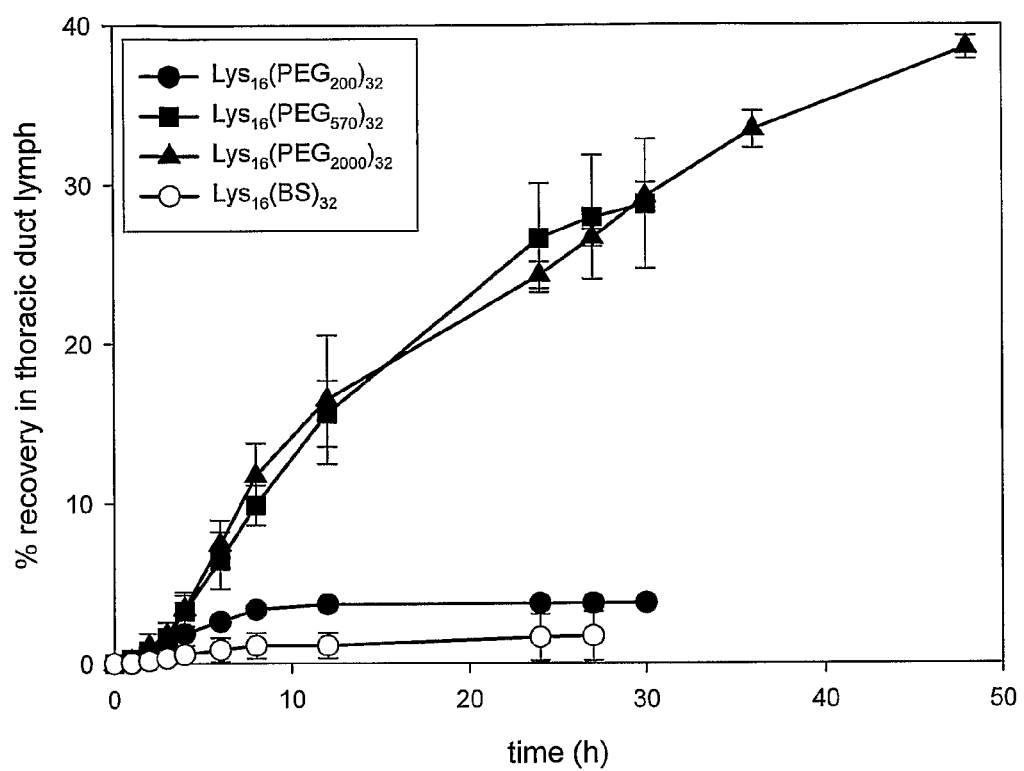

FIG. 23-Cumulative recovery of a subcutaneous dose of PEGylated dendrimer (black symbols) or non-PEGylated benzene sulphonate dendrimer (white symbols) in thoracic duct lymph over time. Results are mean±sd (n=1-3).

Figure 24:
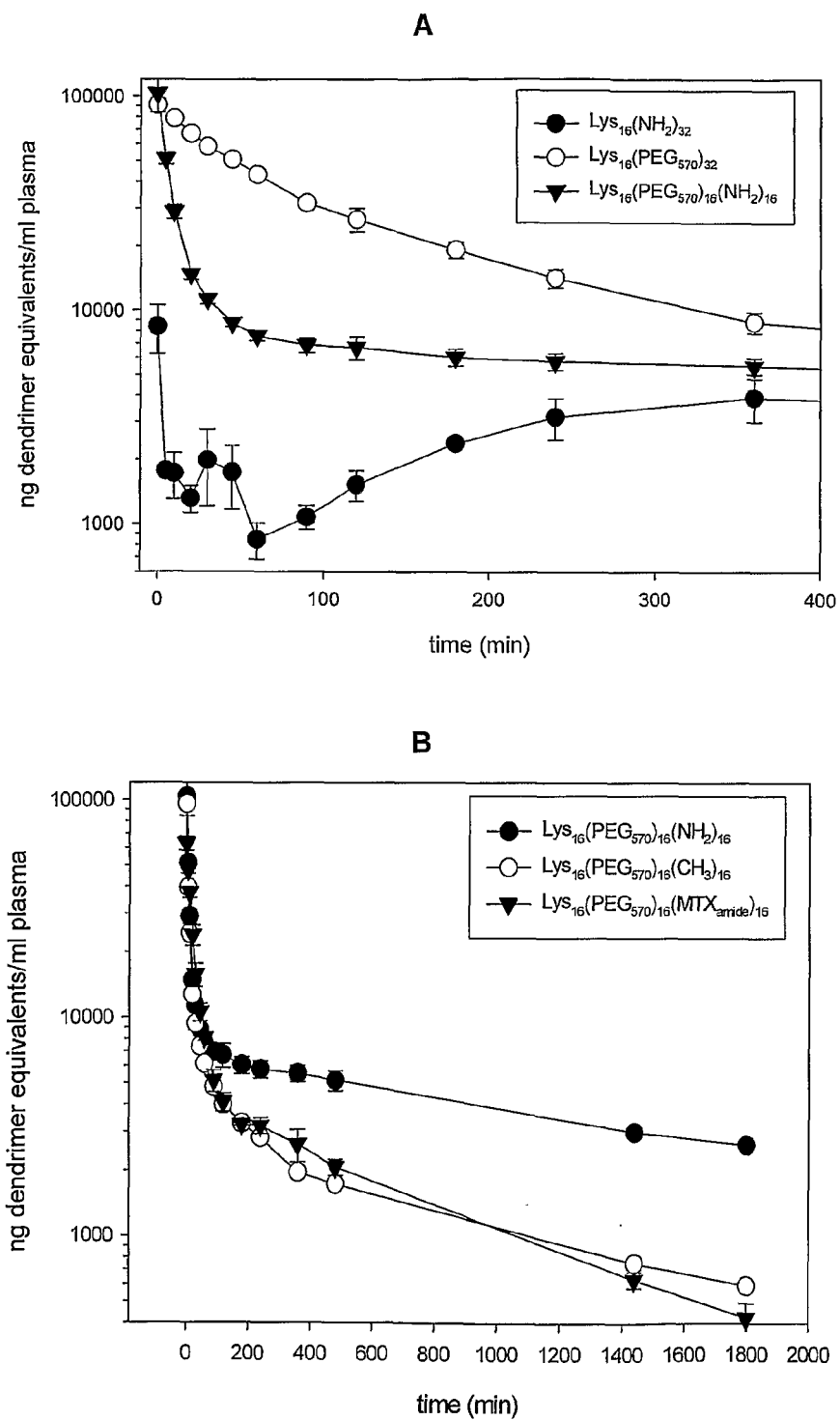

FIG. 24-Plasma concentration-time profiles of PEGylated and uncapped Lys$_{16}$ dendrimers. Panel A shows the initial decline in plasma concentrations of the fully-PEGylated, uncapped and half-PEGylated dendrimers. Data is represented as mean±sd (N=2-3).

Figure 25:
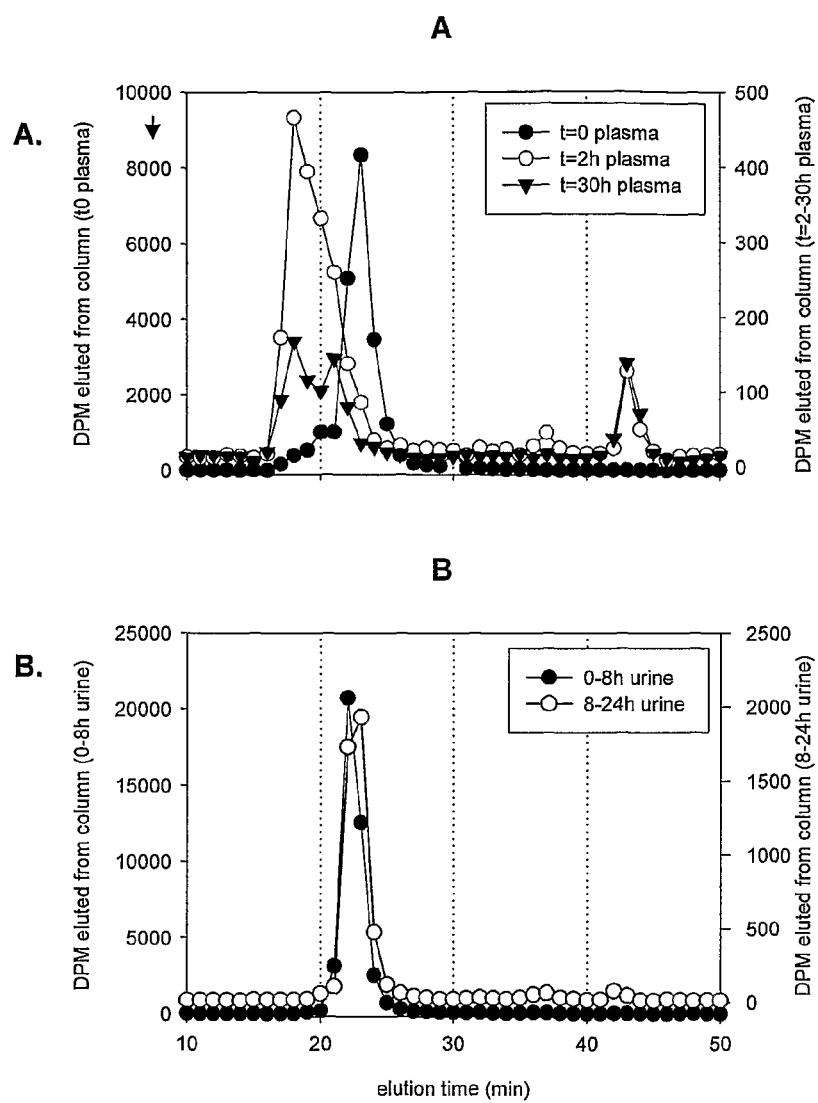

FIG. 25-SEC profiles of plasma (A) and urine (B) collected from a rat dosed with 5 mg/kg tritiated (G3 layer) Lys$_{16}$ (PEG$_{570}$)$_{16}$(NH$_2$)$_{16}$. The elution time of intact dendrimer is indicated by the arrow. Products eluting at 18 and 21 min are lysine reincorporation products. The peak eluting at 43 min is labelled lysine.

Figure 26:
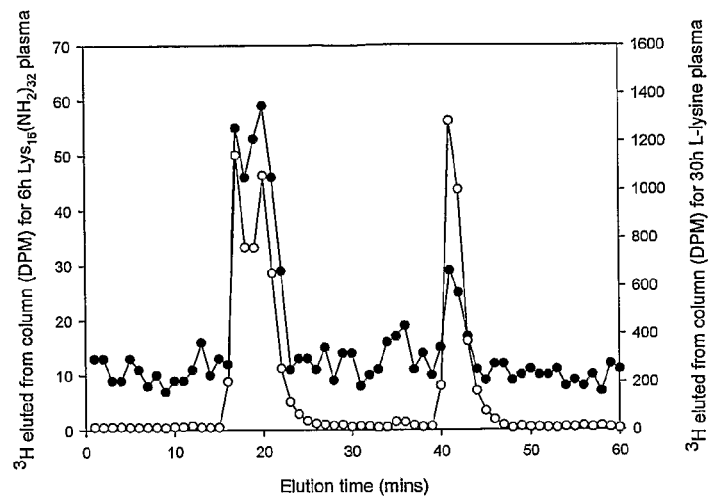

FIG. 26-SEC profiles of plasma collected from rats dosed with Lys$_{16}$(NH$_2$)$_{32}$ (6 h sample) and L-lysine (30 h sample). Peaks at 17 and 20 min are lysine reincorporation products. The peak at 41 min is tritiated lysine.

Figure 27:
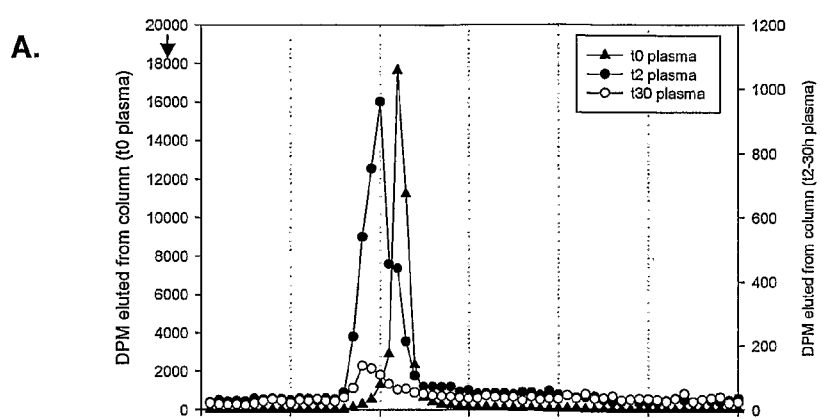
Figure 27:
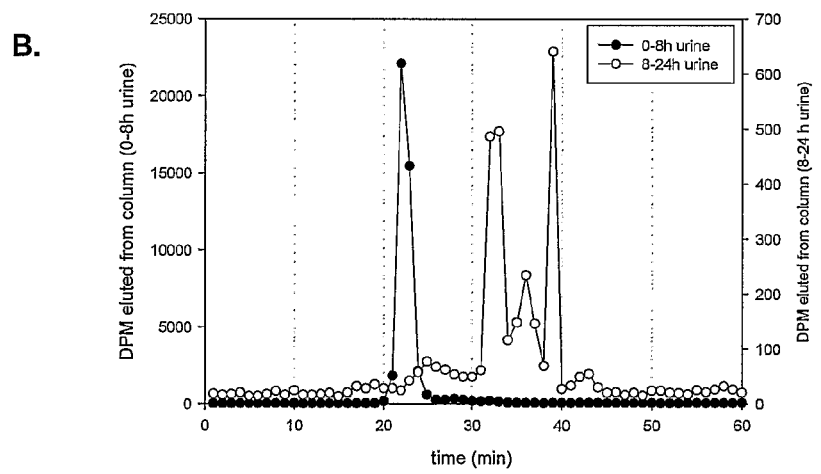

FIG. 27-SEC profiles of plasma and urine collected from a rat dosed with 5 mg/kg tritiated (G3 layer) Lys$_{16}$(PEG$_{570}$)$_{16}$(CH$_3$)$_{16}$. The elution time of intact dendrimer is indicated by the arrow. The products eluting at 18 min is a lysine reincorporation product. The peak eluting at 20 min is likely an anomalous peak associated with the intact dendrimer which is seen with the fully-capped species. The peak eluting at 43 min is labelled lysine. Peaks eluting between 30-40 min are likely core breakdown products.

EXAMPLES

The dendrimer nomenclature in the following examples makes use of the following formula:

Core[Last Complete Layer; Building Unit]$_n$–[Terminal group]$_m$[Incomplete Outer Layer; Building Unit]$_p$[Terminal group]$_q$ Where:
Core is the molecule to which the activated lysine generation building units are attached and will include at least one amine moiety to which the first layer of lysine building units is added, n is the number of lysine building units on the outermost complete layer of the macromolecule, p is the number of lysing building units on the incomplete outer layer of the macromolecule, m is the number of Terminal groups for example pharmaceutical active moieties or terminal amine protecting groups, on the outermost complete layer of building units; q is the number of Terminal groups on the incomplete outer layer of building units, Optionally, a Terminal group and/or building unit may be appended to the core; these are then denoted as [Terminal group]$_r$ [building unit]$_s$ following the same principle as above.

The nomenclature is able to completely describe the size of a macromolecule through provision of the core and the outer layer since only lysine building units are used in the construction of these macromolecule structures and the valency of the core is known, and further since all of the surface amine groups of each macromolecule layer are completely reacted with lysine during the addition of a new lysine layer.

TABLE 3

Macromolecule Nomenclature Abbreviations and Structures

| Abbreviation | Function | Name | Structure[1] |
| --- | --- | --- | --- |
| BHALys | Core | Benzhydrylamidolysine | |
| DAH | Core | Diaminohexane | |
| EDA | Core | Ethylenediamine | |
| TETA | Core | Triethyltetraamine | |
| NEOEOENLys | Core | | |

TABLE 3-continued

Macromolecule Nomenclature Abbreviations and Structures

| Abbreviation | Function | Name | Structure[1] |
|---|---|---|---|
| Su(NPN)$_2$ | Building unit | | |
| Lys | Building unit | Lysine | |
| NH$_2$•TFA | | Represents the terminal amine groups of the deprotected macromolecule, as the TFA salt, and is treated as a "terminal group" for the purposes of the nomenclature. | |
| Boc | Terminal Group | t-butyloxycarbonyl | |
| Fmoc | Terminal Group | Fluorenylmethoxy-carbonyl | |
| CBz | Terminal Group | Benzyloxycarbonyl | |
| COCH$_2$O-3,6-Naph(SO$_3$Na)$_2$ | Terminal Group | 1-carboxy-3,6-naphthyldisulfonic acid di-sodium salt | |

TABLE 3-continued

Macromolecule Nomenclature Abbreviations and Structures

| Abbreviation | Function | Name | Structure[1] |
|---|---|---|---|
| CO-3,5-Ph(SO$_3$Na)$_2$ | Terminal Group | 1-carboxy-3,5-phenyldisulfonic acid di-sodium salt | |
| CO-4-Ph(SO3Na) | Terminal Group | 1-carboxy-4-phenylsulfonic acid di-sodium salt | |
| CO$_2$(EtO)$_3$CH$_3$ | Terminal group | | |
| PEG$_{200}$ | Terminal Group | | |
| PEG$_{570}$ | Terminal Group | | |
| PEG$_{1100}$ | | | |
| PEG$_{2KD}$ | Terminal Group | | |
| PEG$_{1716}$ | Terminal Group | | |
| PEG$_{2845}$ | Terminal Group | | |
| PEG$_{3974}$ | Terminal Group | | |

TABLE 3-continued

Macromolecule Nomenclature Abbreviations and Structures

| Abbreviation | Function | Name | Structure[1] |
|---|---|---|---|
| | | | (structure: ethoxy-PEG$_{23}$-CH$_2$CH$_2$NH-C(O)-CH$_2$CH$_2$-O-PEG$_{10}$-OCH$_3$) |
| α-tBu-MTX | Terminal Group | α-t-Butyl-N-[4-[[2,4-diamino-6-pteridinyl)methyl]methyl-amino]benzoyl]-L-glutamate | (structure shown) |
| MTX | Terminal Group | N-[4-[[2,4-diamino-6-pteridinyl)methyl]methyl-amino]benzoyl]-L-glutamate | (structure shown) |
| COCH$_2$CH$_2$CO-Taxol | Terminal Group | | (structure shown) |
| COCH$_3$ | Terminal Group | Acetamide | (structure shown) |
| [BOC][Cbz][NPN]$_2$ | Reagent | | (structure shown) |
| [BOC][Cbz][NPN]$_2$SuOH | Reagent | | (structure shown) |

TABLE 3-continued
Macromolecule Nomenclature Abbreviations and Structures
| Abbreviation | Function | Name | Structure[1] |
|---|---|---|---|
| [BOC][Cbz][NPN]$_2$SuOPNP | Reagent | | 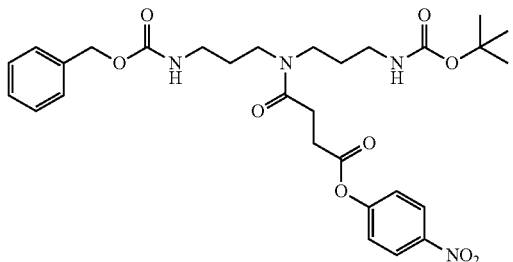 |
| [BOC][Cbz][NPN]$_2$SuOEt | Reagent | | 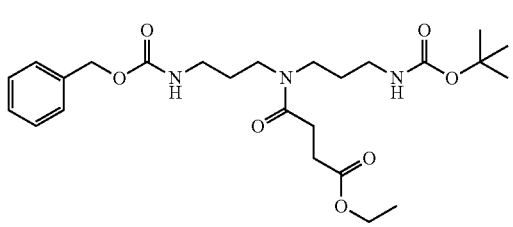 [SMILES: CCOC(=O)CCC(=O)N(CCCNC(=O)OCc1ccccc1)CCCNC(=O)OC(C)(C)C] |
| [BOC][NH$_2$][NPN]$_2$SuOEt | Reagent | | 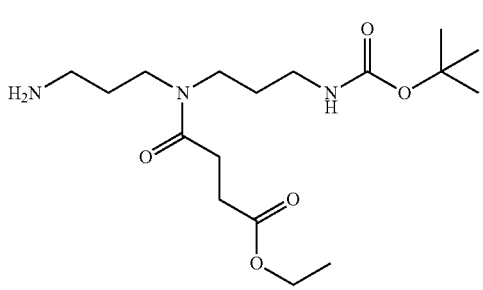 [SMILES: CCOC(=O)CCC(=O)N(CCCN)CCCNC(=O)OC(C)(C)C] |
| [BOC][PEG][NPN]$_2$SuOEt<br>PEG$_{570}$ n = 10<br>PEG$_{1100}$ n = 22 | Reagent | | 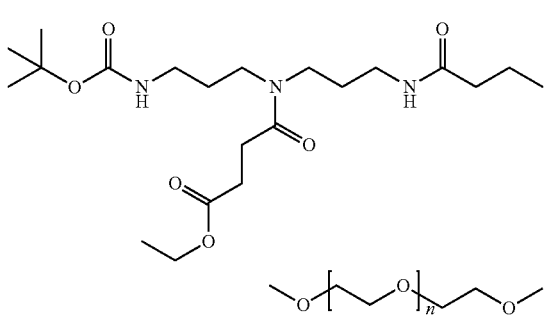 |
| [α-tBu-MTX][PEG][NPN]$_2$SuOEt<br>PEG$_{570}$ n = 10<br>PEG$_{1100}$ n = 22 | Reagent | | 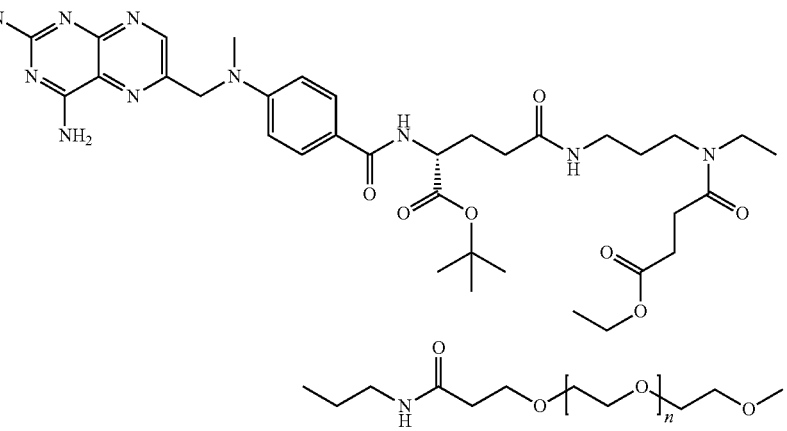 |

TABLE 3-continued

Macromolecule Nomenclature Abbreviations and Structures

| Abbreviation | Function | Name | Structure[1] |
|---|---|---|---|
| [α-tBu-MTX][PEG][NPN]$_2$SuOEt PEG$_{570}$ n = 10 PEG$_{1100}$ n = 22 | Reagent | | |
| PFP-Lys-α-Fmoc-ε-Boc | Reagent | Pentafluorophenol active ester of α-Fmoc ε-Boc-Lysine | |
| PFP-Lys-α-Boc-ε-Fmoc | Reagent | Pentafluorophenol active ester of α-Boc-ε-Fmoc-Lysine | |
| HO-Lys-α-Fmoc-ε-Boc | Reagent | α-Fmoc-ε-Boc-Lysine | |
| DBL-OPNP | Reagent | p-Nitrophenol active ester of α,ε-(Boc)$_2$-Lysine | |
| PNPO-α-Boc-ε-CBz-Lys | Reagent | p-Nitrophenol active ester of α-Boc-ε-CBz-Lysine | |
| PNPO-α-CBz-ε-Boc-Lys | Reagent | p-Nitrophenol active ester of α-CBz-ε-Boc-Lysine | |
| PEG$_{570}$-NHS | Reagent | N-hydroxysuccinimide ester of MeO—(CH$_2$CH$_2$O)$_{11}$CH$_2$CH$_2$CO$_2$H | |
| PEG$_{1100}$-OH | Reagent | | |
| PEG$_{1100}$-NHS | Reagent | | |
| HO$_2$C-PEG$_{1146}$-NH$_2$ | Reagent | | |
| α-tBu-γ-MTX-OH | Reagent | α-t-Butyl-N-[4-[[2,4-diamino-6-pteridinyl)methyl]methyl-amino]benzoyl]-L-glutamate | |

TABLE 3-continued

Macromolecule Nomenclature Abbreviations and Structures

| Abbreviation | Function | Name | Structure[1] |
|---|---|---|---|
| HO$_2$CCH$_2$CH$_2$CO-Taxol | Reagent | | |

[1]Asterisk indicates amine group bonded as amide to carboxyl group of lysine branching unit. Hash indicates carboxyl group bonded as amide to amine of core or lysine branching unit Further chemical abbreviations are listed in Table 4.

TABLE 4

Chemical Names and Abbreviations.

| Abbreviation | Full Name |
|---|---|
| PyBop | Benzotriazole-1-yl-oxy-tris-pyrrolidino-phosphonium hexafluorophosphate |
| DMF | Dimethylformamide |
| TFA | Trifluoroacetic acid |
| DMSO | Dimethylsulfoxide |
| DCM | Dichloromethane |
| EDCI | N-(3-Dimethylaminopropyl)-N'-ethylcarbodiimide |
| DIPEA | Diisopropylethylamine |
| TEA | Triethylamine |
| HOBt | Hydroxybenzotriazole |
| Rt | Room temperature |
| Ca | Circa |
| Ppt | Precipitate |
| Fcc | Flash Column Chromatography |
| PTLC | Preparative Thin Layer Chromatography |
| HPLC | High Performance Liquid Chromatography |
| MS | Mass Spectrometry |
| CE | Capillary Electrophoresis |
| PFP-Lys-α-Fmoc-ε-Boc | Pentafluorophenol active ester of α-Fmoc-ε-Boc-Lysine |
| HO-Lys-α-Fmoc-ε-Boc | α-Fmoc-ε-Boc-Lysine |
| HO-Lys-α-Boc-ε-Fmoc | α-Boc-ε-Fmoc-Lysine |
| PFP-Lys-α-Boc-ε-Fmoc | Pentafluorophenol active ester of α-Boc-ε-Fmoc-Lysine |
| DBL-OPNP | p-Nitrophenol active ester of α,ε-(Boc)$_2$-Lysine |
| PFP-Lys-(Fmoc)$_2$ | Pentafluorophenol active ester of α,ε-(Fmoc)$_2$-Lysine |
| PNPO-α-Boc-ε-CBz-Lys | p-Nitrophenol active ester of α-Boc-ε-CBz-Lysine |
| PNPO-α-CBz-ε-Boc-Lys | p-Nitrophenol active ester of α-CBz-ε-Boc-Lysine |

Example 1

Examples of pharmaceutically active agents that may be used in the present invention include the following:

Methotrexate

Methotrexate is an antimetabolite drug used in the treatment of cancer and autoimmune disease. It acts by inhibiting the metabolism of folic acid by competitively and reversibly inhibiting dihydrofolate reductase.

Chemically methotrexate is N-[4-[[(2,4-diamino-6-pteridinyl)methyl]methylamino]-benzoyl]-L-glutamic acid.

Molecular weight: 454.45 C$_{20}$H$_{22}$N$_8$O$_5$ and the structural formula is:

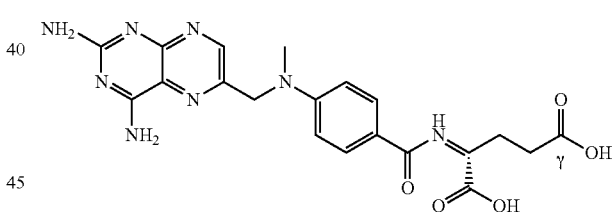

The higher doses of methotrexate used in cancer chemotherapy can cause toxic side effects to rapidly dividing cells of bone and gastrointestinal mucosa.

Taxol

Taxol (paclitaxel) is an antimitotic agent used as a treatment particularly in women with breast and ovarian cancer that has not responded to prior therapy. It acts by stabilising microtubules and promoting microtubule assembly, thereby destroying the cell's ability to use its cytoskeleton in a flexible manner. Taxol is a tricyclic diterpene and the structural formula is

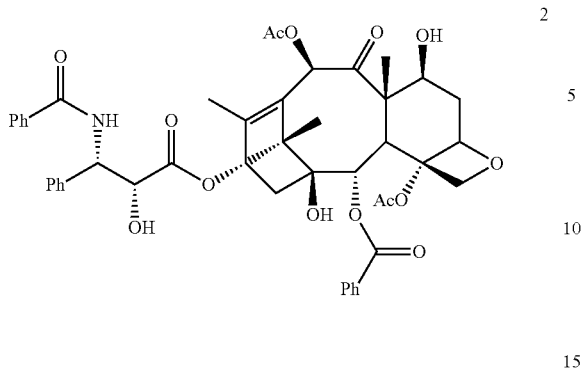

Zenical

Zenical (also referred to as Xenical, Xenecal and Zencal) is a weight control medication for the management of obesity. It exerts its therapeutic activity in the lumen of the stomach and small intestine by forming a covalent bond with the active serine residue site of gastric and pancreatic lipases. The inactivated enzymes are thus unavailable to hydrolyse dietary fat in the form to triglycerides into absorbable free fatty acids and monoglycerides.

Chemically Zenical has the structural formula

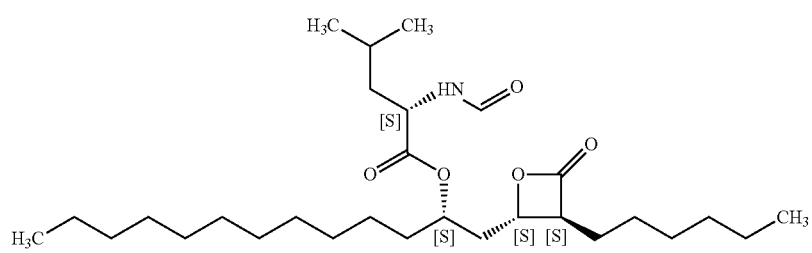

The chemical name for Zenical is (S)-2-formylamino-4-methyl-pentanoic acid (S)-1 [[(2S, 3S)-3-hexyl-4-oxo-2-oxetanyl]methyl]-dodecyl ester. The molecular formula is $C_{29}H_{53}NO_5$. Zenical has a molecular weight of 495.7.

There are a number of undesirable gastrointestinal side effects including flatulence, faecal urgency, fatty/oily stools and loose stools.

Indomethacin

Indomethacin (also indometacin) is a non-steroidal anti-inflammatory drug commonly used to reduce fever, pain, stiffness, and swelling. It works by inhibiting the production of prostaglandins, molecules known to cause these symptoms.

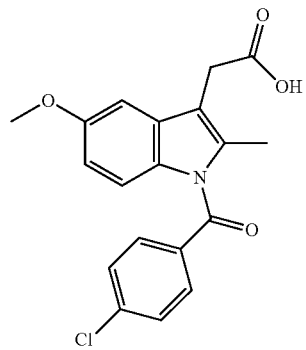 [SMILES: COc1ccc2c(c1)c(CC(=O)O)c(C)n2C(=O)c1ccc(Cl)cc1]

Cyclosporin

Cyclosporin is an immunosuppressive used extensively in the prevention and treatment of graft-versus-host reactions in transplantations. It has also been tested for the therapy of a large variety of other diseases in which immunological factors may have a pathogenic role.

Example 2

Methotrexate-Bearing Dendrimers

Lysine dendrimers were prepared wherein approximately 50% and approximately 75% of the terminal groups are a drug (specifically Methotrexate). The Methotrexate may be conjugated to the dendrimer through a stable bond, and the clearance and biodistribution of this construct are determined.

It may be desirable to increase the size of the individual PEG groups as their relative abundance is decreased, in order to maintain the required plasma lifetime and avoid liver uptake. The "non-cleavable" nature of the Methotrexate maintains the integrity of the construct during plasma exposure.

Detailed description of compounds:
BHALys[Lys]$_{16}$[α-PEG$_{570}$]$_{16}$[ε-MTX]$_{16}$
BHALys[Lys]$_{16}$[α-PEG$_{1100}$]$_{16}$[ε-MTX]$_{16}$
BHALys[Lys]$_{16}$[α-PEG$_{1716}$]$_{16}$[ε-MTX]$_{16}$ BHALys[Lys]$_{16}$[α-PEG$_{2845}$]$_{16}$[ε-MTX]$_{16}$
BHALys[Lys]$_{16}$[α-PEG$_{3974}$]$_{16}$[ε-MTX]$_{16}$
BHALys[Lys]$_8$[Su(NPN)$_2$]$_{16}$[MTX]$_{16}$[PEG$_{570}$]$_{16}$
BHALys[Lys]$_8$[Su(NPN)$_2$]$_{16}$[MTX]$_{16}$[PEG$_{1100}$]$_{16}$
BHALys[Lys]$_8$[Su(NPN)$_2$]$_{16}$[MTX]$_{16}$[PEG$_{1716}$]$_{16}$
BHALys[Lys]$_8$[Su(NPN)$_2$]$_{16}$[MTX]$_{16}$[PEG$_{2845}$]$_{16}$
BHALys[Lys]$_8$[Su(NPN)$_2$]$_{16}$[MTX]$_{16}$[PEG$_{3974}$]$_{16}$ Where MTX represents methotrexate 1, conjugated through the γ-carboxylate group. The key intermediate for this approach is 3, prepared according to the methods described in Aust. J. Chem. 2002 55 635-645.

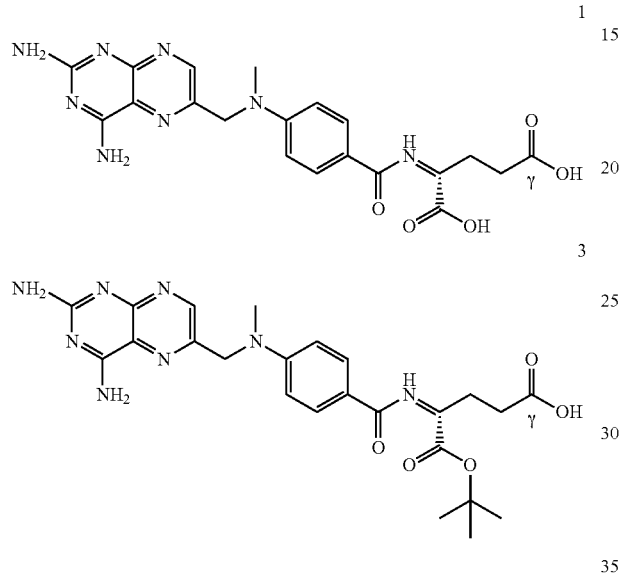

Example 3

Taxol-Bearing Dendrimers

Examples of Taxol-bearing dendrimers include the following:

BHALys[Lys]$_{16}$[α-PEG$_{570}$]$_{16}$[ε-COCH$_2$CH$_2$CO-Taxol]$_{16}$
BHALys[Lys]$_{16}$[α-PEG$_{1100}$]$_{16}$[ε-COCH$_2$CH$_2$CO-Taxol]$_{16}$
BHALys[Lys]$_{16}$[α-PEG$_{1716}$]$_{16}$[ε-COCH$_2$CH$_2$CO-Taxol]$_{16}$
BHALys[Lys]$_{16}$[α-PEG$_{2845}$]$_{16}$[ε-COCH$_2$CH$_2$CO-Taxol]$_{16}$
BHALys[Lys]$_{16}$[α-PEG$_{3974}$]$_{16}$[ε-COCH$_2$CH$_2$CO-Taxol]$_{16}$
BHALys[Lys]$_8$[Su(NPN)$_2$]$_{16}$[PEG$_{570}$]$_{16}$[COCH$_2$CH$_2$CO-Taxol]$_{16}$
BHALys[Lys]$_8$[Su(NPN)$_2$]$_{16}$[PEG$_{1100}$]$_{16}$[COCH$_2$CH$_2$CO-Taxol]$_{16}$
BHALys[Lys]$_8$[Su(NPN)$_2$]$_{16}$[PEG$_{1716}$]$_{16}$[COCH$_2$CH$_2$CO-Taxol]$_{16}$
BHALys[Lys]$_8$[Su(NPN)$_2$]$_{16}$[PEG$_{2845}$]$_{16}$[COCH$_2$CH$_2$CO-Taxol]$_{16}$
BHALys[Lys]$_8$[Su(NPN)$_2$]$_{16}$[PEG$_{3974}$ [COCH$_2$CH$_2$CO-Taxol]$_{16}$
BHALys[Lys]$_{16}$[ε,ε-PEG$_{570}$]$_8$[COCH$_2$CH$_2$CO-Taxol]$_{24}$
BHALys[Lys]$_{16}$[ε,ε-PEG$_{1100}$]$_8$[COCH$_2$CH$_2$CO-Taxol]$_{24}$
BHALys[Lys]$_{16}$[ε,ε-PEG$_{1716}$]$_8$[COCH$_2$CH$_2$CO-Taxol]$_{24}$
BHALys[Lys]$_{16}$[ε,ε-PEG$_{2845}$]$_8$[COCH$_2$CH$_2$CO-Taxol]$_{24}$
BHALys[Lys]$_{16}$[ε,ε-PEG$_{3974}$]$_8$[COCH$_2$CH$_2$CO-Taxol]$_{24}$ The conjugation of Taxol may be conducted using two different derivatives; 2 and 4 see below). The preparation of 2 is described in J. Med. Chem. 1989 32 788-792.

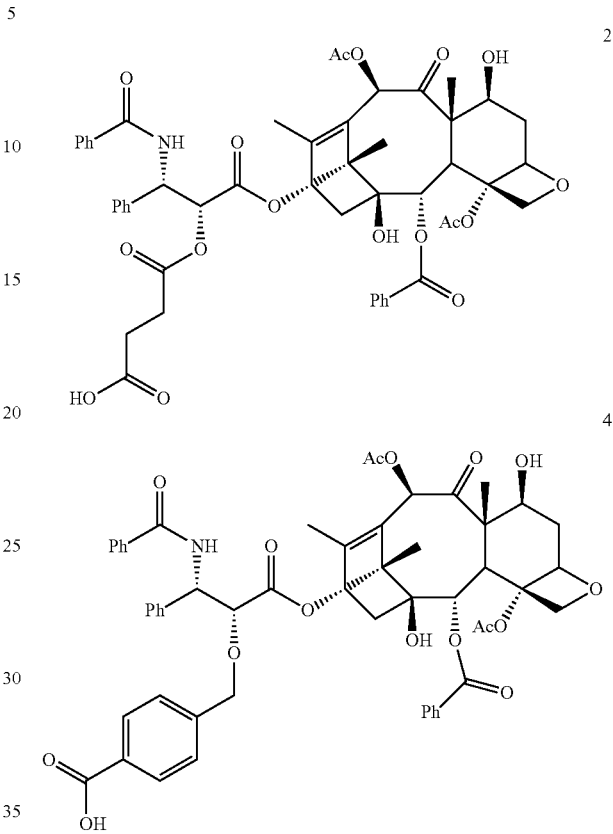

The lysine dendrimer may include approximately 50% and 75% of Taxol terminal groups, which are attached through a variety of "cleavable" linkers.

All lysine dendrimers prepared as the fully Boc protected forms were synthesised and purified according to the procedures described in international patent application WO95/34595, the entire contents of which are incorporated herein by reference. Removal of the Boc protecting group was conducted according to the procedures described in WO95/34595.

Where a lysine dendrimer was required to contain tritium so that the dendrimeric material could be detected in a biological matrix using the technique of scintillation counting, these materials were prepared by diluting (4,5-$^3$H)-L-lysine with non-radioactive L-lysine to provide material with a specific activity in the range of 5uCi to 15uCi per mg. This tritiated lysine was then used to prepare p-Nitrophenol active ester of di-Boc-Lysine which was incorporated into the outer lysine layer of the target lysine dendrimer using the methods described in WO95/34595.

Example 4

Synthesis of BHALys[($^3$H)-Lys]$_8$[D-Lys]$_{16}$[NH$_2$]$_{32}$

To a stirred solution of BHALys[($^3$H)-Lys]$_8$[NH$_2$.TFA]$_{16}$ (38 mg, 0.01 mmol) in dry DMF (3 mL) under nitrogen, was added a solution of D-lysine para-nitrophenol ester (181 mg, 0.38 mmol) in DMF (4 mL) and triethylamine (65 µL, 0.46 mmol). The reaction mixture was allowed to stir at rt for 16 h after which, it was poured into acetonitrile (60 mL) and stirred for 6 h. The resulting fine solid was collected by filtering through a 0.45 μm hydrophilic polypropylene membrane filter and dried over vacuum. The product, BHALys [($^3$H)-Lys]$_8$[D-Lys]$_{16}$[Boc]$_{32}$ was a fine cream coloured solid (40 mg, 56%). BHALys[($^3$H)-Lys]$_8$[D-Lys]$_{16}$[Boc]$_{32}$ (34 mg, 0.005 mmol) was suspended in CH$_2$Cl$_2$ (1 mL) and cooled to 0 C. TFA (398 μL, 2.58 mol) was added dropwise and the reaction was left to stir at 0 C for 10 mins and then warmed to rt and stirred for a further 3 hours. The solvent was removed under vacuum and ether was added to the resulting oil, triturating the solution resulted in crashing out of a white solid. The ether was decanted off and the solid was rinsed with ether (x3). After the ether was removed, the resulting solid was dissolved in a minimum amount of water and applied to an Amberlyst (A-26 OH) ion-exchange column. 100 mL of water was collected from the column and removed by freeze drying to give BHALys[($^3$H)-Lys]$_8$[D-Lys]$_{16}$[NH$_2$]$_{32}$ as a white solid (15 mg, 79%).

LC-MS: (Philic TFA, desolvation temp. 300 C) Rf (min) 8.45. ESI (+ve) m/z=1386.6 (M/3), 1040.3 (M/4), 832.3 (M/5) 694.0 (M/6) 594.9 (M/7).

Example 5

Plasma Clearance and Biodistribution Studies of Cationic Dendrimers

Materials

Buffer reagents were AR grade. Water was obtained from a MilliQ water purification system (Millipore, Australia). Heparin (10,000 IU/mL) was obtained from Faulding, Australia. Saline for injection was obtained in 100 mL polyethylene bags from Baxter Healthcare Pty Ltd (NSW, Australia). Tritiated L-lysine (1 mCi/ml) was purchased from MP Biomedicals (Irvine, Calif., USA). Non-radiolabelled L-lysine was obtained from Sigma Chemical Co (St Louis, Mo., USA). Starscint scintillation cocktail and Soluene-350 tissue solubiliser were purchased from Packard Biosciences (Meriden, Conn.). Protein standards included blue dextran 2000 (2000 kDa), fatty acid free bovine serum albumin (67 kDa), pepsin (35 kDa), trypsin (23.8 kDa), myoglobin (17.6 kDa), ribonuclease A (13.7 kDa), cytochrome C (12.4 kDa) and vitamin B12 (1.4 kDa) and were all obtained from Sigma Chemical Co (St Louis, Mo., USA). Elution times for higher molecular weight proteins were obtained by injection of 20 μl Precision Plus protein standard onto the column (Bio-Rad, Hercules, Calif., USA).

$^3$H-labelled dendrimers were prepared and provided as freeze dried powders. Purification prior to supply was via ultrafiltration and size exclusion chromatography (Sephadex LH20, eluted with water), with ion exchange being utilised to provide the free base form of the uncapped, amine-terminated dendrimers. Purity was ascertained by capillary electrophoresis, NMR and mass spectrometry. The specific activity and molecular weight of the dendrimers are listed in Table 5.

TABLE 5

Selected properties of the dendrimers used in this study

| Dendrimer | Charge | Molecular mass | Specific activity (μCi/mg, mean ± s.d., n = 3) |
|---|---|---|---|
| BHALys [Lys]$_8$ [NH$_2$]$_{16}$ | +16 | 2106 | 0.531 ± 0.012 |
| BHALys [Lys]$_{16}$ [NH$_2$]$_{32}$ | +32 | 4156 | 0.422 ± 0.012 |
| BHALys [Lys]$_8$ [D-Lys]$_{16}$ [NH$_2$]$_{32}$ | +32 | 4156 | 4.186 ± 0.087 |

$^3$H-L-lysine (25 μCi) was freshly diluted with non-radiolabelled lysine in phosphate-buffered saline (PBS, pH 7.4) to a final specific activity of 20 μCi/mg for IV dosing.

All dendrimers were diluted in PBS and frozen at −20° C. until used.

Activity Determinations and Scintillation Counting

The specific activity of the dendrimers was determined in triplicate by dilution of stock solutions containing known mass into PBS. An aliquot was subsequently added to 1 mL of Starscint and scintillation counted on a Packard Tri-Carb 2000CA Liquid Scintillation Analyser (Meriden, Conn.). The average of the triplicate determinations was used for all subsequent calculations.

In Vivo Methods

All animal experimentation protocols were approved by the Victorian College of Pharmacy Animal Ethics Committee, Monash University, Parkville, VIC, Australia.

Intravenous Pharmacokinetic Studies

Prior to dendrimer administration, rats (male, Sprague Dawley, 250-350 g) had cannulas (polyethylene tubing 0.96× 0.58 mm, Paton Scientific, Victor Harbour, Australia) inserted into the jugular vein and carotid artery, under isoflurane anaesthesia as described in Ali et al (1999) J. Biol. Chem. 274: 24066-24073. The cannulas were flushed with heparinised saline (2 I.U. per ml) and flame sealed before insertion into a subcutaneous pocket at the back of the neck during recovery. The rats were allowed to recover overnight prior to dosing, although food was withheld for 12 hr prior to dosing. After the recovery period rats were housed in metabolic cages to permit separate collection of urine and faeces, and the cannulas attached to a swivel/leash assembly to facilitate drug administration and blood collection. Free access to water was allowed at all times. The dendrimers or L-lysine were dissolved in 1 ml of phosphate buffered saline (PBS) and administered at a dose of 5 mg/kg by intravenous infusion over 2 min via the indwelling jugular cannula. The cannula was then flushed with 0.25 ml of heparinised saline to ensure complete infusion of the dose. Blood samples (0.15 ml) were subsequently obtained from the carotid artery at the following nominal time points: prior to dosing (−5 min), at the instant of conclusion of infusion (t=0) and at 5, 10, 20, 30, 45, 60, 90, 120, 180, 240, 360, 480, 1440 and 1800 min. Blood samples were placed immediately into tubes containing 10 I.U. of heparin and centrifuged for 5 min at 3500×g. Plasma (50 μl) was then added to 1 ml of Starscint scintillation cocktail and vortexed before scintillation counting. The limit of quantitation for the plasma assay (20 dpm) was validated using replicate (n=5) analyses of spiked plasma samples. Accuracy and precision were within ±20%.

Biodistribution Studies

In order to understand the fate of dendrimers in vivo, the biodistribution to various major organs was investigated. On completion of the pharmacokinetic studies (30 hr), animals were sacrificed by injection of a lethal dose of sodium pentobarbital and the following tissues removed by dissection: heart, lungs, liver, spleen, pancreas, kidneys and brain. The tissues were stored frozen (−20° C.) in pre-weighed polypropylene tubes until immediately prior to tissue treatment and analysis.

Tissues were initially treated by homogenising the sample in a Waring mini-blender (Extech Equipment Pty. Ltd., Boronia, Australia) with 5-10 ml of MilliQ water for 5×10 sec intervals. In developing a method to measure the relatively low levels of radioactivity in the tissue samples, problems were encountered with chemiluminescence reactions and colour quenching, leading to highly variable background counts on scintillation counting. These problems also appeared to be exacerbated by increases in temperature, exposure to light, and agitation of the samples. In order to overcome these problems the subsequent treatment of the tissues was conducted as a two stage process.

An initial 'screening' stage was used to determine the approximate levels of radioactivity in the samples. For this stage a single sample from each tissue homogenate (typically 40-100 mg of tissue) was placed into a 20 ml polypropylene scintillation vial containing 2 ml of Soluene and tissue digestion allowed to occur at 60° C. overnight. Isopropanol (2 ml) was then added and the solution heated for a further 2 hr at 60° C. On cooling to room temperature, 2×100 μl aliquots of hydrogen peroxide (30% w/v) were added sequentially to the samples, which were then allowed to stand at room temperature until bubbling had ceased. Starscint (12 ml) was then added and the mixture vortexed before storing the samples at 4° C. for 96 hr in the dark without agitation. The samples were then scintillation counted, during which time the counter was maintained at 12° C. using a cooled sample tray. Samples were also counted in sets of six to twelve to minimise warming during counting. Single samples were also taken from organs from untreated rats and processed in a similar manner to obtain a value for background counts expected due to the processing method alone. These values were subtracted from the values obtained during the screening stage. The data obtained from this screening stage provided a broad indication of the expected quantities of activity in each sample. This information was required for the final analytical runs.

In the second 'analytical' stage of the tissue counting process, tissue samples were analysed in triplicate. Blank tissues from untreated rats were also processed as above (albeit in triplicate) to provide for background correction. Homogenised tissues from dendrimer-dosed rats were in general processed in an identical fashion to that described in the screening stage above, except that additional steps were taken to correct for any reduction in radioactivity counting efficacy (quench) due to the "extraction" process from the tissue. To allow correction for counting efficiency, an identical second set of tissues from treated rats was processed in the same way but was initially spiked with a known quantity of radiolabelled dendrimer prior to addition of Soluene. Tissues were spiked with activity at a level approximately equivalent to that measured in the screening samples (hence the need for the screening data). A processing efficiency was then calculated as below, where $$\text{Efficiency} = \frac{\text{Spiked } tissue_{DPM} - Tissue_{DPM,uncorr}}{\text{Spiked } soln_{DPM}} \quad (1)$$

Spiked $tissue_{DPM}$ was the mass corrected radioactivity measured in the spiked samples, $Tissue_{DPM,uncorr}$ was the mass corrected radioactivity in the tissue samples which has not had an additional radioactivity spike added and Spiked $soln_{DPM}$ was the known amount of additional radioactivity added to the spiked sample. Effectively, the calculation provides an indication of the efficiency of counting, using the known (spiked) amount of radioactivity in each tissue as a reference.

This value for efficiency was then used to correct the $^3H$ content in the processed sample where $$Tissue_{DPM,corr} = \frac{Tissue_{DPM,uncorr}}{\text{Efficiency}} \quad (2)$$

The activity in the whole organ was then calculated knowing the mass fraction of the entire organ present in the processed sample. The results are expressed as either the percentage of injected dose in the organ at sacrifice, or the percentage of injected dose per gram of tissue. Due to the variability of the process, an LOQ could not be easily determined for each tissue. Instead, triplicate samples resulting in a % CV greater than 20% were either repeated or were classified as below the quantifiable level when reproducible data could not be obtained.

Whole Blood Pharmacokinetics

To determine whole blood pharmacokinetics, separate groups of animals were administered identical quantities of the dendrimer solutions and whole blood samples (150 μl) collected into heparinised Eppendorf tubes at the same nominal time periods as that used for collection of plasma. Duplicate aliquots (50 μl) of each blood sample were added to 2×20 ml scintillation vials. Initially, one vial was untreated while the other was spiked with a known quantity (~300-600 disintegrations per minute (DPM)) of the dendrimer being investigated) to provide whole blood counting efficiency data (as above). The samples were then solubilised in 4 ml of a 1:1 ratio of Soluene-350 and isopropyl alcohol at 60° C. overnight. Samples were subsequently cooled and bleached with 200 μl hydrogen peroxide (30% w/v) before the addition of Starscint (12 ml). Samples were then left at room temperature for 24 hr prior to scintillation counting. The counts obtained from the blood samples were corrected for efficiency by comparison with the data obtained for the spiked sample as described above.

The pharmacokinetic parameters of $^3H$-dendrimers in plasma and whole blood after intravenous administration are shown in Table 6.

TABLE 6

Plasma and whole blood pharmacokinetic parameters after intravenous administration of $^3$H-dendrimers at 5 mg/kg (mean ± s.d., n = 3)

| Dendrimer | $C_p^0$ (μg/ml) | Initial k (h$^{-1}$) | Initial $t_{1/2}$ (min$^{-1}$) | $V_c$ (ml) |
|---|---|---|---|---|
| Plasma | | | | |
| BHALys [Lys]$_8$ [NH$_2$]$_{16}$ | 24.7 ± 6.5 | 12.1 ± 1.0 | 3.5 ± 0.2 | 55.9 ± 11.8 |
| BHALys [Lys]$_{16}$ [NH$_2$]$_{32}$ | 8.4 ± 2.2 | 9.5 ± 0.1 | 4.4 ± 0.4 | 163 ± 34.6 |
| BHALys [Lys]$_8$ [D-Lys]$_{16}$ [NH$_2$]$_{32}$ | 12.4 ± 1.1 | 14.4 ± 0.5 | 3.0 ± 0.0 | 99.4 ± 10.1 |
| Whole blood | | | | |
| BHALys [Lys]$_8$ [NH$_2$]$_{16}$ | 15.0 ± 1.1 | 13.9 ± 2.1 | 3.0 ± 0.5 | 96.1 ± 13.2 |
| BHALys [Lys]$_{16}$ [NH$_2$]$_{32}$ | 8.8 ± 3.4 | 11.7 ± 2.5 | 3.7 ± 0.7 | 190.4 ± 82.2 |

Urine and Faeces

Urine from dendrimer dosed rats was collected over three time intervals: 0-8 hr, 8-24 hr and 24-30 hr post-dosing. A blank urine sample obtained from each rat before dosing was also collected. A 100 μl aliquot of the urine from each time interval was added to 1 ml of Starscint and the mixture vortexed before scintillation counting. After background subtraction, the radiolabel content of the sample was corrected for the total volume of urine collected over that time interval and converted to a percentage of the total administered $^3$H dose.

Faeces were collected into pre-weighed vials and samples homogenised into a slurry by soaking in Milli Q water, prior to drying at 60° C. Six replicate samples (20 mg) of the dried faeces were then separated into two group of n=3 samples. One group of samples was processed without further addition and one group of three samples was spiked with a known quantity of the radioactive dendrimer (approximately 500 DPM) to provide faeces counting efficiency data (as above). The samples were then solubilised using the method described by Lyons et al (2000). Briefly, 2 ml Soluene was added to re-moistened faeces and heated overnight at 60° C. A further 2 ml of isopropyl alcohol was then added and the samples heated for a further 2 hr. The solubilised samples were then bleached with 400 μl of hydrogen peroxide (30% w/v) prior to addition of 12 ml Starscint. Samples were then left at room temperature for 4 days, prior to cooling at 4° C. for 24 hr and subsequent scintillation counting at 12° C. The total amount of $^3$H excreted in faeces was calculated using the total dry weight of faeces collected. The LOQ for the assay was assumed to be 3 times the average counts in blank faeces, since the mass of faeces produced varied widely and therefore determination of a minimum quantifiable number of counts in a certain sample mass was not possible. These results are summarised in Table 7.

TABLE 7

Excretion of $^3$H over 30 hr from rats after intravenous administration of cationic $^3$H-dendrimers at 5 mg/kg (mean ± s.d, n = 3).

| Dendrimer | Total Recovery in Urine (% of injected radiolabel) | Total Recovery in Faeces (% of injected radiolabel) |
|---|---|---|
| BHALys [Lys]$_8$ [NH$_2$]$_{16}$ | 7.5 ± 1.3 | Below LOQ (LOQ = 1.6%) |
| BHALys [Lys]$_{16}$ [NH$_2$]$_{32}$ | 4.0 ± 0.2 | Below LOQ (LOQ = 0.7%) |
| BHALys [Lys]$_8$ [D-Lys]$_{16}$ [NH$_2$]$_{32}$ | 3.9 ± 0.9 | Below LOQ (LOQ = 1.2%) |

Pharmacokinetic Calculations

The concentrations of radiolabel in plasma/whole blood samples were converted to ng equivalent concentrations using the specific activity of the radiolabelled dendrimer. These concentrations have been expressed throughout this paper as ng equivalents/ml, however, this should be viewed with the caveat that this approach assumes that the $^3$H radiolabel remains associated with the intact dendrimer, which as described below is not the case in some instances.

The rate of initial decline in the plasma concentration—time curves was estimated by linear regression of at least 3 points in the initial phase of log-linear plasma concentration versus time plots. The rate constants obtained from these data have been described as 'elimination' rate constants (K), but may not represent the true terminal elimination rate constants since the rapidity of elimination made accurate delineation of distribution and elimination events difficult. The half life of this initial decline was estimated from $t_{1/2}$=0.693/K. In all cases, an estimate of initial distribution volume ($V_c$) was calculated from the dose/$C_p^0$, where $C_p^0$ was the concentration in plasma at t=0, i.e. at the moment of completion of the two minute infusion. More detailed pharmacokinetic evaluation of the data, including identification of a true elimination rate constant and elimination half life, was not possible due to the very rapid initial removal from plasma and unusual profiles at later time points.

Example 6

Size Exclusion Chromatography for Biological Samples from Example 5

Several methods were used to investigate the size of the species present in plasma samples. Firstly, a coarse size separation was performed by eluting plasma samples through a PD10 gel filtration column (Pharmacia) and collecting fractions under gravity. In this method, plasma samples (500 μl) were diluted with 2 ml of PBS prior to application to the top of a pre-equilibrated PD10 column. Fractions (500 μl) were collected manually into microfuge tubes, and 100 μL aliquots added to 1 ml of Starscint prior to scintillation counting. Intact dendrimer and lysine solutions in PBS were also eluted through the column to characterise the retention volumes of the pure components.

To provide more information on the size of the radiolabel-containing species in plasma, an analytical size exclusion column (Superdex Peptide 10/300 GL, Amersham Bioscience) coupled to a Waters 590 HPLC pump (Millipore Corporation, Milford, Mass., USA) was subsequently used to generate more accurate separations. Plasma samples were again diluted in an equal volume of PBS and 100 μl of the mixture injected onto the column. Samples were eluted with PBS containing 0.3 M NaCl (pH 3.5) at 0.5 ml/min, and aliquots collected at one minute intervals using a Gilson FC10 fraction collector (John Morris Scientific Pty. Ltd. VIC, Australia). Aliquots were then mixed with Starscint (3 ml) and analysed by liquid scintillation to determine the radioactivity in each fraction. Intact dendrimer and lysine solutions in PBS were again eluted separately through the column to characterise their retention volumes. Dendrimer and lysine were also incubated in fresh heparinised plasma for one hour and the dendrimer or lysine-plasma mixtures analysed by SEC. This analysis was performed to provide an indication of the possibility that physical interaction of dendrimer or lysine with plasma components may lead to the production of a high MW species in plasma.

To obtain better resolution of the high MW radiolabelled species present in plasma, samples were also analysed using a Superdex 75 HR 10/30 size exclusion column. Aliquots (0.5 ml) were again collected at 1 min intervals, diluted in Starscint (3 ml) and analysed by liquid scintillation counting to determine the radioactivity in each fraction. Protein standards were used to compose a standard curve (linear $R^2=0.9915$) which was used to estimate the molecular masses of the eluting proteins. Protein elution was monitored at 280 nm using a Waters 486 UV detector (Millipore Corporation, Milford, Mass., USA). The void volume of the column was determined using blue dextran 2000.

Example 7

Synthesis of Tritium Labelled Anionic Dendrimers

Preparation of BHALys[$^3$H-Lys]$_{16}$[CO-3,5-Ph(SO$_3$Na)$_2$]$_{32}$

PyBOP (9.56 g, 18.37 mmol) was added to a stirred solution of dendrimer (BHALys[$^3$H-Lys]$_{16}$[NH$_2$.TFA]$_{32}$) (2.12 g, 0.27 mmol) in DMF/DMSO (1:1) (200 mL). A solution of 3,5-disulfobenzoic acid (5.39 g, 19.11 mmol) and diisopropylethylamine (12.2 mL, 70.02 mmol) in DMF/DMSO (1:1) (150 mL) was added gradually. A sticky ppt formed. The ppt was removed, redissolved in DMSO, and returned to the reaction. The mixture was stirred at rt for 16 h. Reaction mixture was poured into water (3.5 L) and filtered through 0.45 micron filter.

Purification was performed by tangential flow filtration on a Centramate (3K membrane, 2 L sample reservoir). After an initial wash with Milli-Q water (18 L) the retentate was washed with three aliquots of 1M sodium carbonate (100 mL) separated by a Milli-Q water wash (1 L), then filtration was continued until filtrate pH was neutral (approx. 20 L). Retentate was conc. in vacuo, and freeze dried to give the desired product as an off/white solid (2.34 g, 61%).

1H nmr (300 MHz, D$_2$O) λ (ppm): 1.0-2.0 (186H); 2.8-3.4 (62H); 4.0-4.4 (31H); 5.9 (1H); 7.0-7.3 (10H); 8.1-8.3 (96H).

LC/MS (Ion Pairing): ESI (−ve) m/z=740.83 ((M−17H)$^{17-}$); 699.94 ((M−18H)$^{18-}$); 662.83 ((M−19H)$^{19-}$); 629.99 ((M−20H)$^{20-}$); 599.53 ((M−21H)$^{21-}$). Data deconvoluted using maximum entropy calculation to give MW=12614 (M−, in the H form) Calculated (H form) (C$_{423}$H$_{513}$N$_{63}$O$_{255}$S$_{64}$) 12612 (M−). Rf (min)=3.14

CE (pH 3):98.6% Rf (min)=10.97
CE (pH 9): 97.6% Rf (min)=12.90

Preparation of BHALys[$^3$H-Lys]$_8$[CO-4-Ph(SO$_3$Na)]$_{16}$

PyBOP (303 mg, 0.58 mmol) was added to a stirred solution of dendrimer (BHALys[$^3$H-Lys]$_8$[NH$_2$.TFA]$_{16}$) (68 mg, 17.3 μmol) in DMF (5 mL). A solution of 4-sulfobenzoic acid, mono sodium salt (124 mg, 0.55 mmol) and diisopropylethylamine (386 μL, 2.22 mmol) in DMSO/DMF (5 mL/10 mL) was added gradually. The mixture was stirred at it for 24 hrs under argon after which was poured into water (200 mL) and filtered through 0.45 micron filter. Purification was performed by tangential flow filtration on a Minimate (1K membrane, 250 mL sample reservoir) which was washed with water (1.5 L). The solvent from the retentate was reduced under pressure. The product redissolved in water (5 mL) and was subjected to a sephadex size exclusion column (LH20, eluent: water) and collected fractions 1 through to 8. The combined fractions were conc. in vacuo, passed through an ion exchange column (69F, Na+), and freeze dried to give the desired product BHALys[$^3$H-Lys]$_8$[CO-4-Ph(SO$_3$Na)]$_{16}$ as a white solid (20 mg, 22%).

1H nmr (300 MHz, D2O) λ (ppm): 1.0-1.9 (90H, CH2); 2.8-3.3 (30H, CH2); 4.0-4.4 (15H, CH); 5.9 (1H, CH); 7.0-7.2 (10H, Ar—H); 7.5-7.8 (64H, Ar—H).

MS (Direct Infusion): ESI (−ve) m/z=5406 (M−H)— (M−, in the sodium form)

Calculated (sodium form) (C215H257N31O79Na16S16) 5404 (M−).

CE (pH 7): 91% Rf (min)=10.51

Preparation of BHALys[$^3$H-Lys]$_{16}$[CO-4-Ph(SO$_3$Na)]$_{32}$

PyBOP (448 mg, 0.86 mmol) was added to a stirred solution of dendrimer (BHALys[$^3$H-Lys]$_{16}$[NH$_2$.TFA]$_{32}$) (100 mg, 13 μmol) in DMSO (8 mL). A solution of 4-sulfobenzoic acid, mono potassium salt (197 mg, 0.82 mmol) and diisopropylethylamine (571 μL, 3.28 mmol) in DMSO (12 mL) was added gradually. The mixture was stirred at it for 24 hrs under argon. The reaction mixture was poured into water (200 mL) and filtered through 0.45 micron filter. Purification was performed by tangential flow filtration on a Stirred Cell (5K membrane, 250 mL sample reservoir) which was washed with water (1.5 L). The solvent from the retentate was reduced under pressure. The product redissolved in water (5 mL), passed through an ion exchange column (69F, Na+), and freeze dried to give the desired product BHALys[Lys]$_{16}$[CO-4-Ph(SO$_3$Na)]$_{32}$ as a white solid (89 mg, 65%).

1H nmr (300 MHz, D2O) λ (ppm): 1.0-1.9 (186H, CH2); 2.8-3.2 (62H, CH2); 4.0-4.4 (31H, CH); 5.9 (1H, CH); 7.0-7.2 (10H, Ar—H); 7.5-7.8 (128H, Ar—H).

MS (Direct Infusion): ESI (−ve) m/z=10756 (M−H)—(M−, in the sodium form)

Calculated (sodium form) (C423H481N63O159Na32S32) 10754 (M−).

CE (pH 9): 98% Rf (min)=12.17

Preparation of BHALys[$^3$H-Lys]$_{16}$[COCH$_2$CH$_2$(CO$_2$Na)]$_{32}$

To a stirred solution of dendrimer (BHALys[$^3$H-Lys]$_{16}$[NH$_2$.TFA]$_{32}$) (32 mg, 4.1 umol) and triethylamine (36 uL, 0.26 mmol) in DMF (5 mL) was added succinic anhydride (26 mg, 0.26 mmol). The mixture was stirred at rt for 24 hrs under argon. Reaction mixture was poured into water (50 mL) and filtered through 0.45 micron filter. Purification was performed by tangential flow filtration on a Minimate (1K membrane, 70 mL sample reservoir). After an initial wash with NaHCO3 (sat) (100 mL) the retentate was washed with water (1.5 L). The solvent from the retentate was reduced under pressure. The product redissolved in water (2 mL), passed through an ion exchange column (69F, Na+), and freeze dried to give the desired product, BHALys[$^3$H-Lys]$_{16}$ [COCH$_2$CH$_2$(CO$_2$Na)]$_{32}$ as a white solid (17 mg, 52%).

1H nmr (300 MHz, D2O) λ (ppm): 1.0-1.8 (186H, CH2); 2.3-2.7 (128H, CH2); 2.9-3.2 (62H, CH2); 4.0-4.2 (31H, CH); 6.0 (1H, CH); 7.1-7.3 (10H, Ar—H).

MS (Direct Infusion): ESI (–ve) m/z=7360 (M–H)— (M–, in the H form)

Calculated (H form) (C327H513N63O127) 7359 (M–).

CE (pH 9): 96% Rf (min)=13.02

TABLE 8

| Dendrimer properties | | | |
|---|---|---|---|
| Dendrimer | Charge | MW | Specific activity (µCi/mg) mean ± s.d., n = 3 |
| BHALys [$^3$H-Lys]$_8$ [CO-4-Ph(SO$_3$Na)]$_{16}$ | 16 | 5404 | 0.109 ± 0.001 |

TABLE 8-continued

| Dendrimer properties | | | |
|---|---|---|---|
| Dendrimer | Charge | MW | Specific activity (µCi/mg) mean ± s.d., n = 3 |
| BHALys [$^3$H-Lys]$_{16}$ [CO-4-Ph(SO$_3$Na)]$_{32}$ | 32 | 10748 | 0.176 ± 0.006 |
| BHALys [$^3$H-Lys]$_{16}$ [CO-3,5-Ph(SO$_3$Na)$_2$]$_{32}$ | 64 | 14019 | 0.098 ± 0.001 |
| BHALys [$^3$H-Lys]$_{16}$ [COCH$_2$CH$_2$(CO$_2$Na)]$_{32}$ | 32 | 8062 | 2.765 ± 0.017 |

Example 8

Plasma Clearance and Biodistribution Studies of Anionic Dendrimers

The methods used in this study were identical to those used in Example 5.

Plasma concentration-time profile of BHALys[Lys]$_8$[CO-4-Ph(SO$_3$Na)]$_{16}$ (closed circle), BHALys[Lys]$_{16}$[CO-4-Ph(SO$_3$Na)]$_{32}$ (open circle) and BHALys[Lys]$_{16}$[CO-3,5-Ph(SO$_3$Na)$_2$]$_{32}$ (triangle) after 5 mg/kg IV dosing to rats is illustrated in FIG. 10.

TABLE 9

Plasma pharmacokinetic parameters for anionic dendrimers following IV dosing

| Dendrimer | Terminal t½ (hr) | Total AUC (µg/mL · hr) | $V_c$ (ml) | $VD_{ss}$ (ml) | Cl (mL/hr) |
|---|---|---|---|---|---|
| BHALys [Lys]$_8$ [CO-4-Ph(SO$_3$Na)]$_{16}$ | 0.9 ± 0.2 | 65 ± 18 | 13.9 ± 2.7 | 20.2 ± 0.8 | 21.4 ± 4.1 |
| BHALys [Lys]$_{16}$ [CO-4-Ph(SO$_3$Na)]$_{32}$ | 0.9 ± 0.2 | 219 ± 46 | 12.8 ± 3.6 | 10.7 ± 2.9 | 6.4 ± 1.6 |
| BHALys [Lys]$_{16}$ [CO-3,5-Ph(SO$_3$Na)$_2$]$_{32}$ | 1.0 ± 0.1 | 190 ± 35 | 14.3 ± 2.2 | 10.9 ± 2.0 | 7.2 ± 1.4 |
| BHALys [Lys]16 [CO-CH2CH2(CO2Na)]32 | N/A | N/A | 48.8 ± 12.6 | N/A | N/A |

TABLE 10

% of injected $^3$H excreted in urine per time following IV dosing of anionic dendrimers to rats.

| Dendrimer | 0-8 hr (% $^3$H injected) | 8-24 hr (% $^3$H injected) | 24-30 hr (% $^3$H injected) | Total urine (% $^3$H injected) |
|---|---|---|---|---|
| BHALys [Lys]$_8$ [CO-4-Ph(SO$_3$Na)]$_{16}$ | 6.1 ± 0.8 | 15.3 ± 5.6 | 4.0 ± 3.5 | 25.4 ± 8.2 |
| BHALys [Lys]$_{16}$ [CO-4-Ph(SO$_3$Na)]$_{32}$ | 4.5 ± 4.3 | 21.6 ± 4.3 | 4.3 ± 1.0 | 30.4 ± 6.8 |
| BHALys [Lys]$_{16}$ [CO-3,5-Ph(SO$_3$Na)$_2$]$_{32}$ | 0.4 ± 0.3 | 2.7 ± 3.6 | 0 | 3.0 ± 4.1 |
| BHALys [Lys]16 [CO-CH2CH2(CO2Na)]32 | 49.4 ± 13.1 | 12.6 ± 5.0 | 1.6 ± 1.5 | 63.7 ± 9.0 |

Biodistribution of injected $^3H$ 30 hours after IV dosing of BHALys[Lys]$_8$[CO-4-Ph(SO$_3$Na)]$_{16}$ (black), BHALys[Lys]$_{16}$[CO-4-Ph(SO$_3$Na)]$_{32}$ (light grey), BHALys[Lys]$_{16}$[CO-3,5-Ph(SO$_3$Na)$_2$]$_{32}$ (dark grey) or BHALys[Lys]$_{16}$[CO—CH$_2$CH$_2$(CO$_2$Na)]$_{32}$ (white) to rats illustrated in FIG. 11. Panel A—% of injected $^3H$ present per organ. Panel B—% of injected $^3H$ present per gram of tissue.

Example 9

Size Exclusion Chromatography for Biological Samples from Example 8

The methods used in this study were the same as for Example 6.

Size exclusion profiles of BHALys[Lys]$_{16}$[CO-4-Ph(SO$_3$Na)]$_{32}$ and BHALys[Lys]$_{16}$[CO-3,5-Ph(SO$_3$Na)$_2$]$_{32}$ in plasma and urine on a superdex 75 column is illustrated in FIG. 12.

Example 10

Synthesis of Tritium Labelled PEG Dendrimers

Preparation of BHALys[$^3$H-Lys]$_8$[PEG$_{200}$]$_{16}$

To a stirred solution of BHALys[$^3$H-Lys]$_8$[NH$_2$.TFA]$_{16}$ (125 mg, 0.03 mmol) in DMF (8 mL) was added PyBOP (556 mg, 1.0 mmol), followed by a solution of PEG 200 (240 mg, 1.0 mmol), N,N-diisopropylethylamine (709 μL, 4.0 mmol) in DMF (16 mL) and DMSO (2 mL). The solution was stirred at room temperature for 16 h. The reaction mixture was poured into water (180 mL) and filtered and washed with water. The aqueous solution was transferred to a 3K stirred cell and water was passed through the cell, remaining water was removed by freeze drying to give BHALys[$^3$H-Lys]$_8$[PEG$_{200}$]$_{16}$ as a free flowing white solid (20 mg, 11%)

LC/MS (Philic TFA): Rf (min)=16.72. ESI (+ve) m/z=5598 (M+H$^+$).

Preparation of BHALys[$^3$H-Lys]$_{16}$-[PEG$_{200}$]$_{32}$

To a stirred solution of BHALys[$^3$H-Lys]$_{16}$[NH$_2$.TFA]$_{32}$ (30 mg, 0.004 mmol) in DMF (3 mL) under argon was added PyBOP (142 mg, 0.271 mmol), followed by a solution of PEG 200 (62 mg, 0.263 mmol), N,N-diisopropylethylamine (182 μL, 1.04 mmol) in DMF (3 mL). The solution was stirred at room temperature for 16 h. The solvents were removed under reduced pressure and the resulting crude mixture was dissolved in a minimum volume of water. Purification by sephadex column (LH-20) using water as the eluent gave the desired product BHALys[$^3$H-Lys]$_{16}$[PEG$_{200}$]$_{32}$ as a white solid (20 mg, 44%) after removing the water by freeze drying.

LC/MS (Philic TFA): Rf (min)=16.74 ESI (+ve) m/z=11, 141 (M+H$^+$).

Preparation of BHALys[$^3$H-Lys]$_{16}$[PEG$_{570}$]$_{32}$

To a stirred solution of BHALys[$^3$H-Lys]$_{16}$[NH$_2$.TFA]$_{32}$ (20 mg, 0.003 mmol) in dry DMF (2 mL) under nitrogen was added triethylamine (36 μL, 0.261 mmol) and PEG 685.75, NHS ester (119 mg, 0.174 mmol). The reaction mixture was stirred at room temperature for 16 h. The solution was poured into a 5K stirred cell and water (600 mL) was passed through the cell, remaining water was removed by freeze drying (x2) to give BHALys[$^3$H-Lys]$_{16}$[PEG$_{570}$]$_{32}$ as a glassy solid (50 mg, 88%). LC (Philic TFA): Rf (min) 12.42.

Preparation of BHALys[$^3$H-Lys]$_8$[PEG$_{2KD}$]$_{16}$

To a stirred solution of BHALys[$^3$H-Lys]$_8$[NH$_2$.TFA]$_{16}$ (30 mg, 0.008 mmol) in dry DMF (2 mL) under nitrogen was added PyBOP (141 mg, 0.271 mmol), followed by a solution of PEG 2000, NHS ester (612 mg, 0.306 mmol), N,N-diisopropylethylamine (180 μL, 1.04 mmol) in DMF (1.4 mL) and DMSO (0.6 mL). The solution was stirred at room temperature for 16 h. The reaction mixture was poured into a 10K stirred cell and water (800 mL) was passed through the cell, remaining water was removed by freeze drying to give BHALys[$^3$H-Lys]$_8$[PEG$_{2KD}$]$_{16}$ as a free flowing white solid (149 mg, 54%).

Preparation of BHALys[$^3$H-Lys]$_{16}$[PEG$_{2KD}$]$_{32}$

To a stirred solution of BHALys[$^3$H-Lys]$_{16}$[NH$_2$.TFA]$_{32}$ (30 mg, 0.004 mmol) in dry DMF (2 mL) under argon was added PyBOP (142 mg, 0.272 mmol), followed by a solution of PEG 2000, NHS ester (522 mg, 0.261 mmol), N,N-diisopropylethylamine (182 μL, 1.04 mmol) in DMF (3 mL) and DMSO (1 mL). The solution was stirred at room temperature for 16 h. The reaction mixture was poured into water and filtered and washed with water. Purification was performed by tangential flow filtration on a Mini-mate (10K membrane, 2 L of water). Solvent was removed by freeze drying to give BHALys[$^3$H-Lys]$_{16}$[PEG$_{2KD}$]$_{32}$ as a free flowing white solid (210 mg, 76%)

LC/MS (Philic TFA): Rf (min)=16.29 ESI (+ve) m/z=67, 696 (M+H$^+$)

TABLE 11

| | Dendrimer properties | | | | |
|---|---|---|---|---|---|
| | BHALys [Lys]$_8$ [PEG$_{200}$]$_{16}$ | BHALys [Lys]$_{16}$ [PEG$_{200}$]$_{32}$ | BHALys [Lys]$_{16}$ [PEG$_{570}$]$_{32}$ | BHALys [Lys]$_8$ [PEG$_{2000}$]$_{16}$ | BHALys [Lys]$_{16}$ [PEG$_{2000}$]$_{32}$ |
| MW (kDa) | 6 | 11.1 | 22.4 | 34.1 | 67 |
| $^3H$ (μCi/mg) | 0.134 ± 0.007 | 2.195 ± 0.022 | 1.012 ± 0.028 | 0.623 ± 0.019 | 0.469 ± 0.022 |

Example 11

Plasma Clearance and Biodistribution Studies of PEG Dendrimers

The methods used in this study were identical to those used in Example 5.

TABLE 12

Dendrimer pharmacokinetic parameters

| | BHALys [Lys]$_8$ [PEG$_{200}$]$_{16}$ | BHALys [Lys]$_{16}$ [PEG$_{200}$]$_{32}$ | BHALys [Lys]$_{16}$ [PEG$_{570}$]$_{32}$ | BHALys [Lys]$_8$ [PEG$_{2000}$]$_{16}$ | BHALys [Lys]$_{16}$ [PEG$_{2000}$]$_{32}$ |
|---|---|---|---|---|---|
| $C_p^0$ (µg/ml) | 57.4 ± 4.5 | 70.4 ± 3.3 | 90.8 ± 5.3 | 70.8 ± 2.5 | 83.2 ± 15.3 |
| $K_{el}$ ($^{-h}$) | 2.85 ± 0.42 | 0.39 ± 0.03 | 0.073 ± 0.003 | 0.029 ± 0.003 | 0.0093 ± 0.0013 |
| $t_{1/2}$ (h) | 0.6 ± 0.1 | 1.8 ± 0.1 | 9.5 ± 0.3 | 23.9 ± 2.1 | 75.4 ± 9.3 |
| $V_c$ (ml) | 26.1 ± 3.6 | 18.6 ± 0.9 | 14.8 ± 0.4 | 18.0 ± 0.4 | 19.1 ± 3.1 |
| Fe | 0.82 ± 0.06 | 0.80 ± 0.14 | 0.43 ± 0.03 | 0.26 ± 0.05 | 0.03 ± 0.02 |
| Cl (ml/h) | 208 ± 0.8 | 108 ± 5.9 | 4.8 ± 0.7 | 0.9 ± 0.1 | 0.4 ± 0.1 |
| Cl$_r$ (ml/h) | 170 ± 13.5 | 87.5 ± 18.9 | 2.07 ± 0.41 | 0.24 ± 0.03 | 0.01 ± 0.01 |
| Cl$_{nr}$ (ml/h) | 37.1 ± 13.3 | 20.8 ± 13.2 | 2.73 ± 0.34 | 0.68 ± 0.11 | 0.37 ± 0.09 |
| $K_e$ ($^{-h}$) | 2.35 ± 0.46 | 0.31 ± 0.05 | 0.032 ± 0.003 | 0.008 ± 0.001 | 0.0003 ± 0.0002 |
| $V_{DSS}$ (ml) | 62.1 ± 11.8 | 66.5 ± 11.8 | 42.0 ± 7.8 | 26.4 ± 0.9 | 34.9 ± 11.5 |

Plasma concentration-time profiles for BHALys[Lys]$_{16}$[PEG$_{200}$]$_{32}$ (closed circles), BHALys[Lys]$_{16}$[PEG$_{570}$]$_{32}$ (open circles), BHALys[Lys]$_8$[PEG$_{2000}$]$_{16}$ (closed triangles) and BHALys[Lys]$_{16}$[PEG$_{2000}$]$_{32}$ (open triangles) illustrated in FIG. 13. Data for BHALys[Lys]$_8$[PEG$_{200}$]$_{16}$ not shown as elimination is extremely rapid and obscured by the data for BHALys[Lys]$_{16}$[PEG$_{200}$]$_{32}$ Biodistribution of BHALys[Lys]$_{16}$[PEG$_{2000}$]$_{32}$ (black bars, 7 days), BHALys[Lys]$_8$ [PEG$_{2000}$]$_{16}$ (grey bars, 5 days) and BHALys[Lys]$_{16}$[PEG$_{570}$]$_{32}$ (white bars, 30 hours) after IV dosing illustrated in FIG. 14.

Example 12

Size Exclusion Chromatography for Biological Samples from Example 11

The methods used in this study were the same as for Example 6.

Size exclusion profiles for $^3$H-labelled BHALys[Lys]$_{16}$[PEG$_{200}$]$_{32}$ (Panel A; t0, open square, t=1 h, closed circles, t=4 h, open circles), BHALys[Lys]$_{16}$[PEG$_{570}$]$_{32}$ (Panel B; 24 h), BHALys[Lys]$_8$[PEG$_{200}$]$_{16}$ (Panel C; 48 h) and BHALys[Lys]$_{16}$[PEG$_{2000}$]$_{32}$ (Panel D; 48 h) in plasma after a 5 mg/kg IV dose on a Superdex 75 column are illustrated in FIGS. 15A-D.

Size exclusion profiles of $^3$H excreted in urine after IV dosing of BHALys[Lys]$_{16}$ [PEG$_{200}$]$_{32}$ (Panel A; 0-4 h urine, closed circles, 8-24 h urine, open circles) and BHALys[Lys]$_{16}$[PEG$_{570}$]$_{32}$ (Panel B; 8-24 h urine) are illustrated in FIGS. 16A and B. Arrows indicate the retention time of the intact dendrimer.

Summary

The applicants have carried out a study of $^3$H-labelled poly-L-lysine dendrimers (, where both BHALys[Lys]$_8$[NH$_2$]$_{16}$ or BHALys[Lys]$_{16}$[NH$_2$]$_{32}$ have been prepared and the surfaces left uncapped. By way of comparison, a third dendrimer consisting of the BHALys[Lys]$_8$[NH$_2$]$_{16}$ core capped entirely with D-lysine, forming a Lys$_{16}$ dendrimer with D-lysine at its outer layer BHALys[Lys]$_8$[D-Lys]$_{16}$[NH$_2$]$_{32}$ has also been examined.

In all cases, the dendrimers were covered with cationic amine groups at physiological pH. The plasma clearance and biodistribution was determined for these materials (Example 5). The in vivo fate of the $^3$H dendrimers was further studied by separation of the different radiolabelled species present in plasma using size exclusion chromatography (Example 6). The data suggest that poly-L lysine dendrimers are rapidly removed from plasma after intravenous administration, but are subsequently metabolised and the liberated L-lysine re-incorporated into endogenous resynthetic processes.

After intravenous administration, both BHALys[Lys]$_8$[NH$_2$]$_{16}$ and BHALys[Lys]$_{16}$[NH$_2$]$_{32}$ were very rapidly removed from plasma exhibiting initial plasma half-lives of less than 10 min (FIG. 2). This initial rapid loss was not markedly dependent on dose (FIG. 3), and was also evident when whole blood (as opposed to plasma) profiles were examined (FIG. 4), and when the L-lysine surface groups were changed to D-lysine (FIG. 5). The initial distribution volumes (V$_c$) were surprisingly high for these relatively high molecular weight species, and the V$_c$ of the higher molecular weight generation 4 dendrimers BHALys[Lys]$_{16}$[NH$_2$]$_{32}$ and BHALys[Lys]$_8$[D-Lys]$_{16}$[NH$_2$]$_{32}$ were higher than the smaller generation 3 comparator. The V$_c$ values for the $3^{rd}$ and $4^{th}$ generation dendrimers appear, therefore, to be more highly correlated with surface charge, rather than molecular weight. The data are consistent with the initial 'distribution' process reflecting rapid binding of the poly-cationic dendrimers to the vascular endothelium, in a process driven by electrostatic interactions, leading to loss from the circulating plasma. In contrast, typical extravasation processes seem unlikely since rapid passage across the vascular endothelium would be difficult for such highly charged macromolecules, and would be expected to increase with reductions in molecular weight and surface charge—whereas the opposite was in fact observed. These trends were also evident in the whole blood pharmacokinetics, although in the case of the smaller dendrimer the $C_p^0$ values were approximately two-fold lower (and the corresponding V$_c$ values two fold higher), suggesting that binding of the dendrimers to red blood cells was lower for the less highly charged generation 3 dendrimers.

In summary, the current data have shown that uncapped poly-L-lysine dendrimers are rapidly removed from the plasma on intravenous injection, and that at later time points, radiolabel initially associated with intact dendrimer reappears in the plasma associated with species that co-elute on SEC with free lysine and a number of larger molecular weight (possibly proteinaceous) materials, including albumin. The data also suggest that the highly charged cationic dendrimers rapidly bind to endothelial cell surfaces immediately after injection and are subsequently hydrolysed to produce circulating free lysine, which is itself eventually re-incorporated into protein biosynthetic pathways. These data are, to our knowledge, the first to describe the in vivo biodegradation and resorption of poly-L-lysine dendrimers. Accordingly appropriate manipulation of the surface properties of poly-L-lysine dendrimers may enhance initial residence time in the plasma. The uncapped poly-L-lysine surface may accordingly provide biodegradable and bioresorbable dendrimer-based drug delivery systems.

A separate study has investigated the influence of capping the surface of poly-L-lysine dendrimer cores with anionic arylsulphonate groups or alkyl carboxylate groups on dendrimer pharmacokinetics and biodistribution patterns after intravenous administration to rats.

Two different sized dendrimer cores BHALys[Lys]$_8$[NH$_2$]$_{16}$ and BHALys[Lys]$_{16}$[NH$_2$]$_{32}$ with 8 and 16 lysine groups in the outer layer respectively) capped with benzene sulphonate (CO-4-Ph(SO$_3$Na)) or benzene disulphonate (CO-3,5-Ph(SO$_3$Na)$_2$) terminal groups were utilized to facilitate discrimination of the influence of dendrimer size and surface charge (Synthesis Example 7). Four tritium labelled lysine dendrimers BHALys [Lys]$_8$[CO-4-Ph(SO$_3$Na)]$_{16}$; BHALys[Lys]$_{16}$[CO-4-Ph(SO$_3$Na)]$_{32}$; BHALys[Lys]$_{16}$[CO-3,5-Ph(SO$_3$Na)$_2$]$_{32}$ and BHALys[Lys]$_{16}$[CO—CH$_2$CH$_2$(CO$_2$Na)]$_{32}$ were administered intravenously (5 mg/kg), and the radioactivity in plasma, urine and faeces monitored over 30 hours (Example 8). Animals were sacrificed 30 hours after dosing and the major organs removed, homogenised and assayed for radiolabel.

The plasma concentration-time profiles indicated that the plasma clearance and volume of distribution of BHALys[Lys]$_8$[CO-4-Ph(SO$_3$Na)]$_{16}$ was higher than that of the Lys$_{16}$ dendrimers, although the elimination half lives for all four dendrimers were essentially the same (approximately 1 hour). Approximately 30% of the injected radiolabel associated with the BHALys[Lys]$_8$[CO-4-Ph(SO$_3$Na)]$_{16}$ and BHALys[Lys]$_{16}$[CO-4-Ph(SO$_3$Na)]$_{32}$ dendrimers was excreted in urine in the 30 h post dose period, whereas only 3% of the dose of the highly charged BHALys[Lys]$_{16}$[CO-3,5-Ph(SO$_3$Na)$_2$]$_{32}$ was eliminated into the urine over the same time period.

The clearance profile for the succinate dendrimer was significantly different to that of the other anionic dendrimers and the succinate dendrimer was very rapidly removed from plasma on intravenous injection. The initial distribution volume (Vc) was also higher than that of the other anionic dendrimers and approaching that of the cationic dendrimers, suggesting an initial interaction with a blood component or endothelial surface that rapidly removed radiolabel from the plasma (FIG. 4). The initial rate of loss over the first 20 min in the plasma was also very rapid and again took place over a similar time scale to that seen with the cationic dendrimers. After the initial rapid decline the radiolabel appeared to be cleared more slowly, with quantifiable amounts of radiolabel remaining 30 hr after dosing. It is unknown whether the second slower rate of removal reflects the redistribution of label back into the plasma as was seen previously with the cationic system. The anionic dendrimers appeared to be almost entirely excluded from red cells. In contrast to the other anionic dendrimers, most of the injected radiolabel associated with the succinate dendrimer was excreted in urine (63.71±8.98%), while a very small but quantifiable amount of radiolabel was recovered in pooled faeces (1.21±0.97%) (Table 3).

Size exclusion chromatography of plasma samples from BHALys[Lys]$_{16}$[CO-4-Ph(SO$_3$Na)]$_{32}$ and BHALys[Lys]$_{16}$[CO-3,5-Ph(SO$_3$Na)$_2$]$_{32}$ dosed rats revealed that both anionic dendrimers rapidly bound to plasma components, forming a high molecular weight species (<67 kDa). Whilst no breakdown products were identified in plasma, radiolabel in the urine was primarily associated with a species with a molecular weight approximating that of a Lys-arylsulphonate monomer. Interestingly radiolabel in urine was mostly excreted over a timescale (8-24 h post dose) during which the plasma radioactivity levels were extremely low. Organ deposition patterns revealed that residual radioactivity present 30 h after dosing each of the dendrimers was concentrated primarily in the liver, spleen and kidneys. For BHALys[Lys]$_{16}$[CO-3,5-Ph(SO$_3$Na)$_2$]$_{32}$ recovery of radioactivity was particularly high in the liver (~50% of the dose). The data suggest that after elimination of the benzene sulphonate dendrimers from the plasma, metabolism occurs which subsequently facilitates urinary elimination of the breakdown product. In contrast, the low recovery of radioactivity derived from BHALys[Lys]$_{16}$[CO-3,5-Ph(SO$_3$Na)$_2$]$_{32}$ in the urine may reflect a reduced susceptibility to metabolism, possibly as a result of the increased surface charge density of the dendrimer, which in turn leads to higher recovery in the liver.

Accordingly, the plasma clearance of the anionic dendrimers is slower than that seen previously for the uncapped cationic poly-L-lysine dendrimers. Secondly, within the anionic series, plasma clearance is primarily dictated by dendrimer size, rather than surface charge. Finally surface charge, however, does dictate the patterns of renal elimination and biodistribution, and may result from differences in susceptibility to metabolism of the benzene sulphonate vs benzene disulphonate-capped dendrimers.

PEGylation is known to reduce the recognition of proteins by proteolytic enzymes and suppress the phagocytic clearance of proteins and colloids, thereby prolonging plasma circulation times. As such in the current application the impact of PEGylation (Synthesis Example 10) on the plasma profiles, patterns of biodistribution and urinary elimination of $^3$H-labelled poly-L-lysine dendrimers has been investigated in rats after intravenous administration of 5 mg/kg of dendrimer (PK and Biodistribution Example 11). In general, the plasma half lives and extent of urinary elimination of the PEGylated dendrimers were dependent on molecular weight and larger PEGylated dendrimers (ie. >30 kDa) were relatively slowly cleared from the plasma ($t_{1/2}$ 1-3 days) whilst the smaller species (ie. <20 kDa) were rapidly cleared from the plasma into the urine ($t_{1/2}$ 1-10 h). The larger dendrimers appeared to eventually concentrate in the organs of the reticuloendothelial system (liver and spleen), however this occurred over extended time periods, and the absolute extent of accumulation was low (<10% of the dose). By SEC the dendrimers derivatised with the smallest (200 Da) PEG chains, showed some signs of interaction with plasma components, leading to the creation of an apparently higher molecular weight species, however elimination into the urine was extremely rapid and only intact dendrimer was recovered in the urine. The dendrimers derivatised with the larger PEGylated species (ie. 2000 Da) were present in both plasma and urine as the parent (unchanged) dendrimer. Accordingly the size of PEGylated poly-L-lysine dendrimer complexes may be manipulated to optimally tailor their pharmacokinetics.

Examples of Differentially Protected Intermediates and Partial PEG Structures

Example 15

Preparation of BHALys[Lys]$_8$[α-Boc]$_8$[ε-NH2]$_8$ i. Preparation of BHALys[Lys]$_8$[α-Boc]$_8$[ε-CBz]$_8$ To a magnetically stirred solution of BHALys[Lys]$_4$[NH$_2$.TFA]$_8$ (1.59 mmol), triethylamine (4.50 ml, 32.30 mmol) and DMF (30 ml) was added PNPO-α-Boc-ε-CBz-Lys (7.75 g, 15.45 mmol) as a solid and in one portion at room temperature. The reaction suspension immediately turned bright yellow in colour and after stirring for ca. 5 mins, the active ester had completely dissolved. Stirring was continued at room temperature for a further 22 h. The crude reaction mixture was poured into a large beaker which contained ice-water and a fine yellow precipitate formed. The suspension was filtered and the solids thus retained were air dried under suction overnight. The dry, light yellow coloured cake which resulted was pulverised to a fine powder and re-suspended in acetonitrile. The suspension was stirred at room temperature for 30 mins then filtered. The solids retained were once again air dried, re-pulverised and re-suspended in acetonitrile before being filtered and air dried overnight to give BHALys[Lys]$_8$[α-Boc]$_8$[ε-CBz]$_8$t (5.52 g, 87%) as a colourless solid.

LC/MS (Phobic/TFA): ESI (+ve) observed [M+H/3]+ m/z=1328; calculated for C207H305N31O47 3979.9; Rf (min)=20.22 mins.

ii. Preparation of BHALys[Lys]$_8$[α-Boc]$_8$[ε-NH$_2$]$_8$

BHALys[Lys]$_8$[α-Boc]$_8$[ε-CBz]$_8$ (500 mg, 0.126 mmol) was suspended in 9:1 DMF/H$_2$O (12.5 ml) and ammonium formate (127 mg, 2.01 mmol) was added, and after stirring for 5 mins, Pd/C (10% w/w, 266 mg) was added and stirring was continued for 2 h. The reaction was terminated by filtering off the catalyst and the filter was rinsed with 9:1 DMF/H$_2$O (10 ml) then water (2 ml). The combined filtrates were concentrated in vacuo to give a colourless syrup, which was treated with water (10 ml) which was removed in vacuo, then freeze-dried in water to give BHALys[Lys]$_8$[α-Boc]$_8$[ε-NH$_2$]$_8$ as a fine white lyophilate (155 mg, 42%).

LC/MS (Hydrophilic/TFA): ESI (+ve) m/z=969.83 [M+3H]/3+, 727.67 [M+4H]/4+, 582.39 [M+5H]/5+, calculated (C143H257N31O31) 2906.8 g/mol. Data deconvoluted using transform calculation to give mw=2906.5. Rf (min)=14.7.

Example 16

Preparation of BHALys[Lys]$_8$[α-NH$_2$.TFA]$_8$[ε-CBz]$_8$

BHALys[Lys]$_8$[α-Boc]$_8$[ε-CBz]$_8$ (1000 mg, 0.251 mmol) was suspended in acetic acid (5.5 ml) and stirred at 0° C. while trifluoroacetic acid (5.5 ml) was added dropwise. The reaction mixture was allowed to warm to room temperature and left to stir for 17 h, at which point the reaction mixture was triturated in diethyl ether The resulting suspension was stirred for 10 min, and liquids were removed by centrifugation and decanting. The remaining precipitate was washed by stirring for 10 min with diethyl ether, which was again removed by centrifugation and decanting, then the precipitate was dried in vacuo, dissolved in water and freeze-dried to give BHALys[Lys]$_8$[α-NH$_2$.TFA]$_8$[ε-CBz]$_8$ as a white powder (840 mg, 105%).

LC/MS (Hydrophilic/TFA): ESI (+ve) m/z=1060.70 [M+3H]/3+, 795.51 [M+4H]/4+, 636.30 [M+5H]/5+; calculated (C167H241N31O31) 3178.95 g/mol. Data deconvoluted using transform calculation to give mw=3178.0. Rf (min)=19.1.

Example 17

Preparation of BHALys[Lys]$_{16}$[α-Boc]$_{16}$[ε-NH$_2$]$_{16}$ i. Preparation of BHALys[Lys]$_{16}$[α-Boc]$_{16}$[ε-CBz]$_{16}$ To a stirred solution of BHALys[Lys]$_8$[NH$_2$.TFA]$_{16}$ (0.81 mmol), triethylamine (4.50 ml, 32.30 mmol) and DMF (30 ml) was added PNPO-α-Boc-ε-CBz-Lys (7.94 g, 15.83 mmol) as a solid and in one portion at room temperature. The reaction suspension immediately turned bright yellow in colour and after stirring for ca. 5 mins, the active ester had completely dissolved. Stirring was continued at room temperature for a further 22 h. The crude reaction mixture was poured into a large beaker which contained ice-water and a fine yellow precipitate formed. The suspension was filtered and the solids thus retained were air dried under suction overnight. The dry, light yellow coloured cake which resulted was pulverised to a fine powder and re-suspended in acetonitrile. The suspension was stirred at room temperature for 30 mins then filtered. The solids retained were air dried overnight to give BHALys[Lys]$_{16}$[α-Boc]$_{16}$[ε-CBz]$_{16}$ (5.79 g, 91%) as a colourless solid.

LC/MS (Phobic/TFA): ESI (+ve) observed [M+H/4]+ m/z=1977; [M+H/5]+ m/z=1582; calculated for C407H609N63O95 7904.9; Rf (min)=23.51 mins.

ii. Preparation of BHALys[Lys]$_{16}$[α-Boc]$_{16}$[ε-NH$_2$]$_{16}$

A suspension of BHALys[Lys]$_{16}$[α-Boc]$_{16}$[ε-CBz]$_{16}$ (50 mg, 0.006 mmol), 10% Pd/C (53 mg) and acetic acid (2 ml) was vigorously stirred under hydrogen at room temperature for 16 h. The black suspension was filtered. Concentration of the filtrate in vacuo afforded the product (26 mg, 71%) a straw coloured oil.

LC/MS (Phobic/TFA): ESI (+ve) observed [M+H/5]+ m/z=1152; [M+H/6]+ m/z=961; [M+H/7]+ m/z=824; [M+H/8]+ m/z=721; [M+H/9]+ m/z=641;calculated for C279H513N63O63 5758.53; Rf (min)=2.37 mins.

Example 18

Preparation of BHALys[Lys]$_{16}$[α-NH$_2$.TFA]$_{16}$[ε-CBz]$_{16}$

BHALys[Lys]$_{16}$[α-Boc]$_{16}$[ε-CBz]$_{16}$ (1000 mg, 0.127 mmol) was suspended in acetic acid (5.5 ml) and stirred at 0° C. while trifluoroacetic acid (5.5 ml) was added dropwise. The reaction mixture was allowed to warm to ambient temperature and left to stir for 17 h. The reaction mixture was triturated in diethyl ether (150 ml) and the resulting suspension was stirred for 10 min. Liquids were removed by centrifugation (4000 rpm, 10 min) and decanting, and the remaining precipitate was washed by stirring for 10 min with diethyl ether (150 ml), which was again removed by centrifugation and decanting. The precipitate was dried in vacuo, dissolved in water (50 ml) and freeze-dried to give BHALys[Lys]$_{16}$[α-NH$_2$.TFA]$_{16}$[ε-CBz]$_{16}$ as a white powder (832 mg, 114%).

LC/MS (Hydrophilic/TFA): ESI (+ve) m/z=1576.85 [M+4H]/4+, 1261.34 [M+5H]/5+, 1051.27 [M+6H]/6+, 901.15 [M+7H]/7+; calculated (C327H481N63O63) 6302.83 g/mol. Data deconvoluted using transform calculation to give mw=6301.5. Rf (min)=19.0.

Example 19

Preparation of BHALys[Lys]$_8$[α-NH$_2$]$_8$[ε-Boc]$_8$ i. Preparation of BHALys[Lys]$_8$[α-CBz]$_8$[ε-Boc]$_8$ To a magnetically stirred solution of BHALys[Lys]$_4$[NH$_2$.TFA]$_8$ (1.59 mmol), triethylamine (4.40 ml, 31.57 mmol) and DMF (32 ml) was added PNPO-α-CBz-ε-Boc-Lys (7.69 g, 15.33 mmol) as a solid and in one portion at room temperature. The reaction suspension immediately turned bright yellow in colour and after stirring for ca. 5 mins, the active ester had completely dissolved. Stirring was continued at room temperature for a further 19 h. The crude reaction mixture was poured into a large beaker which contained acetonitrile (ca. 300 ml). The suspension was filtered and the solids thus retained were air dried under suction overnight. The dry, light yellow coloured cake which resulted was pulverised to a fine powder (mortar and pestle) and re-suspended in acetonitrile (400 ml). The suspension was magnetically stirred at room temperature for 60 mins then filtered. The solids retained were once again air dried, re-pulverised and re-suspended in acetonitrile before being filtered and air dried overnight to give BHALys[Lys]$_8$[α-CBz]$_8$[ε-Boc]$_8$ (5.41 g, 85%) as an off-white solid.

LC/MS (Phobic/TFA/Speedy Ramp): ESI (+ve) observed [M+H/3]+ m/z=1328; calculated for C207H305N31O47 3979.9; Rf (min)=12.98 mins ii. Preparation of BHALys[Lys]$_8$[α-NH$_2$]$_8$[ε-Boc]$_8$ BHALys[Lys]$_8$[α-CBz]$_8$[ε-Boc]$_8$ (5.0 mg, 1.26 μmol) was suspended in 9:1 DMF/H$_2$O (2 ml), stirring at ambient temperature, and ammonium formate (2.5 mg, 40.2 μmol) was added, followed by Pd/C (10% w/w, 2.7 mg) was added and stirring was continued for 20 h. The reaction was terminated by filtering off the catalyst and the filter was rinsed with 9:1 DMF/H$_2$O (1 ml). The filtrate was concentrated in vacuo to give a colourless syrup, which was treated with water (1 ml) which was removed in vacuo, then freeze-dried in water (1 ml) to give BHALys[Lys]$_8$[α-NH$_2$]$_8$[ε-Boc]$_8$ as a fine white lyophilate (2 mg, 42%).

LC/MS (Hydrophilic/TFA): ESI (+ve) m/z=969.88 [M+3H]/3+, 727.56 [M+4H]/4+; calculated (C143H257N31O31) 2906.8 g/mol. Data deconvoluted using transform calculation to give mw=2906.5. Rf (min)=17.2.

Example 20

Preparation of BHALys[Lys]$_8$[α-CBz]$_8$[ε-NH$_2$.TFA]$_8$

BHALys[Lys]$_8$[α-CBz]$_8$[ε-Boc]$_8$ (20.0 mg, 0.005 mmol) was suspended in acetic acid (109 μl) and stirred in water bath. Trifluoroacetic acid (109 μl) was added carefully, to dissolve all solid material, and stirring was continued at ambient temperature for 16 h. The reaction was terminated by removing all volatiles in vacuo, giving a clear, colourless oil. This oil was triturated in diethyl ether and the resulting white precipitate was washed with diethyl ether, and dried in vacuo to give BHALys[Lys]$_8$[α-CBz]$_8$[ε-NH$_2$.TFA]$_8$ (12.1 mg, 76%) as a white solid.

LC/MS (Hydrophilic/TFA): ESI (+ve) m/z=1060.43 [M+3H]/3+, 795.63 [M+4H]/4+, 636.79 [M+5H]/5+; calculated (C167H241N31O31) 3178.95 g/mol. Data deconvoluted using transform calculation to give mw=3179.25. Rf (min)=16.6.

Example 21

Preparation of BHALys[Lys]$_{16}$[α-NH$_2$]$_{16}$[ε-Boc]$_{16}$ i. Preparation of BHALys[Lys]$_{16}$[α-Fmoc]$_{16}$[ε-Boc]$_{16}$ To a stirred solution of BHALys[Lys]$_8$[NH$_2$.TFA]$_{16}$ (0.54 mmol), DIPEA (3.0 ml, 17.22 mmol) and DMF (11 ml) was added pentafluorophenyloxy-α-Fmoc-ε-Boc-Lys (6.58 g, 10.36 mmol) as a solid and in one portion at room temperature. The reaction suspension immediately turned bright yellow in colour and after stirring for ca. 10 mins, the active ester had completely dissolved. Stirring was continued at room temperature for a further 18 h. After this time, the crude reaction mixture had become so thick that magnetic stirring could no longer continue. Acetonitrile (ca. 300 ml) was added to the reaction flask and, with the aid of a spatula, the solid mass was broken up sufficiently so as to allow stirring to resume (1 hr). The suspension was filtered and allowed to air dry under vacuum overnight. The resulting near colourless cake was pulverised with a mortar and pestle and the fine solid was re-suspended in acetonitrile (500 ml) for 2 hrs. After this time, the suspension was filtered and the colourless solid was collected and air dried overnight at rt. The desired product was obtained as an off-white solid (4.72 g, 94%). This product was characterised as the Fmoc deprotected derivative BHALys [Lys]$_{16}$[α-NH$_2$]$_{16}$[ε-Boc]$_{16}$ (see ii).

ii. Preparation of BHALys[Lys]$_{16}$[α-NH$_2$]$_{16}$[ε-Boc]$_{16}$

To a magnetically stirred suspension of BHALys[Lys]$_{16}$ [α-Fmoc]$_{16}$[ε-Boc]$_{16}$ (1.0 g, 0.108 mmol) and DMF (10 ml) was added neat piperidine (1 ml, 10.11 mmol) in one portion at room temperature. The suspension was stirred for a further 17 hrs after which time, the crude reaction mixture became a pale yellow solution. The mixture was concentrated under reduced pressure to afford an off white solid which was subsequently suspended in diethyl ether (ca. 100 ml). After stirring for 30 mins at room temperature, the suspension was filtered and the solids collected were left to air dry overnight. The desired product was obtained as a colourless solid (0.60 g, 97%).

LC/MS (Phobic/TFA): ESI (+ve) observed [M+H/4]+ m/z=1441; [M+H/5]+ m/z=1153; [M+H/6]+ m/z=961; calculated for C279H513N63O63 5758.5; Rf (min)=2.95 mins.

Example 22

Preparation of BHALys[Lys]$_{16}$[α-Boc]$_{16}$[ε-NH$_2$Boc]$_{16}$

Preparation of BHALys[Lys]$_{16}$[α-Boc]$_{16}$[ε-Fmoc]$_{16}$ and Preparation of BHALys [Lys]$_{16}$[α-Boc]$_{16}$[ε-Fmoc]$_{16}$ To a stirred mixture of BHALys[Lys]$_{16}$[α-CBz]$_{16}$[ε-Boc]$_{16}$ (0.01 mmol) and dichloromethane (0.5 ml) was added neat TFA (0.5 ml) in a dropwise manner under nitrogen. Stirring was continued at room temperature for 18 h. The volatile reaction components were removed in vacuo and the gummy residue obtained was treated with diethyl ether to induce precipitation of the salt product. The suspension was filtered and the solids collected were washed with diethyl ether. The solids obtained were dissolved in water and concentrated to dryness by freeze drying overnight. The product was obtained as a flocculant, colourless solid.

LC/MS (Hydrophilic/TFA): ESI (+ve) observed [M+H/4]+ m/z=1577; [M+H/5]+ m/z=1262 calculated for C$_{327}$H$_{481}$N$_{63}$O$_{63}$ 6302.8

Example 23

Preparation of BHALys[Lys]$_{16}$[α-CBz]$_{16}$[ε-NH$_2$.TFA]$_{16}$

To a stirred mixture of BHALys[Lys]$_{16}$[α-CBz]$_{16}$[ε-Boc]$_{16}$ (0.01 mmol) and dichloromethane (0.5 ml) was added neat TFA (0.5 ml) in a dropwise manner under nitrogen. Stirring was continued at room temperature for 18 h. The volatile reaction components were removed in vacuo and the gummy residue obtained was treated with diethyl ether to induce precipitation of the salt product. The suspension was filtered and the solids collected were washed with diethyl ether. The solids obtained were dissolved in water and concentrated to dryness by freeze drying overnight. The product was obtained as a flocculant, colourless solid.

LC/MS (Hydrophilic/TFA): ESI (+ve) observed [M+H/4]+ m/z=1577; [M+H/5]+ m/z=1262 calculated for $C_{327}H_{481}N_{63}O_{63}$ 6302.8

Example 24

Preparation of BHALys[Lys]$_{16}$[α,α-Boc]$_8$[α,ε-Boc]$_8$ [ε,α-Boc]$_8$[ε,ε-CBz]$_8$ i. Preparation of BHALys[Lys]$_8$[ε-CBz]$_8$[α-Lys]$_8$[Boc]$_{16}$ DBL-OPNP (3.6 g, 7.2 mmol) and triethylamine (2.1 mL, 15 mmol) were added to a stirred solution of BHALys[Lys] [ε-CBz]$_8$[α-NH$_2$.TFA]$_8$ (3 g, 0.75 mmol) in DMF (30 mL). The resulting yellow solution was stirred at room temperature for 16 h. The reaction mixture was added to stirred acetonitrile (300 mL) producing a white precipitate in the yellow solution. This precipitate was collected by filtration and washed with acetonitrile to remove residual colored material. The precipitate was then dried under vacuum at room temperature to provide BHALys[Lys]$_8$[ε-CBz]$_8$[α-Lys]$_8$[Boc]$_{16}$ as a white powder (4.2 g, 98%).

LC/MS (Fast Hydrophobic/TFA): Rf(min)=13.70; ESI (+ve) m/z=1936 ([M+3]/3), 1452 ([M+4]/4), 1062 ([M+5-Boc]/5).; Calc. C295H465N47O71. M+1. 5083.4 ii. Preparation of BHALys[Lys]$_8$[ε-NH$_2$]$_8$[α-Lys]$_8$[Boc]$_{16}$

To a stirred solution of BHALys[Lys]$_8$[ε-CBz]$_8$[α-Lys] [Boc]$_{16}$ (2.2 g, 0.38 mmol) in acetic acid (30 mL), was added 10% Pd/C (101 mg, 0.095 mmol). The resulting homogeneous mixture was at room temperature for 16 h under hydrogen. The solution was filtered and concentrated in vacuo. The resulting sticky residue was redissolved in water and freeze dried to provide BHALys[Lys]$_8$[ε-NH$_2$]$_8$[α-Lys]$_8$[Boc]$_{16}$ (1.97 g, 0.38 mmol) which contained some acetic acid residue.

LC/MS (Hydrophilic/TFA): Rf(min)=18.53; ESI (+ve) m/z=1184 ([M+4]/4), 947 ([M+5]/5), 790 ([M+6]/6).; Calc. C231H417N47O55. M+1. 4731.1 iii. Preparation of BHALys[Lys]$_{16}$[α,α-Boc]$_8$[α,ε-Boc]$_8$[ε,α-Boc]$_8$[ε,ε-CBz]$_8$ PNPO-α-Boc-ε-CBz-Lys (90 mg, 0.18 mmol) and triethylamine (0.05 mL, 0.35 mmol) were added to a stirred solution of BHALys[Lys]$_8$[ε-NH$_2$]$_8$[α-Lys]$_8$[Boc]$_{16}$ (90 mg, 0.019 mmol) in DMF (10 mL). The resulting yellow solution was stirred at room temperature for 16 h. The reaction mixture was then added to stirred acetonitrile (100 mL) producing a white precipitate in the yellow solution. This precipitate was collected by filtration and washed with acetonitrile to remove residual colored material. The precipitate was dried in under vacuum at room temperature to provide BHALys[Lys]$_{16}$[α,α-Boc]$_8$-[α,ε-Boc]$_8$ [ε,α-Boc]$_8$[ε,ε-CBz]$_8$ (51 mg, 35%)

LC/MS (Phobic TFA Speedy Rp): Rf(min)=14.32; ESI (+ve) m/z=2544 ([M+3]/3), 1909 ([M+4]/4), 1527 ([M+5]/5).; Calc. C383H625N63O95. M+1. 7629

Example 25

Preparation of BHALys[Lys]$_{16}$[α,α-Boc]$_8$[α,ε-Boc]$_8$ [ε,α-Boc]$_8$[ε,ε-Fmoc]$_8$ PFP-Lys-α-Boc-ε-Fmoc (96 mg, 0.15 mmol) and triethylamine (0.04 mL, 0.27 mmol) were added to a stirred solution of BHALys[Lys]$_8$[ε-NH$_2$]$_8$[α-Lys]$_8$[Boc]$_{16}$ (100 mg, 0.017 mmol) in DMF (10 mL). The solution was stirred at room temperature for 16 h. The reaction mixture was then added to acetonitrile (100 ml) producing a clear gelatinous precipitate. This precipitate was collected by filtration and washed with acetonitrile. The precipitated was dried at room temperature to provide BHALys[Lys]$_{16}$[α,α-Boc]$_8$[α,ε-Boc]$_8$[ε,α-Boc]$_8$ [ε,ε-Fmoc]$_8$ (30 mg, 21%)

LC/MS (Hydrophobic/TFA): Rf (min)=7.72; ESI (+ve) m/z=1667 ([M+5]/5), 1389 ([M+6]/6), 1191([M+7]/7).; Calc. C439H657N63O95. M+1 8332

Preparation of Defined PEG 1.7 KD

To a stirring solution of HO$_2$C-PEG$_{1146}$-NH$_2$ (245 mg, 0.21 mmol, 1.07 eq) and PEG$_{570}$-NHS (136 mg, 0.2 mmol) in DMF (6 mL) was added 2 mL of buffer (pH 8.5, prepared by addition of 2.5 mL of 0.1 M HCl solution into a stirring solution of Na$_2$HPO$_4$ (100 mL) and stirred for 5 mins after the completion of the addition). The reaction mixture was allows to stir at rt overnight. The solvents were removed on a rotavap to give PEG$_{1716}$-CO$_2$H as a residue which was purified by LC to give the desired product (yield 80%)

Example 26

Preparation of BHALys[Lys]$_8$(α-NH$_2$.TFA)$_8$ (ε-PEG$_{571}$)$_8$ i. Preparation of BHALys[Lys]$_8$(α-Boc)$_8$ (ε-PEG$_{571}$)$_8$ To a stirred solution of BHALys[Lys]$_8$(α-Boc)$_8$ (ε-NH$_2$.TFA)$_8$ (9.2 mg, 0.003 mmol) in dry DMF (1 mL) and DMSO (1 mL) under nitrogen, was added NHS-PEG 685.75 (26 mg, 0.45 mmol) and triethylamine (10 µL, 0.108 mmol). The reaction mixture was allowed to stir at rt for 16 h and then concentrated under reduced pressure to give a crude oil which was purified by prep. HPLC [C18 prep. column: Waters Xterra Prep RP18, 10 µm, 19×250 mm. Ambient temp. Gradient: 10-45% MeCN over 80 mins. Rf (mins) 85]. To give BHALys[Lys]$_8$(α-Boc)$_8$(ε-PEG$_{571}$)$_8$ as a clear oil (18 mg, 75%)

LC-MS: (Phobic, TFA) R$_f$ (min) 12.81. ESI (+ve) m/z=1246.3 (M/6), 1068.2 (M/7), 934.8 (M/8) 831.2 (M/9).

ii. Preparation of BHALys[Lys]$_8$(α-NH$_2$.TFA)$_8$ (ε-PEG$_{571}$)$_8$

To a stirred solution of BHALys[Lys]$_8$(α-Boc)$_8$ (ε-PEG$_{571}$)$_8$ (18 mg, 0.002 mmol) in CH$_2$Cl$_2$ (3 mL) at 0° C. was added TFA (45 µL, 0.58 mmol), stirring at 0° C. was continued for 20 mins then at it for 2 h. The solvents were removed under reduced pressure to give BHALys[Lys]$_8$(α-NH$_2$.TFA)$_8$ (ε-PEG$_{571}$)$_8$ as an oil (16 mg, 88%)

LC-MS: (Philic, TFA) R$_f$(min) 10.36. ESI (+ve) m/z=954 (M/7), 834 (M/8), 742 (M/9).

Example 27

Preparation of BHALys[Lys]$_{16}$[α-PEG$_{570}$]$_{16}$[ε-MTX]$_{16}$

The preparation of the title compound is illustrated with reference to Reaction Scheme 3 (FIG. 17). The reaction scheme is as follows:

BHALys[Lys]$_{16}$[α-Fmoc]$_{16}$[ε-Boc]$_{16}$, Structure 2, FIG. 17, (R$_1$=Fmoc, R$_2$=Boc) is reacted with piperidine in DMF to give BHALys[Lys]$_{16}$[α-NH$_2$]$_{16}$[ε-Boc]$_{16}$, Structure 3f (R$_1$=H, R$_2$=Boc); then Structure 3f is reacted with excess PEG$_{570}$-NHS in DMF with DIPEA to give BHALys[Lys]$_{16}$ [α-PEG$_{570}$]$_{16}$[ε-Boc]$_{16}$, Structure 3g (R$_1$=PEG$_{570}$, R$_2$=Boc); then Structure 3g is reacted with TFA (20%) in DCM, then with ion exchange resin (OH—) form to give BHALys [Lys]$_{16}$[α-PEG$_{570}$]$_{16}$[ε-NH$_2$]$_{16}$, Structure 3h (R$_1$=PEG$_{570}$, R$_2$=NH$_2$), then Structure 3h is reacted with excess α-tBu-γ-MTX-OH, EDC, HOBt and DIPEA in DMSO to give BHALys[Lys]$_{16}$[α-PEG$_{570}$]$_{16}$[ε-(α-tBu-MTX)]$_{16}$, Structure 3i ($R_1$=PEG$_{570}$, $R_2$=α-tBu-MTX), then Structure 3i is reacted with TFA to give BHALys [Lys]$_{16}$[α-PEG$_{570}$]$_{16}$[ε-MTX]$_{16}$, Structure 3j ($R_1$=PEG$_{570}$, $R_2$=MTX).

Substitution of PEG$_{1716}$, PEG$_{2645}$ and PEG$_{3974}$ for PEG$_{570}$-NHS provides dendrimer constructs with increasing PEG sizes, and requires alternative reaction conditions whereby Structure 3f with excess PEG$_{MW}$-CO$_2$H, HOBt and EDC in DMF with DIPEA to give Structure 3g ($R_1$=PEG$_{MW}$ $R_2$=CBz) BHALys[Lys]$_{16}$[α-PEG$_{MW}$]$_{16}$[ε-CBz]$_{16}$

Example 28

Preparation of BHALys[Lys]$_{16}$[α-PEG$_{570}$]$_{16}$[ε-COCH$_2$CH$_2$CO-Taxol]$_{16}$ The preparation of the title compound is illustrated with reference to Reaction Scheme 5 (FIG. 18). The reaction scheme is as follows:

BHALys[Lys]$_{16}$[α-PEG$_{570}$]$_{16}$[ε-NH$_2$]$_{16}$, Structure 3h ($R_1$=PEG$_{570}$, $R_2$=H) with TFA (16 equivalents) is reacted with excess HO$_2$CCH$_2$CH$_2$CO-Taxol, EDC, HOBt and DIPEA in DMF to give BHALys[Lys]$_{16}$[α-PEG$_{570}$]$_{16}$[ε-COCH$_2$CH$_2$CO-Taxol]$_{16}$, structure 31 ($R_1$=PEG$_{570}$, $R_2$=COCH$_2$CH$_2$CO-Taxol).

Substitution of PEG$_{1716}$, PEG$_{2645}$ and PEG$_{3974}$ for PEG$_{570}$ in Structure 3h provides dendrimer constructs with increasing PEG sizes.

Example 29

Preparation of BHALys[Lys]$_{16}$[ε,ε-PEG$_{570}$]$_8$ [COCH$_2$CH$_2$CO-Taxol]$_{24}$ i. Preparation of BHALys[Lys]$_8$[α-NH$_2$]$_8$[ε-CBz]$_8$ The preparation of the intermediate compound is illustrated with reference to Reaction Scheme 6 (Part 1) (FIG. 19A). The reaction scheme is as follows:

BHALys[Lys]$_4$[NH$_2$.TFA]$_8$, Structure 4 ($R_1$=H.TFA) is reacted with excess PNPO-α-Boc-ε-CBz-Lys and DIPEA in DMF to give BHALys[Lys]$_8$[α-Boc]$_8$[ε-CBz]$_8$, Structure 5a ($R_1$=Boc $R_2$=CBz); Structure 5a is reacted with TFA/Acetic acid then ion exchange resin, (OH—) form, to give BHALys[Lys]$_8$[α-NH$_2$]$_8$[ε-CBz]$_8$, Structure 5b ($R_1$=H $R_2$=CBz).

ii. Preparation of BHALys[Lys]$_{16}$[ε,ε-PEG$_{570}$]$_8$ [COCH$_2$CH$_2$CO-Taxol]$_{24}$ The preparation of the title compound is illustrated with reference to Reaction Scheme 6 (Part 2) (FIG. 19B). The reaction scheme is as follows:

BHALys[Lys]$_8$[α-NH$_2$]$_8$[ε-CBz]$_8$, Structure 5b ($R_1$=H $R_2$=CBz) with TFA (8 equivalents) is reacted with excess DBL-OPNP and DIPEA in DMF to give BHALys [Lys]$_8$[ε-CBz]$_8$[Lys]$_8$[α,α-Boc]$_8$[α,ε-Boc]$_8$, Structure 6a ($R_1$=Boc $R_2$=CBz); Structure 6a is reacted with H$_2$ and Pd(10%) on Carbon in acetic acid then ion exchange resin (OH—) form, to give BHALys[Lys]$_8$[ε-NH$_2$]$_8$[Lys]$_8$[α,α-Boc]$_8$[α,ε-Boc]$_8$, Structure 6b ($R_1$=Boc $R_2$=H); Structure 6b with TFA (8 equivalents) is reacted with excess PNPO-α-Boc-ε-CBz-Lys and DIPEA in DMF to give BHALys[Lys]$_{16}$[ε,ε-CBz]$_8$ [Boc]$_{24}$, Structure 7a ($R_1$=Boc $R_2$=CBz); Structure 7a is reacted with H$_2$ and Pd(10%) on Carbon in acetic acid then ion exchange resin, (OH—) form, to give BHALys[Lys]$_{16}$[ε,ε-NH$_2$]$_8$ [Boc]$_{24}$, Structure 7b ($R_1$=Boc $R_2$=H); Structure 7b is reacted with excess PEG$_{570}$-NHS in DMF with DIPEA to give BHALys[Lys]$_{16}$[ε,ε-PEG$_{570}$]$_8$[Boc]$_{24}$, Structure 7c ($R_1$=Boc $R_2$=PEG$_{570}$); Structure 7c is reacted with TFA to give BHALys[Lys]$_{16}$[ε,ε-PEG$_{570}$]$_8$[NH$_2$.TFA]$_{24}$, Structure 7d ($R_1$=H.TFA $R_2$=PEG$_{570}$); Structure 7d I reacted with excess HO$_2$CCH$_2$CH$_2$CO-Taxol, EDC, HOBt and DIPEA in DMF to give BHALys [Lys]$_{16}$[ε,ε-PEG$_{570}$]$_8$ [COCH$_2$CH$_2$CO-Taxol]$_{24}$, Structure 7e ($R_1$=COCH$_2$CH$_2$CO-Taxol $R_2$=PEG$_{570}$).

Substitution of PEG$_{1716}$, PEG$_{2645}$ and PEG$_{3974}$ for PEG$_{570}$-NHS provides dendrimer constructs with increasing PEG sizes, and requires alternative reaction conditions whereby Structure 7b is reacted with excess PEG$_{MW}$-CO$_2$H with HOBt and EDC DMF with DIPEA to give BHALys [Lys]$_{16}$[ε,ε-PEG$_{MW}$]$_8$[Boc]$_{24}$, Structure 7c ($R_1$=Boc $R_2$=PEG$_{MW}$).

Example 30

Preparation of Defined PEG Moieties: PEG$_{1716}$, PEG$_{2645}$, PEG$_{3974}$

The preparation of the above alternative PEG moieties for substitution in the above reaction schemes is illustrated with Reaction Scheme 7 (FIG. 20). The reaction scheme is as follows:

i. HO$_2$C-PEG$_{1146}$-NH$_2$ is reacted with PEG$_{570}$-NHS in DMF-Buffer pH 8.5 to give PEG$_{1716}$-CO$_2$H; ii. PEG$_{1716}$-CO$_2$H is reacted with DCC and NHS, then HO$_2$C-PEG$_{1146}$-NH$_2$ in DMF-Buffer pH 8.5 to give PEG$_{2845}$-CO$_2$H; iii. PEG$_{2845}$-CO$_2$H is reacted with DCC and NHS, then HO$_2$C-PEG$_{1146}$-NH$_2$ in DMF-Buffer pH 8.5 to give PEG$_{3974}$-CO$_2$H

Example 31

Preparation of BHALys[Lys]$_2$[Su(NPN)$_2$]$_4$[α-tBu-MTX]$_4$[PEG$_{570}$]$_4$ i. Preparation of N-(Benzyloxycarbonyl)-3-bromopropylamine

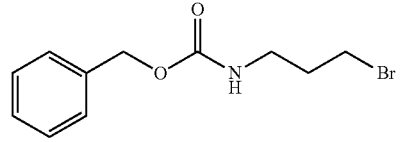 [SMILES: O=C(NCCCBr)OCc1ccccc1]

TEA (6.91 g, 68.5 mmol) was added dropwise to an ice-cooled mixture of 3-bromopropylamine.hydrobromide (10.0 g, 45.6 mmol) and N-(Benzyloxycarbonyloxy)-succinimide (11.22 g, 47.9 mmol) in DCM (200 mL). The stirred mixture was allowed to warm to room temperature overnight, then washed with water (3×), brine, dried (MgSO4), filtered and concentrated, providing 11.43 g (92%) of N-(Benzyloxycarbonyl)-3-bromopropylamine, as a pale yellow oil.

ii. Preparation of [BOC][Cbz][NPN]$_2$

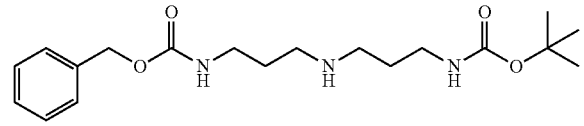 [SMILES: CC(C)(C)OC(=O)NCCCNCCCNC(=O)OCc1ccccc1]

TEA (17.1 mLs, 123.5 mmol) was added dropwise to a stirred mixture of N-(Benzyloxycarbonyl)-3-bromopropylamine (11.20 g, 41.2 mmol) and N-BOC diaminopropane (7.16 g, 41.2 mmol) in DMF (150 mLs) at room temperature. The mixture was heated to 70° C. for one hour, then ca. ⅔rds of the solvent was removed in vacuo. The concentrated DMF mixture was then diluted with water (400 mL) and washed with ether (3×200 mLs) to remove most of the overalkylated byproducts. The DMF/aqueous mixture was then basified (1.0M NaOH), and extracted with ether (5×200 mL). The combined ether extracts were then washed with water (3×200 mL) to remove any unreacted N-BOC diaminopropane, dried (MgSO₄), filtered and concentrated to provide 7.13 g (47%) of [BOC][Cbz][NPN]₂ as a clear colourless oil.

iii. Preparation of [BOC][Cbz][NPN]₂SuOH

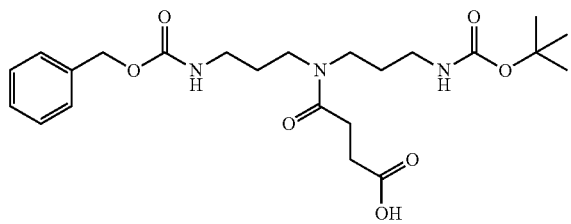 [SMILES: CC(C)(C)OC(=O)NCCCN(CCCNC(=O)OCc1ccccc1)C(=O)CCC(=O)O]

To a stirred mixture of [BOC][Cbz][NPN]₂ (6.55 g, 17.9 mmol) in toluene (60 mL) at room temperature was added succinic anhydride (1.79 g, 17.9 mmol). The mixture was heated to 70° C. for one hour, then concentrated. The residue was then dissolved in EA/ether (5:1) and washed with NaOH (1.0M, 2×100 mL). The base washes were then washed with ether, then neutralised (HCl, 1.0 M, 2×100 mL). The aqueous mixture was then washed with EA (3×250 mL), dried (MgSO4), filtered, and concentrated, providing 6.97 g (84%) of [BOC][Cbz][NPN]₂SuOH as a colourless viscous oil.

iv. Preparation of [BOC][Cbz][NPN]₂SuOPNP

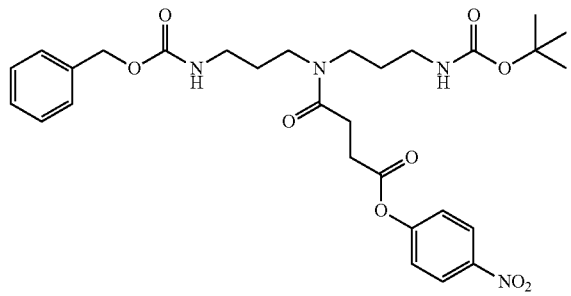 [SMILES: CC(C)(C)OC(=O)NCCCN(CCCNC(=O)OCc1ccccc1)C(=O)CCC(=O)Oc1ccc([N+](=O)[O-])cc1]

To a stirred mixture of 4-nitrophenol (1.91 g, 13.7 mmol) and [BOC][Cbz][NPN]₂SuOH (6.39 g, 13.7 mmol) in EA (150 mL) at room temperature was added DCC (2.97 g, 14.4 mmol), dissolved in EA (50 mL). The mixture was left to stir at room temperature overnight, then filtered (to remove DCU). The mixture was then washed with K₂CO₃ (1.0 M)/Brine 1:1 (3×300 mL), brine, dried (MgSO₄), filtered and concentrated, providing [BOC][Cbz][NPN]₂SuOPNP (7.80 g) as crude material.

v. Preparation of [BOC][Cbz][NPN]₂SuOEt

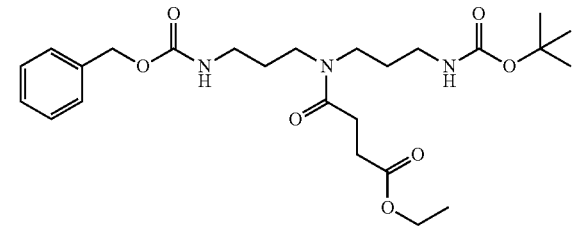 [SMILES: CCOC(=O)CCC(=O)N(CCCNC(=O)OCc1ccccc1)CCCNC(=O)OC(C)(C)C]

A stirred mixture of [BOC][Cbz][NPN]₂SuOPNP (1.16 g, 1.98 mmol) and TEA (2.0 mL, 14.4 mmol) in EtOH (100 mL) was heated at 70° C. for 2 d, concentrated, then taken up in ethyl acetate (120 mL). The mixture was then washed with K₂CO₃ solution (5%, 4×200 mL), brine, dried (MgSO₄), filtered, and concentrated, providing 0.87 g (90%) of [BOC][Cbz][NPN]₂SuOEt as a colourless viscous oil.

LCMS (LC: philic, formate, RT=9.3 min.; MS ($M_{calc.}$ $C_{25}H_{39}N_3O_7$=493.61): 511 ([M+NH₄]⁺, 13%), 494([M+H]⁺, 100%), 438 ([M−t−Bu+H]⁺, 15%), 394 ([M−BOC+H]⁺, 13%).

¹H(CDCl₃): δ 7.30-7.38 (m, 5H), 5.70 (br s, 0.5H), 5.25 (br s, 0.5H), 5.10 (br s, 0.5H), 5.10, 5.08 (2s, 2H), 4.70 (br s, 0.5H), 4.12 (q, J=9.0 Hz, 2H), 2.95-3.45 (m, 8H), 2.52-2.70 (m, 4H), 1.73-1.90 (m, 2H), 1.60-1.70 (m, 2H), 1.42, 1.44 (2s, 9H), 1.25 (t, J=9.0 Hz, 3H).

vi. Preparation of [BOC][NH₂][NPN]₂SuOEt

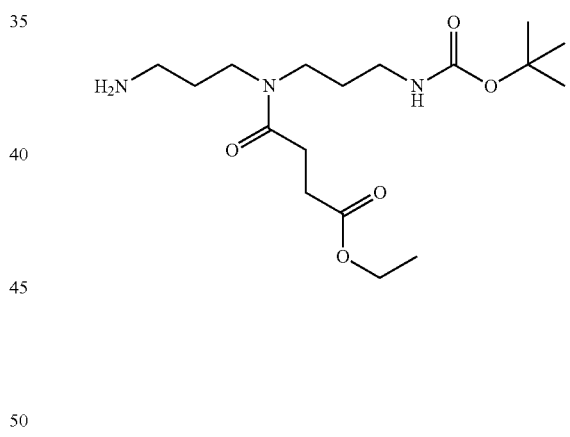

To a stirred mixture of [BOC][Cbz][NPN]₂SuOEt (0.88 g, 1.77 mmol) in DMF/H₂O (9:1, 20 mL) was added ammonium formate (224 mg, 3.55 mmol) and Pd/C (10%, 470 mg). The mixture was stirred for 2 h at rt, then filtered (0.2 μm PALL filter disc) and concentrated. The residue was taken up in water and concentrated (2×). This was then repeated with MeOH and DCM, providing 0.54 g (84%) of [BOC][NH₂][NPN]₂SuOEt as a clear colourless oil.

LCMS (LC: philic, TFA, RT=6.2 min; MS ($M_{calc}$ $C_{17}H_{33}N_3O_5$=359.47): 360([M+H]⁺, 100%).

¹H (CDCl₃): δ 5.30 (br s, 1H), 4.80 (br s, 1H), 4.12 (q, J=9.0 Hz, 2H), 3.29-3.46 (m, 4H), 3.14 (m, 1H), 3.07 (m, 1H), 2.56-2.80 (m, 6H), 1.60-1.90 (m, 4H), 1.42, 1.43 (2s, 9H), 1.25 (t, J=9.0 Hz, 3H).

vii. Preparation of [BOC][PEG$_{570}$][NPN]$_2$SuOEt

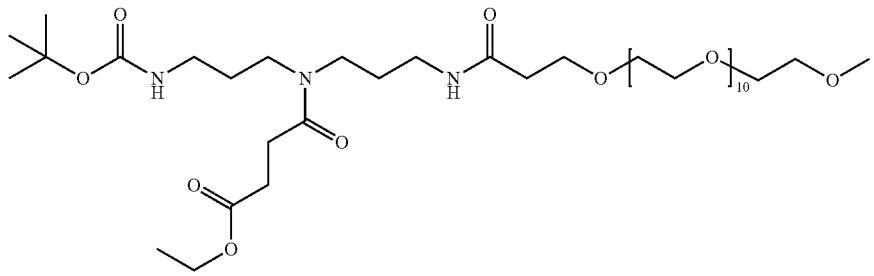

To a stirred mixture of [BOC][NH$_2$][NPN]$_2$SuOEt (157 mg, 0.44 mmol) in DCM (2 mL) was added TEA (121 µl, 0.87 mmol) and PEG$_{570}$-NHS (300 mg, 0.44 mmol) as a DCM (2 mL) solution. The mixture was stirred at rt o/n, concentrated, then purified by fcc (2-10% MeOH/DCM, providing 331 mg (82%) of [BOC][PEG$_{570}$][NPN]$_2$SuOEt as a clear colourless oil.

LCMS (LC: philic, TFA, RT=8.2 min; MS (M$_{calc}$ C$_{43}$H$_{83}$N$_3$O$_{18}$=930.15): 948([M+NH$_4$]$^+$, 12%), 931([M+H]$^+$, 2%), 416(1/2[M−BOC+2H$^+$], 100%).

$^1$H (CDCl$_3$): δ 7.10 (br s, 1H), 7.03 (br s, 1H), 4.16 (g, J=9.0 Hz, 2H), 3.72 (m, 2H), 3.58-3.66 (m, 36H), 3.52-3.56 (m, 2H), 3.47 (s, 2H), 2.96-3.42 (m, 7H), 3.37 (s, 4H), 2.70 (s, 4H), 2.60 (m, 4H), 2.47 (m, 2H), 1.60-1.90 (m, 4H), 1.41, 1.43 (2s, 9H), 1.24 (t, J=9.0 Hz, 3H).

The mixture was stirred at rt for 6 h, concentrated, H$_2$O added and concentrated (2×). The residue was then taken up in H$_2$O again (20 mL), filtered (0.2 □m PALL filter disc) then freeze-dried, providing 0.17 g (93%) of [NH$_2$.TFA][PEG$_{570}$][NPN]$_2$SuOEt as a clear colourless oil.

LCMS (LC: philic, TFA, RT=5.9 min; MS (M$_{calc}$ C$_{38}$H$_{75}$N$_3$O$_{16}$=830.03): 831([M+H]$^+$, 7%), 425(1/2[M+Na$^+$+H$^+$], 30%), 416(1/2[M+2H$^+$], 100%).

$^1$H (D$_2$O): δ 4.17 (g, J=9.0 Hz, 2H), 3.80 (t, J=6.0 Hz, 2H), 3.62-3.75 (m, 43H), 3.38-3.53 (m, 4H), 3.40 (s, 3H), 2.90-3.31 (m, 4H), 2.77 (s, 4H), 2.64-2.89 (m, 4H), 2.52-2.58 (m, 2H), 1.72-2.11 (m, 4H), 1.13 (t, J=9.0 Hz, 3H).

ix. Preparation of [α-tBu-MTX][PEG$_{1570}$][NPN]$_2$SuOEt

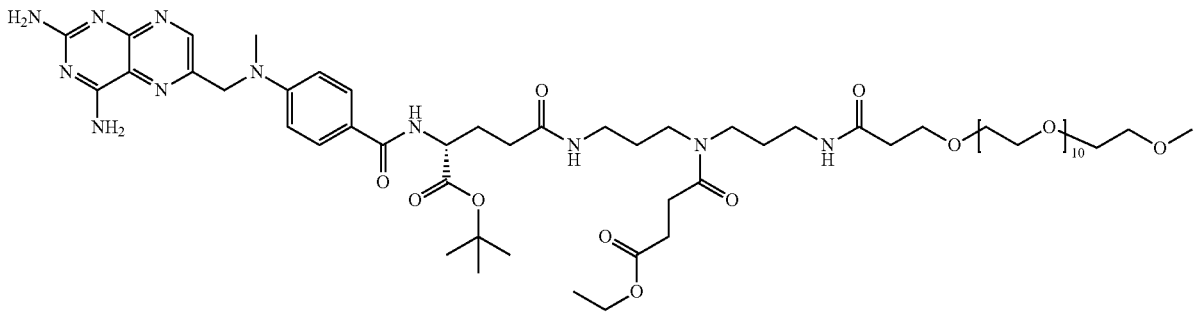

viii. Preparation of [NH$_2$.TFA][PEG$_{570}$][NPN]$_2$SuOEt

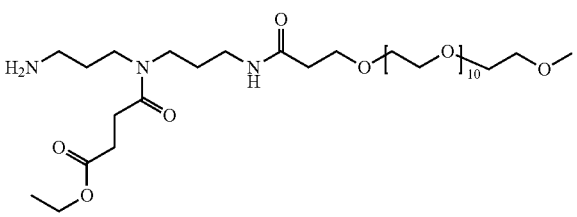

To a stirred mixture of [BOC][PEG$_{570}$][NPN]$_2$SuOEt (180 mg, 0.19 mmol) in DCM (2 mL) was added TFA (0.50 mL).

To a stirred mixture of [NH$_2$.TFA][PEG$_{570}$][NPN]$_2$SuOEt (30 mg, 31.7 µmol) and α-tBu-γ-MTX-OH (16.2 mg, 31.7 µmol) {C. L. Francis, Q. Yang, N. K. Hart, F. Widmer, M. K. Manthey and H. Ming He-Williams, Aust. J. Chem. 2002, 55, 635} in DMF (0.5 mL) at 0° C. was added PyBOP (18 mg, 34.8 µmol) and DIPEA (23 µL, 0.127 mmol). The mixture was stirred at 0° C. for 30 min, then it for 3 h. The DMF was removed, and the residue purified by PTLC (7% MeOH, 93% DCM, Rf=0.3) providing 23 mgs (55%) of [α-tBu-MTX][PEG1$_{570}$][NPN]$_2$SuOEt as an orange oil.

LCMS (LC: philic, TFA, RT=8.0 min; MS (M$_{calc}$ C$_{62}$H$_{103}$N$_{11}$O$_{20}$=1322.57): 1323([M+H]$^+$, 2%), 662(1/2[M+2H], 17%), 634(1/2[M−tBu+2H$^+$], 82%).

x. Preparation of [α-tBu-MTX][PEG$_{570}$][NPN]$_2$SuOH

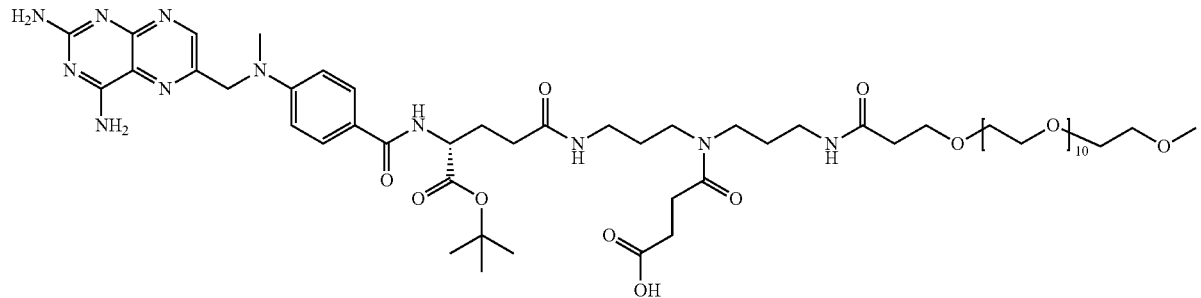

To a stirred mixture of [α-tBu-MTX][PEG1$_{570}$][NPN]$_2$SuOEt (109 mg, 82.4 μmol) in THF/H$_2$O (2:1, 9 mL) was added NaOH (0.16 mL, 1.0M). The reaction was left to stir for 16 h at rt, and additional NaOH added if required (reaction judged by tlc). After the reaction was complete the pH was adjusted to neutral with HCl (1.0M). The solvent was then removed, the residue taken up in MeOH, and filtered to remove salt. The residue was then purified by PTLC (18% MeOH, 82% DCM, Rf=0.4) providing 52 mgs (49%) of [α-tBu-MTX][PEG$_{570}$][NPN]$_2$SuOH as an orange oil.

LCMS (LC: philic, TFA, RT=6.8 min; MS (M$_{calc}$ C$_{53}$H$_{99}$N$_{11}$O$_{20}$=1294.52): 1317([M+Na]$^+$, 3%), 1295 ([M+H]$^+$, 2%), 648(1/2[M+2H$^+$], 10%), 620(1/2[M−tBu+2H$^+$], 74%), 419(100%).

xi. Preparation of BHALys[Lys]$_2$[Su(NPN)$_2$]$_4$[α-tBu-MTX]$_4$[PEG$_{570}$]$_4$ To a stirred mixture of [α-tBu-MTX][PEG$_{570}$][NPN]$_2$SuOH (10 mg, 7.7 μmol) and BHALys[Lys]$_2$[NH$_2$.TFA]$_4$ (1.43 mg, 1.4 μmol) in DMF (1.2 mL) at 0° C. was added PyBOP (4.0 mg, 7.7 μmol) and DIPEA (3.9 μL, 22.4 μmol). The mixture was stirred at 0° C. for 30 min, then rt for 3 h. The DMF was removed, and the residue purified by PREP HPLC (Waters Xterra MS C$_{18}$, 10 μm, 19×250 mm, 30-60% ACN, 0.1% TFA, 8 mL/min, RT=34 min), providing 2 mg (25% {most came out in void}) of BHALys[Lys]$_2$[Su(NPN)$_2$]$_4$[α-tBu-MTX]$_4$[PEG$_{570}$]$_4$.

LCMS (LC: philic, TFA, RT=8.0 min; MS: 1136(1/5[M+5H$^+$], 18%), 946(1/6[M+6H$^+$], 100%), 812(1/7[M+7H$^+$], 22%) Transforms to 5,673.34. (M$_{calc}$ C$_{271}$H$_{437}$N$_{51}$O$_{79}$=5, 673.80).

Example 32

Preparation of BHALys[Lys]$_4$[Su(NPN)$_2$]$_8$[α-tBu-MTX]$_8$[PEG$_{570}$]$_8$

Reaction of BHALys[Lys]$_4$[NH$_2$.TFA]$_8$ with [α-tBu-MTX][PEG$_{570}$][NPN]$_2$SuOH using a similar procedure to that described in example 31 provided BHALys[Lys]$_4$[Su(NPN)$_2$]$_8$ [α-tBu-MTX]$_8$[PEG$_{570}$]$_8$ (10 mg) (51%) PREP HPLC (5-60% ACN, 90 min, RT 54 min).

LCMS (LC: philic, TFA, RT=9.0 min; MS: 1614(1/7[M+7H$^+$], 26%), 1413(1/8[M+8H$^+$], 73%), 1256(1/9[M+9H$^+$], 100%) Transforms to 11,294.54. (M$_{calc}$ C$_{535}$H$_{873}$N$_{103}$O$_{159}$=11,292.52).

Example 33

Preparation of BHALys[Lys]$_8$[Su(NPN)$_2$]$_{16}$[α-tBu-MTX]$_{16}$[PEG$_{570}$]$_{16}$ Reaction of BHALys[Lys]$_8$[NH$_2$.TFA]$_{16}$ with [α-tBu-MTX][PEG$_{570}$][NPN]$_2$SuOH using a similar procedure to that described in example 31 provided BHALys[Lys]$_8$[Su(NPN)$_2$]$_{16}$ [α-tBu-MTX]$_{16}$[PEG$_{570}$]$_{16}$ (6 mg) (46%) PREP HPLC (5-60% ACN, 90 min, RT 66 min).

LCMS (LC: philic, TFA, RT=9.0 min; MS: 2254(1/10[M+10H$^+$], 24%), 2049(1/11[M+11H$^+$], 56%), 1879(1/12[M+12H$^+$], 100%), 1734(1/13[M+13H$^+$], 55%) Transforms to 22,531.91 (M$_{calc}$ C$_{1063}$H$_{1745}$N$_{207}$O$_{319}$=22,529.73).

BHALys[$^3$H-Lys]$_8$[Su(NPN)$_2$]$_{16}$[α-tBu-MTX]$_{16}$ [PEG570]$_{16}$ was prepared in same manner, 15 mg (65%), 1.27 mCi/g

Example 34

BHALys[Lys]$_{16}$[Su(NPN)$_2$]$_{32}$[α-tBu-MTX]$_{32}$ [PEG$_{570}$]$_{32}$

Reaction of BHALys[Lys]$_{16}$[NH$_2$.TFA]$_{32}$ with [α-tBu-MTX][PEG$_{570}$][NPN]$_2$SuOH using a similar procedure to that described in example 31 provided BHALys[Lys]$_{16}$ [Su(NPN)$_2$]$_{32}$[α-tBu-MTX]$_{32}$[PEG$_{570}$]$_{32}$ (7 mg) (44%) PREP HPLC (5-60% ACN, 90 min, RT 71 min). LCMS (LC: philic, TFA, RT=9.2 min; MS: (M$_{calc}$ C$_{2119}$H$_{3489}$N$_{415}$O$_{639}$=45, 004.27)

Example 35 i. Preparation of [BOC][PEG$_{1100}$][NPN]$_2$SuOEt

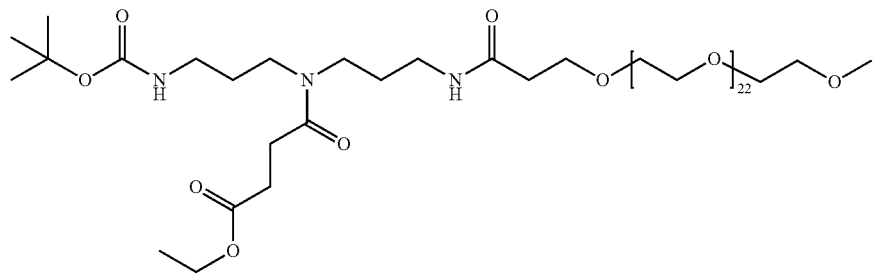

To a stirred mixture of [BOC][NH$_2$][NPN]$_2$SuOEt in DMF (2 mL) was added TEA (2 eq) and PEG$_{1100}$NHS (1 eq) as a DMF/DCM (2 mL) solution. The mixture was stirred at rt o/n, concentrated, then purified by fcc to provide [BOC][PEG$_{1100}$][NPN]$_2$SuOEt as a clear colourless oil.

ii. Preparation of [NH2.TFA][PEG$_{1100}$][NPN]$_2$SuOEt

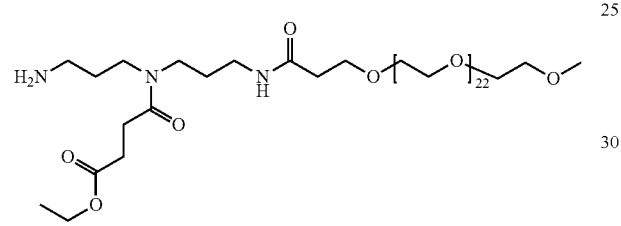

To a stirred mixture of [BOC][PEG$_{1100}$][NPN]$_2$SuOEt (180 mg) in DCM (2 mL) was added TFA (0.50 mL). The mixture was stirred at rt for 6 h, concentrated, H$_2$O added and concentrated (2×). The residue was then taken up in H$_2$O again (20 mL), filtered (0.2 μm PALL filter disc) then freeze-dried, providing [NH$_2$.TFA][PEG$_{1100}$][NPN]$_2$SuOEt as a clear colourless oil.

iii. Preparation of [α-tBu-MTX][PEG$_{1100}$][NPN]$_2$SuOEt

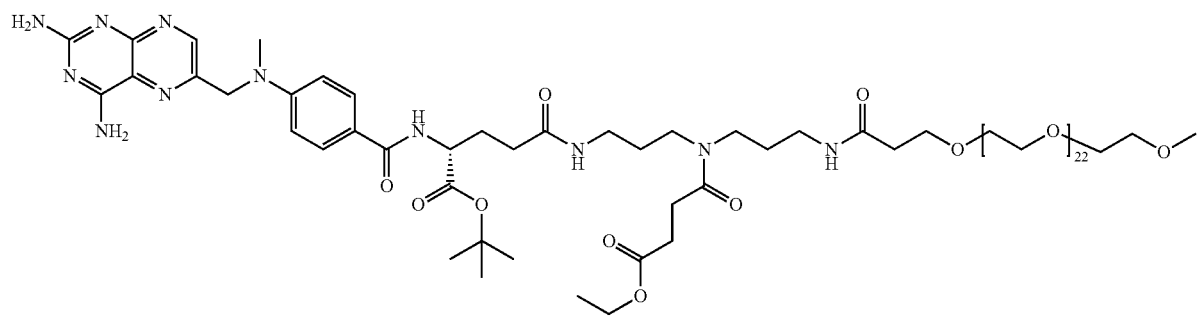

To a stirred mixture of [NH$_2$.TFA][PEG$_{1100}$][NPN]$_2$SuOEt and α-tBu-γ-MTX-OH (1 eq) {C. L. Francis, Q. Yang, N. K. Hart, F. Widmer, M. K. Manthey and H. Ming He-Williams, *Aust. J. Chem.* 2002, 55, 635} in DMF (0.5 mL) at 0° C. was added PyBOP (1.2 eq) and DIPEA (3 eq). The mixture was stirred at 0° C. for 30 min, then rt for 3 h. The DMF was removed, and the residue purified by PTLC providing [α-tBu-MTX][PEG$_{1100}$][NPN]$_2$SuOEt as an orange oil.

iv. Preparation of [α-tBu-MTX][PEG$_{1100}$][NPN]$_2$SuOH

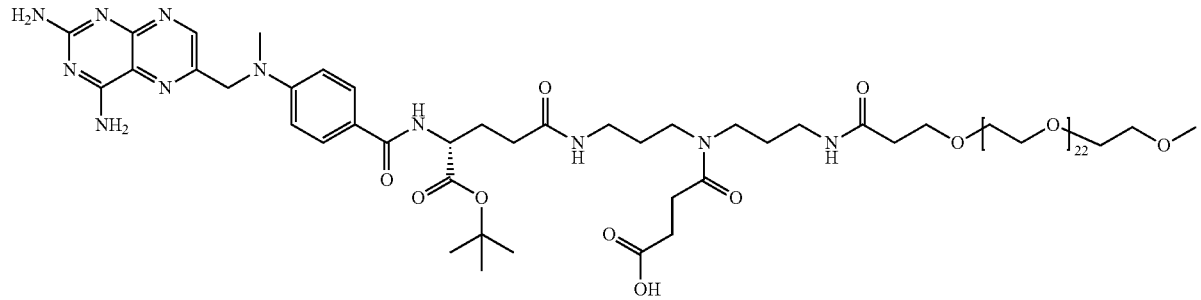

To a stirred mixture of [α-tBu-MTX][PEG1$_{1100}$][NPN]$_2$SuOEt in THF/H$_2$O (2:1, 9 mL) was added NaOH (2 eq, 1.0M). The reaction was left to stir for 16 h at rt, and additional NaOH added if required (reaction judged by tlc). After the reaction was complete the pH was adjusted to neutral with HCl (1.0M). The solvent was then removed, the residue taken up in MeOH, and filtered to remove salt. The residue was then purified by PTLC [α-tBu-MTX][PEG$_{1100}$][NPN]$_2$SuOH as an orange oil.

v. Preparation of BHALys[Lys]$_8$[Su(NPN)$_2$]$_{16}$[α-tBu-MTX]$_{16}$[PEG$_{1100}$]$_{16}$ To a stirred mixture of [α-tBu-MTX][PEG$_{1100}$][NPN]$_2$SuOH (1.1 eq per NH$_2$) and BHALys [Lys]$_8$ [NH$_2$.TFA]$_{16}$ in DMF (1.2 mL) at 0° C. was added PyBOP (1.2 eq per NH$_2$) and DIPEA (3 eq per NH$_2$). The mixture was stirred at 0° C. for 30 min, then rt for 3 h. The DMF was removed, and the residue purified by PREP HPLC (Waters Xterra MS C$_{18}$, 10 μm, 19×250 mm), providing BHALys [Lys]$_8$[Su(NPN)$_2$]$_{16}$[α-tBu-MTX]$_{16}$[PEG$_{1100}$]$_{16}$ Example 36

Preparation of HOGlyLys[Lys]$_2$[Boc]$_3$[ε,ε-CBz]

The synthesis is schematically illustrated in FIG. 21.

i. Preparation of MeOGlyLys[α-Boc][ε-CBz]

PNPO-α-Boc-ε-CBz-Lys (50.15 g, 0.100 mol) was added to a stirred suspension of methyl glycinate hydrochloride (12.56 g, 0.110 mol) in a mixture of triethylamine (30.36 g, 0.300 mol) and dimethylformamide (200 ml). After stirring at ambient temperature for 16 h, the volatile components were evaporated in vacuo and the residue partitioned between ethyl acetate (200 ml) and 5% aqueous sodium carbonate (175 ml). The aqueous phase was discarded and the ethyl acetate phase washed with more 5% aqueous sodium carbonate (4×200 ml) followed by 0.25 M hydrochloric acid (2×50 ml) and then with saturated aqueous sodium chloride (50 ml). The ethyl acetate solution was dried (magnesium sulphate), filtered and the solvent evaporated in vacuo to give MeOGlyLys[α-Boc] [ε-CBz] (44.39 g, 98%) as a colourless oil.

$^1$H nmr (300 MHz, CD$_3$OD) δ (ppm): 1.3-1.8 (m, 6H); 1.44 (s, 9H); 3.13 (t, J 6.6 Hz, 2H); 3.70 (s, 3H); 3.88 (d, J 17.7 Hz, 1H); 3.99 (d, J 17.7 Hz, 1H); 4.04 (m, 1H); 5.06 (s, 2H); 7.2-7.4 (m, 5H).

LC/MS (Hydrophobic/Formate): ESI (+ve) observed [M+H]$^+$ m/z=452.0; calculated for C$_{22}$H$_{34}$N$_3$O$_7$ 452.2. Rf (min)=5.2.

ii. Preparation of MeOGlyLys[α-NH$_2$.TFA][ε-CBz]

MeOGlyLys[α-Boc][ε-CBz] (43.36 g, 96.0 mmol) was dissolved in acetic acid (150 ml) and the solution was stirred at ice bath temperature until the acetic acid began to freeze. The ice bath was removed and trifluoroacetic acid was added slowly with stirring until the acetic acid crystals dissolved. The solution was once again placed in the ice bath and the reminder of the trifluoroacetic acid (150 ml total) was added slowly; freezing of acetic acid did not recur. The ice bath was removed and the solution was stirred at ambient temperature for 5 h and then the volatile components were evaporated as thoroughly as possible in vacuo. The residual viscous oil was dissolved in methanol (200 ml) and again rotary evaporated in vacuo down to an oil. This process was repeated with five additional 200 ml aliquots of methanol before removing as much residual methanol as possible in vacuo at 0.1 Torr. The product, MeOGlyLys[α-NH$_2$.TFA][ε-CBz] was obtained as a pale yellow oil (46.04 g, 103% of theory due to some methanol still being present).

$^1$H nmr (300 MHz, CD$_3$OD) δ (ppm): 1.5-1.6 (m, 4H); 1.8-2.0 (m, 2H); 1.44 (s, 9H); 3.15 (t, J 6.8 Hz, 2H); 3.71 (s, 3H); 3.88 (t, J 6.4 Hz, 1H); 3.94 (d, J 17.6 Hz, 1H); 4.08 (d, J 17.6 Hz, 1H); 5.07 (s, 2H); 7.2-7.4 (m, 5H).

LC/MS (Hydrophilic/Formate): ESI (+ve) observed [M+H]$^+$ m/z=352.1; calculated for C$_{17}$H$_{26}$N$_3$O$_5$ 352.2. Rf (min)=12.3.

iii. Preparation of MeOGlyLys[ε-CBz][α-Lys][Boc]$_2$

DBL-OPNP (49.37 g, 0.106 mol) was added to a stirred solution of MeOGlyLys[α-NH$_2$.TFA][ε-CBz] (46.0 g, 96.0 mmol) and triethylamine (24.3 g, 0.240 mol) in dimethylformamide (200 ml). After stirring at ambient temperature for 17 h a solution of glycine (3.98 g, 53.0 mmol) in water (50 ml) was added and the cloudy solution was stirred for 24 h. Water (150 ml) was added to the well stirred mixture and a white solid began to precipitate. Flaked ice (200 g) was then added and stirring continued until the ice had melted. The solid was collected by filtration, suspended in 5% aqueous sodium carbonate and sonicated for 0.5 h., semi dried with suction and then washed with more 5% aqueous sodium carbonate (2×200 ml) followed by water (3×200 ml). The bright yellow solid was then stirred in a further 200 ml of 5% aqueous sodium carbonate and filtered to give a pale yellow powder. The solid was washed with water (2×200 ml) then suspended in more water (200 ml) and sonicated for 1.5 h. Filtration and suction drying followed by drying in vacuo gave 61.0 g of tan coloured powder. Recrystallisation from ethyl acetate gave MeOGlyLys[ε-CBz][α-Lys][Boc]$_2$ (50.05 g, 77%) as a white solid.

$^1$H nmr (300 MHz, CD$_3$OD) δ (ppm): 1.2-2.0 (m, 30H); 3.03 (t, J 6.6 Hz, 2H); 3.12 (t, J 6.8 Hz, 2H); 3.69 (s, 3H); 3.87 (d, J 17.6 Hz, 1H); 4.00 (d, J 17.6 Hz, 1H); 4.01 (dd, J 3.3, 7.4 Hz, 1H); 4.38 (dd, J 5.4, 8.4 Hz, 1H), 5.06 (s, 2H); 7.2-7.4 (m, 5H).

LC/MS (Hydrophilic/Formate): ESI (+ve) observed [M+H]$^+$ m/z=680.0; calculated for C$_{33}$H$_{54}$N$_5$O$_{10}$ 680.4; observed [M+NH$_4$] m/z=697.0; calculated for C$_{33}$H$_{57}$N$_6$O$_{10}$ 697.4. Rf (min)=8.0.

iv. Preparation of MeOGlyLys[ε-NH$_2$.TFA][α-Lys][Boc]$_2$

A solution of MeOGlyLys[ε-CBz][α-Lys][Boc]$_2$ (680 mg, 1.00 mmol) and trifluoroacetic acid (77 μl, 1.0 mmol) in methanol (10 ml) was added to a suspension of 10% w/w palladium on carbon (106 mg, 0.10 mmol Pd) under hydrogen at atmospheric pressure. The mixture was stirred at ambient temperature for 1 h and then filtered through a bed of celite. Methanol was evaporated in vacuo, the residue redissolved in methanol (5 ml) and the solution passed through a 0.2 μm filter. Evaporation of methanol in vacuo gave MeOGlyLys[ε-NH$_2$.TFA][α-Lys][Boc]$_2$ (640 mg, 97%) as a brittle white foam.

$^1$H nmr (300 MHz, CD$_3$OD) δ (ppm): 1.2-2.0 (m, 30H); 2.93 (t, J 7.5 Hz, 2H); 3.03 (t, J 6.6 Hz, 2H); 3.72 (s, 3H); 3.89 (d, J 17.7 Hz, 1H); 3.98 (dd, J 5.4, 9.0 Hz, 1H); 4.02 (d, J 17.7 Hz, 1H); 4.42 (dd, J 5.7, 8.4 Hz, 1H).

LC/MS (Hydrophilic/Formate): ESI (+ve) observed [M+H]$^+$m/z=546.2; calculated for C$_{25}$H$_{48}$N$_5$O$_8$ 546.3. Rf (min)=14.2.

v. Preparation of MeOGlyLys[Lys]2 [Boc]3 [ε,ε-CBz]

PNPO-α-Boc-ε-CBz-Lys (535 mg, 1.07 mmol) was added to a stirred solution of MeOGlyLys[ε-NH$_2$.TFA][α-Lys][Boc]$_2$ (640 mg, 0.97 mmol) in dimethylformamide (10 ml). Triethylamine (340 μl, 2.43 mmol) was added and the solution was stirred at ambient temperature for 20 h. A solution of glycine (40 mg, 0.54 mmol) in water (5 ml) was added and the cloudy solution was stirred for 2 h. The dimethylformamide was evaporated in vacuo and the residual oil partitioned between ethyl acetate (20 ml) and a 3:1 mixture of 5% aqueous sodium carbonate and saturated aqueous sodium chloride (20 ml). The aqueous phase was discarded and the ethyl acetate phase washed with more of the sodium carbonate/sodium chloride mixture (3×20 ml) followed by 0.20 M hydrochloric acid (2×20 ml) and then with saturated aqueous sodium chloride (20 ml). The ethyl acetate solution was dried (sodium sulphate), filtered and the solvent evaporated in vacuo to give MeOGlyLys[Lys]$_2$[Boc]$_3$[ε,ε-CBz] (818 mg, 93%) as a brittle white foam.

$^1$H nmr (300 MHz, CD$_3$OD) δ (ppm): 1.2-2.0 (m, 45H); 3.03 (t, J 6.6 Hz, 2H); 3.12 (t, J 6.6 Hz, 2H); 3.19 (m, 2H); 3.71 (s, 3H); 3.88 (d, J 17.4 Hz, 1H); 3.93-4.06 (m, 2H); 4.00 (d, J 17.7 Hz, 1H); 4.38 (dd, J 5.4, 8.4 Hz, 1H); 5.07 (s, 2H); 7.25-7.45 (m, 5H).

LC/MS (Hydrophobic/Formate): ESI (+ve) observed [M+H]$^+$ m/z=908.4; calculated for C$_{44}$H$_{74}$N$_7$O$_{13}$ 908.5; observed [M+NH$_4$]$^+$ m/z=925.4; calculated for C$_{44}$H$_{77}$N$_8$O$_{13}$ 925.5. Rf (min)=9.5.

vi. Preparation of HOGlyLys[Lys]$_2$[Boc]$_3$[ε,ε-CBz]

MeOGlyLys[Lys]$_2$[Boc]$_3$[ε,ε-CBz] (500 mg, 0.55 mmol) was dissolved in a solution of sodium hydroxide (44 mg, 1.10 mmol) in methanol (8 ml) and water (4 ml). The solution was stirred at ambient temperature for 4 h and the solvents were evaporated in vacuo. The residue was dissolved in water (10 ml) and 1 M potassium hydrogen sulfate (2 ml) was added. The resultant white precipitate was extracted into ethyl acetate (10 ml) and the aqueous phase was discarded. The ethyl acetate phase was washed with saturated aqueous sodium chloride (10 ml), dried (sodium sulphate), filtered and the solvent evaporated in vacuo to give HOGlyLys[Lys]$_2$[Boc]$_3$[ε,ε-CBz] (481 mg, 96%) as an amorphous white solid.

$^1$H nmr (300 MHz, CD$_3$OD) δ (ppm): 1.2-2.0 (m, 45H); 3.03 (t, J 6.6 Hz, 2H); 3.12 (t, J 6.6 Hz, 2H); 3.19 (m, 2H); 3.84 (d, J 18.0 Hz, 1H); 3.95-4.07 (m, 2H); 3.97 (d, J 17.7 Hz, 1H); 4.39 (dd, J 5.4, 8.4 Hz, 1H); 5.07 (s, 2H); 7.25-7.38 (m, 5H).

LC/MS (Hydrophobic/TFA): ESI (+ve) observed [M+H]$^+$ m/z=894.3; calculated for C$_{43}$H$_{72}$N$_7$O$_{13}$ 894.5. Rf (min)= 8.4.

Example 37

Preparation of BHALys[GlyLys]$_2$[Lys]$_4$[Boc]$_6$[ε,ε-CBz]$_2$ (C$_{105}$H$_{163}$N$_{17}$O$_{25}$ MW 2063.5)

The synthesis is schematically illustrated in FIG. 22.

EDCI (0.90 mmol) was added to a solution of HOGlyLys[Lys]$_2$[Boc]$_3$[ε,ε-CBz] (536 mg, 0.60 mmol), BHALys[NH$_2$.TFA]$_2$ (135 mg, 0.250 mmol), 4,4-dimethylaminopyridine (7.3 mg, 60 umol) and triethylamine (210 ul, 1.50 mmol) in dimethylformamide (10 ml). The solution was stirred at ambient temperature for 15 h and the volatile components were then removed in vacuo. Silica gel chromatography (methanol/dichloromethane gradient) gave BHALys[GlyLys]$_2$[Lys]$_4$[Boc]$_6$[ε,ε-CBz]$_2$ (245 mg, 47%). A small sample (20 mg) was treated with acetic acid/TFA in the usual way to provide analytical data.

LC/MS (Philic/TFA): ESI (+ve) observed [M+H]$^+$ m/z=1463.2; calculated for C$_{75}$H$_{116}$N$_{17}$O$_{13}$ 1462.9.

Example 38

Preparation of BHALys[Lys]$_{16}$[α-PEG$_{570}$]$_{16}$[COCH$_3$]$_{16}$

Acetic anhydride (1.5 eq per NH$_2$) was added to a stirred solution of BHALys[Lys]$_{16}$[α-PEG$_{570}$]$_{16}$[NH$_2$.TFA]$_{16}$ in DMF and TEA (3 eq per NH$_2$) and the reaction allowed to stir overnight. The reaction was concentrated, and the residue purified by size exclusion chromatography on Sephadex G-25 with water as eluent to provide BHALys[Lys]$_{16}$[α-PEG$_{570}$]$_{16}$[COCH$_3$]$_{16}$ Example 39

Lymphatic Targeting of Dendrimers:

Rats were cannulated via the thoracic lymph duct (using a procedure described in M Boyd et al (2003) *Journal of Pharmacology and Toxicology Methods* 49: 115-120) and the right jugular vein (for infusion of saline). Rats were allowed to recover overnight and were supplied with food and water at all times. Animals were administered a 5 mg/kg dose (10 mg/ml, 50 μl per 100 g body weight) of dendrimer (Lys$_{16}$(PEG$_{200}$)$_{32}$, Lys$_{16}$(PEG$_{570}$)$_{32}$, Lys$_{16}$(PEG$_{2000}$)$_{32}$ or Lys$_{16}$(BS)$_{32}$) subcutaneously via injection above the right heel. Lys$_{16}$(BS)$_{32}$ served as a non-PEGylated control dendrimer. Lymph draining into the thoracic lymph duct was collected over 30 to 48 hours and was scintillation counted for tritium radiolabel.

The results of this study demonstrated that up to 40% of a subcutaneous dose of PEGylated poly-L-lysine dendrimer can be taken up by the lymph within 48 hours of an injected dose (FIG. 23). This was dependent on the size of the dendrimer, where 38.5+0.7% (mean±SD, n=3) of Lys$_{16}$(PEG$_{2000}$)$_{32}$ (68 kDa) was taken up into the lymph in 48 hours and 28.8±6.6% of Lys$_{16}$(PEG$_{570}$)$_{32}$ (22 kDa) was recovered in the lymph over 30 hours, whereas only 3.8% (n=1) of Lys$_{16}$(PEG$_{200}$)$_{32}$ (11 kDa) was recovered in thoracic lymph. PEGylation served to increase the uptake of the dendrimers into lymph as only 1.7±1.5% (mean±SD, n=3) of the non-PEGylated benzene sulphonate dendrimer (11 kDa) was taken into lymph in 30 hours (mean±SD, n=3). Approximately 0.3% of the dose of the Lys$_{16}$(PEG$_{570}$)$_{32}$ and Lys$_{16}$(PEG$_{2000}$)$_{32}$ dendrimers were collectively recovered in the right popliteal node and iliac nodes on sacrifice. This represents approximately 2-3% dose/g recovered in the lymph nodes which is considerably higher than the concentration of radiolabel typically recovered in major organs 30-168 hours after an IV dose (up to 1.5% dose/g tissue).

In summary, a significant quantity of the larger (>20 kDa) PEGylated dendrimers was taken up into the regional lymphatics after a subcutaneous dose, whereas much smaller quantities of the smaller (11 kDa) PEGylated or non-PEGylated dendrimers was recovered in lymph. In the case of the non-PEGylated material this also likely reflects reduced drainage from the injection site. A small percentage of the dose was recovered in regional lymph nodes 30-48 hours after an subcutaneous dose, although this represents a relatively high concentration of the dendrimers in lymph nodes given their small mass (approximately 0.1-0.2 g). PEGylation of PLL dendrimers with larger PEG groups may further increase lymph recovery. These results highlight the potential for PEGylation to increase the uptake of drug-dendrimer complexes into the lymph following subcutaneous dosing.

Example 40

Pharmacokinetics of 50%-$PEG_{570}$ Capped Poly-L-Lysine Dendrimers

The following study was conducted to determine how 1) partial surface PEGylation and 2) fully capping the surface of a dendrimer with a combination of PEG and drug/acetyl groups influences dendrimer pharmacokinetics after 5 mg/kg IV dosing to rats.

The following tritiated (G3) dendrimers were used in this study:

$Lys_{16}(NH_2)_{32}$ (MW 4.1 kDa), $BHALys[^3H-Lys]_{16}[NH_2]_{32}$, also referred to in the text as the uncapped dendrimer $Lys_{16}(PEG_{570})_{32}$ (MW 23 kDa), $BHALys[^3H-Lys]_{16}[PEG_{570}]_{32}$, also referred to in the text as the fully PEGylated dendrimer $Lys_{16}(PEG_{570})_{16}(NH_2)_{16}$ (MW 13.3 kDa), $BHALys[^3H-Lys]_{16}[\alpha\text{-}PEG_{570}]_{16}[\epsilon\text{-}NH_2]_{16}$, also referred to in the text as the half-PEGylated dendrimer)

$Lys_{16}(PEG_{570})_{16}(CH_3)_{16}$ (MW 14 kDa), $BHALys[^3H-Lys]_{16}[\alpha\text{-}PEG_{570}]_{16}[\epsilon\text{-}COCH_3]_{16}$, also referred to in the text as the half-acetylated dendrimer)

$Lys_{16}(PEG_{570})_{16}(MTX_{amide})_{16}$*(MW 22.5 kDa), $BHALys[^3H-Lys]_8[Su(NPN)_2]_{16}[PEG_{570}]_{16}[\alpha\text{-}tBu\text{-}MTX]_{16}$, also referred to in the text as the MTX dendrimer, where MTX is methotrexate)

*methotrexate was conjugated to the un-PEGylated sites via a stable amide linker.

Methods

SD rats (approx 300 g) were administered a 5 mg/kg dose of tritiated dendrimer (in 1 ml saline) by direct intravenous infusion via an indwelling cannula in the right jugular vein over 2 minutes. After this time a t0 blood sample was collected from an indwelling cannula in the right carotid artery (0.2 ml) for assessment of Cp0 (concentration of dendrimer in plasma at the conclusion of intravenous infusion). Blood samples were collected thereafter into heparinised tubes at 5, 10, 20, 30, 45, 60, 90, 120, 180, 240, 360, 480, 1440 and 1800 mins. Following centrifugation of the blood samples, 100 µl aliquots of plasma were mixed with 1-2 ml Starscint in 6 ml scintillation tubes and counted for tritium radioactivity. Urine was collected at intervals 0-8 h, 8-24 h and 24-30 h after administration of dendrimer. Aliquots (100 µl) of urine were similarly counted for tritium radioactivity. Urine and plasma samples were analysed by size exclusion chromatography on a Superdex 75 SEC column eluted with 50 mM PBS+0.3M NaCl (pH 3.5). Fractions eluting from the column were collected at 1 min (0.5 ml) intervals, mixed with 2 ml Starscint in 6 ml scintillation vials and scintillation counted for tritium radioactivity.

The potential for dendrimers to bind to vascular or tissue surfaces was estimated by measuring the binding to liver homogenate as a surrogate as follows:

The liver from an anaesthetised rat was perfused with saline to remove the majority of blood in the vasculature. The liver was then isolated and mashed in a glass homogeniser in 1:1 w/v saline. The rat was killed with a lethal injection of Lethabarb via cardiac puncture. Once the liver was visibly homogenised, approximately 1 ml liver homogenate was added to microfuge tubes and centrifuged for 5 min at 3500 rpm. The supernatant was removed and a further 500 µl saline added to each tube. Each tube was vortexed briefly and centrifuged again. This process ensured that soluble proteins were removed from the homogenate as much as possible to minimise the amount of protein that could potentially bind to dendrimer and be counted as un-bound dendrimer. A further 500 µl saline was added to each tube and 50 µg $Lys_{16}(PEG_{570})_{16}(CH_3)_{16}$, $Lys_{16}(PEG_{570})_{16}(NH_2)_{16}$ or $Lys_8(D\text{-}lys)_{16}$ added to each tube. The D-lys dendrimer was used as the cationic, uncapped dendrimer control as it does not undergo rapid metabolism that could affect the results of the binding experiment. Each tube was incubated at 37° C. on a rotary-mixer for 30 min after which the tubes were again centrifuged. The supernatant was collected and analysed for 'unbound' dendrimer. The remaining liver homogenate was solubilised as described elsewhere to ensure that the remainder of the dendrimer was bound to liver tissue.

Results:

$Lys_{16}(PEG_{570})_{16}(NH_2)_{16}$

After administration of the half PEGylated dendrimer, plasma radiolabel declined rapidly with a half life of 8.6±0.3 mins over the first hour (FIG. 24B). For comparison, the plasma profile of the fully uncapped ($Lys_{16}(NH_2)_{32}$) dendrimer is shown in FIG. 24A. An explanation for the difference in initial plasma/distribution kinetics between the fully-uncapped and half-PEGylated dendrimers may be evident in the tissue binding data (Table 13). Thus, the uncapped dendrimer is thought to rapidly bind to the tissues or vasculature (tested using the liver homogenate as a surrogate), resulting in almost immediate removal from plasma. In contrast, even the partially PEGylated materials have much lower tissue or vascular binding activity.

After 1 h the decline in plasma radiolabel slowed dramatically with a terminal half life (calculated over the 6 to 30 hour period) of 22.1±2.1 hours. Size exclusion chromatography (FIG. 25A) suggests the presence of tritiated lysine in the plasma by 2 h post dose and furthermore indicates that the principle species present in plasma is significantly larger than the dendrimer. The terminal half life of approximately 1 day therefore likely reflects the clearance of plasma proteins produced by reincorporation of liberated tritiated lysine.

The plasma pharmacokinetic and SEC profiles for the fully uncapped species suggest that after 30 mins a continual 'supply' of lysine is available to drive the synthesis of plasma proteins (ie. no obvious decline in plasma radiolabel is evident 6-30 hours after dosing, the extended plasma profile is not shown here). The plasma pharmacokinetic and SEC profiles from the half-PEGylated dendrimer however, suggest that whilst a similar degradation and reincorporation process likely occurred it appeared to occur over a narrower period of time since the reincorporation product is eliminated with a half life reflective of the turnover rate of albumin (approximately 24 hours). This relatively brief period of supply of tritiated lysine to drive protein biosynthesis is consistent with the relatively facile renal clearance observed where over the 30 hour sampling period, 73.5±2.8% of administered tritium associated with the half PEGylated dendrimer was recovered in urine. This is in dramatic contrast to the recovery of injected radiolabel from $Lys_{16}(NH_2)_{32}$ and $Lys_{16}(PEG_{570})_{32}$ (approximately 5 and 40% respectively). The species identified in urine co-eluted with intact dendrimer by SEC (FIG. 25B).

TABLE 13

Percentage of dendrimer not bound to liver homogenate after a 30 min incubation at 37° C.

| | % dendrimer not bound to tissues (±sd) |
|---|---|
| $Lys_{16}(PEG_{570})_{16}(NH_2)_{16}$ | 94.6 ± 2.6 |
| $Lys_{16}(PEG_{570})_{16}(CH_3)_{16}$ | 84.5 ± 2.2 |
| $Lys_8(D-Lys)_{16}$ | 3.4 ± 0.4 |

$Lys_{16}(PEG_{570})_{16}(CH_3)_{16}$

The initial plasma profile of radiolabel from the half-acetylated dendrimer was similar to that of the half-PEGylated dendrimer (half life=9.3±0.42 min)(FIG. 24). However, unlike the half-PEGylated dendrimer, the terminal half life of the half-acetylated dendrimer was shorter, and more consistent with the terminal half life of the fully-PEGylated species (13.9±0.3 h for the half-acetylated dendrimer vs 9.45±0.42 h for the fully PEGylated dendrimer). This is likely due to the slower rate of core metabolism for the half-acetylated dendrimer compared to the half-PEGylated dendrimer (FIG. 27A). The plasma SEC profile shows that at t0 plasma radiolabel was attributed entirely to intact dendrimer. Plasma collected 2 hours after dosing showed a small peak attributed to intact dendrimer and a broad peak at 20 mins (this peak eluted 2 mins prior to the intact dendrimer) however, no free lysine was evident. As with the half-PEGylated dendrimer, the majority of the injected radiolabel was excreted in 30 hour urine (72.3±1.2%) and most of this was excreted unchanged. Several small MW species were identified in 8-24 h urine that were attributed to products of dendrimer metabolism (FIG. 27B, note different scales for 8-24 hr).

$Lys_{16}(PEG_{570})_{16}(MTXamide)_{16}$

Although the molecular weight of the MTX dendrimer is similar to the fully-PEGylated dendrimer, the plasma profile more closely mimicked the profile for the half-acetylated dendrimer. The initial plasma half life was 15.4±2.4 min, which was slightly slower than the other half-capped dendrimers. The terminal elimination half life was essentially the same as the fully-PEGylated dendrimer (9±0.2 hr), possibly reflecting the dependence of terminal plasma clearance on overall molecular weight.

Less than one third of the administered dose of tritiated dendrimer was eliminated via the urine over 30 hours (29±3.4). Most of this was excreted over the first 8 hours after the IV dose. The amount of MTX dendrimer excreted in urine was much less than 1) the other half-capped dendrimers and 2) the fully-PEGylated dendrimer (42.9+2.7%). While this small amount of renal elimination cannot be fully explained, it is possible that 1) the large size of the dendrimer hindered renal elimination to some extent, 2) the remainder of the dose was concentrated in the organs of the reticuloendothelial system (RES) and 3) some of the dendrimer may have been retained by organs via interaction with folate binding sites (as MTX is a competitive antagonist for folate at folate receptors).

Conclusions:
1) Lysine dendrimers possessing 50% surface capping with $PEG_{570}$ (but leaving 50% of surface sites uncapped) are eliminated relatively rapidly from plasma and appear to be broken down to liberate free lysine. However, they do not appear to show the same degree of vascular binding as the fully uncapped species.
2) Acetylation of uncapped sites on dendrimers possessing 50% surface PEGylation reduces dendrimer biodegradation when compared with dendrimers where 50% of the surface amines are left uncapped, however the initial rate of clearance/distribution out of the plasma is essentially the same.
3) Lysine dendrimers possessing 50% PEG capping groups and 50% MTX capping groups at the surface show similar initial plasma profiles to the half-acetylated dendrimer.
4) A smaller proportion of the dose of the lysine dendrimers possessing 50% PEG capping groups and 50% MTX capping groups at the surface was recovered in the urine after IV administration when compared with the similar sized fully PEGylated dendrimer, or the 50% acetylated system. This possibly reflects an increased uptake by the RES due to the interaction of the MTX with phagocytic cells in the RES or folate receptors.

REFERENCES

1 Frechet, J. M. J. Dendrimers and other dendritic macromolecules: From building blocks to functional assemblies in nanoscience and nanotechnology J. Polym. Sci. A. 2003, 41, 3713-3725.
2 Beezer, A. E.; King, A. S. H.; Martin, I. K.; Mitchel, J. C.; Twyman, L. J.; Wain, C. F. Dendrimers as potential drug carriers; encapsulation of acidic hydrophobes within water soluble PAMAM derivatives. Tetrahedron 2003, 59, 3873-3880.
3 Kojima, C.; Kono, K.; Maruyama, K.; Takagishi, T. Synthesis of polyamidoamine dendrimers having poly(ethylene glycol) grafts and their ability to encapsulate anticancer drugs. Bioconjug. Chem. 2000, 11, 910-917.
4 Tajarobi, F.; EI-Sayed, M.; Rege, B. D.; Polli, J. E.; Ghandehari, H. Transport of poly amidoamine dendrimers across Madin-Darby canine kidney cells. Int. J. Pharm. 2001, 215, 263-267.
5 EI-Sayed, M.; Ginski, M.; Rhodes, C.; H., G. Transepithelial transport of poly(amidoamine) dendrimers across Caco-2 cell monolayers. J. Control. Release 2002, 81, 355-365.
6 Malik, N.; Wiwattanapatapee, R.; Klopsch, R.; Lorenz, K.; Frey, H.; Weener, J. W.; Meijer, E. W.; Paulus, W.; Duncan, R. Dendrimers: Relationship between structure and biocompatibility in vitro, and preliminary studies on the biodistribution of I-125-labelled polyamidoamine dendrimers in vivo. J. Control. Release 2000, 65, 133-148.
7 Wiwattanapatapee, R.; Carreno-Gomez, B.; Malik, N.; Duncan, R. Anionic PAMAM dendrimers rapidly cross adult rat intestine in vitro: A potential oral delivery system? Pharm. Res. 2000, 17, 991-998.
8 Jevprasesphant, R.; Penny, J.; Jalal, R.; Attwood, D.; McKeown, N. B.; D'Emanuele, A. The influence of surface modification on the cytotoxicity of PAMAM dendrimers. Int. J. Pharm. 2003, 252, 263-266.
9 Sakthivel, T.; Toth, I.; Florence, A. T. Distribution of a lipidic 2.5 nm diameter dendrimer carrier after oral administration. Int. J. Pharm. 1999, 183, 51-55.

10 Florence, A. T.; Sakthivel, T.; Toth, I. Oral uptake and translocation of a polylysine dendrimer with a lipid surface. J. Control. Release 2000, 65, 253-259.

11 Jevprasesphant, R.; Penny, J.; Attwood, D.; D'Emanuele, A. Transport of dendrimer nanocarriers through epithelial cells via the transcellular route. J. Control. Release 2004, 97, 259-267.

12 Gillies, E. R.; Dy, E.; Frechet, J. M. J.; Szoka, F. C., Jr. Biological Evaluation of Polyester Dendrimer: Poly(ethylene oxide) "Bow-Tie" Hybrids with Tunable Molecular Weight and Architecture. Mol. Pharm. 2005, 2, 129-138.

13 Kobayashi, H.; Kawamoto, S.; Saga, T.; Sato, N.; Hiraga, A.; Konishi, J.; Togashi, K.; Brechbiel, M. W. Micro-MR angiography of normal and intratumoral vessels in mice using dedicated intravascular MR contrast agents with high generation of polyamidoamine dendrimer core: Reference to pharmacokinetic properties of dendrimer-based MR contrast agents. J. Magn. Reson. Imaging 2001, 14, 705-713.

14 Kobayashi, H.; Wu, C. C.; Kim, M. K.; Paik, C. H.; Carrasquillo, J. A.; Brechbiel, M. W. Evaluation of the in vivo biodistribution of indium-111 and yttrium-88 labeled dendrimer-1B4M-DTPA and its conjugation with anti-Tac monoclonal antibody. Bioconjug. Chem. 1999, 10, 103-111.

15 Kobayashi, H.; Saga, T.; Kawamoto, S.; Sato, N.; Hiraga, A.; Ishimori, T.; Konishi, J.; Togashi, K.; Brechbiel, M. W. Dynamic micro-magnetic resonance imaging of liver micrometastasis in mice with a novel liver macromolecular magnetic resonance contrast agent DAB-Am64-(1B4M-Gd)(64). Cancer Res. 2001, 61, 4966-4970.

16 Kobayashi, H.; Kawamoto, S.; Saga, T.; Sato, N.; Hiraga, A.; Ishimori, T.; Konishi, J.; Togashi, K.; Brechbiel, M. W. Positive effects of polyethylene glycol conjugation to generation-4 polyamidoamine dendrimers as macromolecular MR contrast agents. Magn. Reson. Med. 2001, 46, 781-788.

17 Margerum, L. D.; Campion, B. K.; Koo, M.; Shargill, N.; Lai, J. J.; Marumoto, A.; Sontum, P. C. Gadolinium(III) DO3A macrocycles and polyethylene glycol coupled to dendrimers—Effect of molecular weight on physical and biological properties of macromolecular magnetic resonance imaging contrast agents. J. Alloys Compounds 1997, 249, 185-190.

18 McCarthy, T. D.; Karellas, P.; Henderson, S. A.; Giannis, M.; O'Keefe, D. F.; Heery, G.; Paull, J. R. A.; Matthews, B. R.; Nolan, G. Dendrimers as Drugs: Discovery and Preclinical and Clinical Development of Dendrimer-Based Microbicides for HIV and STI Prevention Mol. Pharm. 2005, 2, 312-318.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A composition comprising a plurality of macromolecules wherein each of the macromolecules comprises at least one dendritic motif comprising a reactive amine and a carboxyl group, said dendriditc motif having a surface layer and at least one subsurface layer, the macromolecule including at least two terminal groups including:
a first terminal group which is a residue of a pharmaceutical agent, and
a second terminal group selected to modify the pharmacokinetics of the pharmaceutical agent and/or macromolecule,
the first and second terminal groups are attached to the surface layer with a stoichiometry that is not random, such that the abundance of a particular macromolecule with a particular stoichiometry within said plurality of macromolecules is enriched relative to the abundance of said particular macromolecule produced in a randomly surface functionalized plurality of macromolecules wherein terminal group stoichiometry refers to the number and type of terminal groups.

2. The macromolecule according to claim 1, wherein the dendritic motif or the macromolecule further exhibits controlled topology such that the first and second terminal groups are attached to the surface layer with a topology that is not random such that the abundance of a particular macromolecule within said plurality of macromolecules having a particular topology is enriched relative to the abundance of said particular macromolecule produced in a randomly surface functionalized plurality of macromolecules, wherein topology describes the relationship between one terminal group and another in terms of its connection to the surface or subsurface layers of the macromolecule.

3. The macromolecule according to claim 1, wherein the second terminal group is polyethylene glycol (PEG) or polyethyloxazoline.

4. The macromolecule according to claim 1, wherein the second terminal group is a residue of folate or a folate derivative.

5. The macromolecule according to claim 1, wherein the pharmaceutical agent is selected from the group consisting of:
methotrexate; taxol; indomethacin; zenical; and cyclosporine.

6. The macromolecule according to claim 1, wherein the second terminal group is polyethylene glycol having a molecular weight of between 500 and 5000 Daltons.

7. The macromolecule according to claim 1 wherein the surface layer or the at least one subsurface layer of the dendridtic motif comprises at least one lysine and/or lysine analogue selected from the group consisting of:

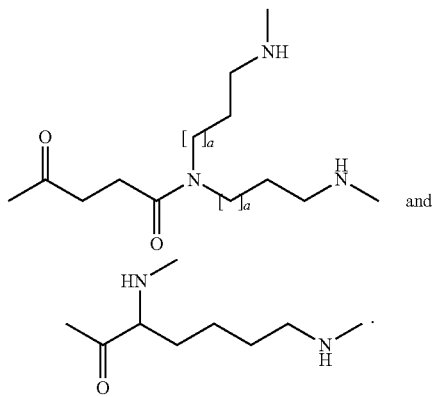

and

8. The composition according to claim 1, wherein the particular macromolecule is enriched by at least two-fold.

9. The composition according to claim 1, wherein the particular macromolecule is enriched by at least four-fold.

10. The composition according to claim 1, wherein the particular macromolecule comprises at least 20% of the plurality of macromolecules.

11. The composition according to claim 1, wherein there are a plurality of the first terminal groups and/or the second terminal groups.

12. The composition according to claim 1 wherein the pharmaceutical agent is selected from the group consisting of: acetonemia preparations; anaesthetics, anti-acid agents; antibodies; anti-fungals; anti-infectives; anti-metabolites; anti-mitotics; anti-protozoals; antiviral pharmaceuticals; biologicals; bronchodilators and expectorants; cardiovascular pharmaceuticals; contrast agents; diuretics; growth hormones; hematinics; hormone replacement therapies; immune suppressives; hormones and analogs; minerals; nutraceuticals and nutritionals; ophthalmic pharmaceuticals; pain therapeutics; respiratory pharmaceuticals; transplantation products; vaccines and adjuvants; anabolic agents; analgesics; anti-arthritic agents; anti-convulsants; anti-histamines; anti-inflammatories; anti-microbials; anti-parasitic agents; anti-ulcer agents; behaviour modification drugs; blood and blood substitutes; cancer therapy and related pharmaceuticals; central nervous system pharmaceuticals; contraceptives; diabetes therapies; fertility pharmaceuticals; growth promoters; hemostatics; immunostimulants; muscle relaxants; natural products; obesity therapeutics; osteoporosis drugs; peptides and polypeptides; sedatives and tranquilizers; urinary acidifiers; and vitamins.

* * * * *